US012098397B2

(12) United States Patent
Fleetwood et al.

(10) Patent No.: US 12,098,397 B2
(45) Date of Patent: Sep. 24, 2024

(54) MATERIALS AND METHODS FOR PRODUCING ALKALOIDS

(71) Applicant: Biotelliga Holdings Limited, Auckland (NZ)

(72) Inventors: Damien James Fleetwood, Auckland (NZ); Mikhail Fokin, Auckland (NZ); Kelly Alexander Styles, Wellington (NZ); Amritha Suhasini Wickramage, Auckland (NZ); Sanjay Saikia, Auckland (NZ)

(73) Assignee: Biotelliga Holdings Limited, Auckland (NZ)

( * ) Notice: Subject to any disclaimer, the term of this patent is extended or adjusted under 35 U.S.C. 154(b) by 0 days.

(21) Appl. No.: 17/879,663

(22) Filed: Aug. 2, 2022

(65) Prior Publication Data
US 2022/0356498 A1 Nov. 10, 2022

Related U.S. Application Data

(63) Continuation of application No. 16/956,476, filed as application No. PCT/IB2018/060481 on Dec. 21, 2018, now abandoned.

(30) Foreign Application Priority Data

Dec. 21, 2017 (NZ) ........................................ 738615

(51) Int. Cl.
*C12N 9/16* (2006.01)
*C12N 9/00* (2006.01)
*C12N 9/02* (2006.01)
*C12N 9/10* (2006.01)
*C12N 9/80* (2006.01)
*C12N 15/80* (2006.01)
*C12P 13/06* (2006.01)
*C12P 17/18* (2006.01)
*C12N 15/52* (2006.01)

(52) U.S. Cl.
CPC ............. *C12N 9/16* (2013.01); *C12N 9/0069* (2013.01); *C12N 9/0071* (2013.01); *C12N 9/1007* (2013.01); *C12N 9/80* (2013.01); *C12N 15/80* (2013.01); *C12P 17/188* (2013.01); *C12N 15/52* (2013.01)

(58) Field of Classification Search
CPC .. C12N 9/0069; C12N 9/0071; C12N 9/1007; C12N 9/16; C12N 9/80; C12P 17/188
See application file for complete search history.

(56) References Cited

U.S. PATENT DOCUMENTS

| 7,183,098 B2 | 2/2007 | Schardl et al. |
| 2004/0139496 A1 | 7/2004 | Schardl et al. |
| 2015/0164069 A1* | 6/2015 | Ford ............... C07C 229/22 424/93.5 |
| 2017/0332641 A1 | 11/2017 | Selwood et al. |

FOREIGN PATENT DOCUMENTS

| WO | WO 2006/076423 A2 | 7/2006 |
| WO | WO 2019/123399 A1 | 6/2019 |

OTHER PUBLICATIONS

A7YVE8_9HYPO. UniProtKB/TrEMBL. Nov. 2016.*
G8EFK3_9HYPO. UniProtKB/TrEMBL. Oct. 2016.*
B9VR32_9HYPO. UniProtKB/TrEMBL. Nov. 2016.*
G8EFK8_9HYPO. UniProtKB/TrEMBL. Apr. 2016.*
Jin. Biotechnol Lett (2008) 30:1379-1383.*
Fransceus (J Ind Microbiol Biotechnol. May 2017;44(4-5):687-695.*
Sanavia (Computational and Structural Biotechnology Journal, vol. 18, 2020, pp. 1968-1979.*
Ballester et al. (2015) "Genome, Transcriptome, and Functional Analyses of *Penicillium expansum* Provide New Insights Into Secondary Metabolism and Pathogenicity," Mol Plant Microbe Interact 28: 232-248.
Behie et al. (2015). Plant tissue localization of the endophytic insect pathogenic fungi Metarhizium and Beauveria. Fungal Ecology, 13, 112-119. https://doi.org/10.1016/j.funeco.2014.08.001.
Bhardwaj (2017) "Formation of the ether bridge in the loline alkaloid biosynthetic pathway," Theses and Dissertations—Chemistry. 75. http://uknowledge.uky.edu/chemistry_etds/75.
Bing et al. (1992) "Temporal relationships between *Zea mays*, ostrinia nubilalis (Lep.: Pyralidae) and endophytic Beauveria bassiana," Entomophaga, 37(4), 525-536. https://doi.org/10.1007/BF02372322.
Blankenship et al. (2001) "Production of loline alkaloids by the grass endophyte, *Neotyphodium uncinatum*, in defined media," Phytochemistry 58: 395-401.
Brownbridge et al. (2012) "Persistence of Beauveria bassiana (Ascomycota: Hypocreales) as an endophyte following inoculation of radiata pine seed and seedlings," Biological Control, 61(3), 194-200. https://doi.org/10.1016/j.biocontrol.2012.01.002.
Cakmak et al. (2011) An efficient synthesis of loline alkaloids, Nat Chem 3: 543-545.
Cermak et al. (2011) "Efficient design and assembly of custom TALEN and other TAL effector-based constructs for DNA targeting," Nucleic Acids Res 39: e82.
Chiang et al. (2013) An efficient system for heterologous expression of secondary metabolite genes in *Aspergillus nidulans*, J Am Chem Soc 135: 7720-7731.
Curtin et al. (2011) Targeted mutagenesis of duplicated genes in soybean with zinc-finger nucleases, Plant Physiol 156: 466-473.

(Continued)

*Primary Examiner* — Yong D Pak
(74) *Attorney, Agent, or Firm* — Leydig, Voit & Mayer, Ltd.

(57) ABSTRACT

The invention generally relates to methods of producing loline alkaloids or precursors thereof, expression constructs, and host cells useful for producing loline alkaloids or precursors thereof, and methods for producing loline alkaloids or precursors thereof in a host cell.

9 Claims, 12 Drawing Sheets

Specification includes a Sequence Listing.

(56) References Cited

OTHER PUBLICATIONS

Database Geneseq [Online], Aug. 21, 2008, "Protein useful for plant improvement, SEQ ID 8229.", Database accession No. ARO95188.
Extended European Search Report for corresponding EP Application No. 18890494.0, dated Dec. 23, 2021, 16 pp.
Faulkner (2011) "Intermediate Steps of Loline Alkaloid Biosynthesis," http://uknowledge.uky.edu/cgi/viewcontent.cgi?article=1212&context=gradschool_diss [retrieved on Jan. 14, 2016] pp. 71-89.
Faulkner et al. (2006) "On the sequence of bond formation in loline alkaloid biosynthesis," ChemBioChem 7: 1078-1088.
Gómez-Vidal et al. (2006) "Endophytic colonization of date palm (Phoenix dactylifera L.) leaves by entomopathogenic fungi," Micron 37(7), 624-632. https://doi.org/10.1016/j.micron.2006.02.003.
Greenfield et al. (Apr. 2016) "Beauveria bassiana and Metarhizium anisopliae endophytically colonize cassava roots following soil drench inoculation," Biological Control, 95, 40-48. https://doi.org/10.1016/j.biocontrol.2016.01.002.
International Search Report and Written Opinion, mailed Apr. 4, 2019, in International Application No. PCT/IB2018/060481, from which the present application claims priority.
Jackson et al. (1996) "Physiological responses of rats fed loline and ergot alkaloids from endophyte-infected tall fescue," Drug Chem Toxicol 19: 85-96.
Li et al. (2012) "High-efficiency TALEN-based gene editing produces disease-resistant rice," Nat Biotechnol 30: 390-392.
Mahfouz et al. (2011) "De novo-engineered transcription activator-like effector (TALE) hybrid nuclease with novel DNA binding specificity creates double-strand breaks," Proc Natl Acad Sci U S A 108: 2623-2628.
Marcet-Houben et al. (Jan. 2016) "Horizontal acquisition of toxic alkaloid synthesis in a clade of plant associated fungi," Fungal Genet Biol 86: 71-80.
Navarro-Sampedro et al. (2007) "How to transform Neurospora crassa by electroporation." http://www.fgsc.net/neurosporaprotocols/How%20to%20transform%20Nc%20by%20electroporation.pdf.
Needleman et al. (1970) "A general method applicable to the search for similarities in the amino acid sequence of two proteins," J Mol Biol 48: 443-453.
Nodvig et al. (2015) "A CRISPR-Cas9 System for Genetic Engineering of Filamentous Fungi," PLoS One 10: e0133085.
Ownley et al. (2009) "Endophytic fungal entomopathogens with activity against plant pathogens: ecology and evolution," BioControl, 55(1), 113-128. https://doi.org/10.1007/s10526-009-9241-x.
Pan (2014) "Ether bridge formation and chemical diversification in loline alkaloid biosynthesis," Theses and Dissertations—Plant Pathology. 14. https://uknowledge.uky.edu/plantpath_etds/14.
Pan et al. (2014) "Enzymes from fungal and plant origin required for chemical diversification of insecticidal loline alkaloids in grass-Epichloë symbiota," PLoS One 9: e115590.
Pan et al. (2014) "Ether bridge formation in loline alkaloid biosynthesis," Phytochemistry, 98, pp. 60-68.
Pan et al. (Mar. 2018) "Installation of the Ether Bridge of Lolines by the Iron- and 2-Oxoglutarate-Dependent Oxygenase, LolO: Regio- and Stereochemistry of Sequential Hydroxylation and Oxacyclization Reactions," Biochemistry 57: 2074-2083.
Posada et al. (2007) "Inoculation of coffee plants with the fungal entomopathogen Beauveria bassiana (Ascomycota: Hypocreales)," Mycological Research, 111(6), 748-757. https://doi.org/10.1016/j.mycres.2007.03.006.
Protein Sequence, homocysteine synthase-like protein [Epichloe uncinata]. Genbank AAN32868.1 (Accession No. AAN32868), Published: Oct. 2, 2002, Whole Document.
Protein Sequence, LoIC-1 [Epichloe uncinata]. GenbankAAV68703.1 (Accession No. AAV68703), Published: Oct. 28, 2008, Whole Document.
Protein Sequence, LoIC-2 [Epichloe uncinata]. UniProtKB/SwissProt: Q5MNH8.1 (Accession No. Q5MNH8 ), Published: Feb. 1, 2005, Whole Document.
Protein Sequence, LoIO-1 [Epichloe uncinata]. Genbank AAV68705.1 (Accession No. AA V68705), Published: Oct. 28, 2008, Whole Document.
Protein Sequence, LoIO-2 [Epichloe uncinata]. Genbank AAV68697.1 (Accession No. AA V68697), Published: Oct. 27, 2008, Whole Document.
Quesada-Moraga (2006) "Endophytic colonisation of opium poppy, Papaver somniferum, by an entomopathogenic Beauveria bassiana strain," Mycopathologia, 161(5), 323-329. https://doi.org/10.1007/s11046-006-0014-0.
Quesada-Moraga et al. (2014) "The Hidden Habit of the Entomopathogenic Fungus Beauveria bassiana : First Demonstration of Vertical Plant Transmission," Plos One, 9(2), e89278. https://doi.org/10.1371/journal.pone.0089278.
Rondot et al. (Jan. 2016) "Endophytic Beauveria bassiana in grapevine Vitis vinifera (L.) reduces infestation with piercing-sucking insects," Biological Control, 116, 82-89. https://doi.org/10.1016/j.biocontrol.2016.10.006.
Russo et al. (2015) "Endophytic colonisation of tobacco, corn, wheat and soybeans by the fungal entomopathogen Beauveria bassiana (Ascomycota, Hypocreales)," Biocontrol Science and Technology, 25(4), 475-480. https://doi.org/10.1080/09583157.2014.982511.
Sander et al. (2011) "Selection-free zinc-finger-nuclease engineering by context-dependent assembly (CoDA)," Nat Methods 8: 67-69.
Sander et al. (2014) "CRISPR-Cas systems for editing, regulating and targeting genomes," Nat Biotechnol 32: 347-355.
Schardl et al. (2007) "Loline alkaloids: Currencies of mutualism," Phytochemistry 68: 980-996.
Schardl et al. (2013) "Plant-symbiotic fungi as chemical engineers: multi-genome analysis of the clavicipitaceae reveals dynamics of alkaloid loci," PLoS Genet 9: e1003323.
Spiering et al. (2002) "Expressed sequence tags and genes associated with loline alkaloid expression by the fungal endophyte Neotyphodium uncinatum," Fungal Genetics and Biology 36, 242-254.
Spiering et al. (2005) "Gene clusters for insecticidal loline alkaloids in the grass-endophytic fungus Neotyphodium uncinatum," Genetics 169: 1403-1414.
Spiering et al. (2008) "Role of the LoIP cytochrome P450 monooxygenase in loline alkaloid biosynthesis," Fungal Genet Biol 45: 1307-1314.
Tzfira et al. (2012) "Genome modifications in plant cells by custom-made restriction enzymes," Plant Biotechnol J 10: 373-389.
Vega (2008) "Insect pathology and fungal endophytes," Journal of Invertebrate Pathology, 98(3), 277-279. https://doi.org/10.1016/j.jip.2008.01.008.
Wagner et al. (2000) "Colonization of Corn, Zea mays, by the Entomopathogenic Fungus Beauveria bassiana," Applied and Environmental Microbiology, 66(8), 3468-3473.
Wilkinson et al. (2000) "Contribution of fungal loline alkaloids to protection from aphids in a grass-endophyte mutualism," Mol Plant Microbe Interact 13: 1027-1033.
Yadav et al. (2010) "A phosphate transporter from the root endophytic fungus Piriformospora indica plays a role in phosphate transport to the host plant," J Biol Chem 285: 26532-26544.
Zhang et al. (2007) "Disruption of the fatty acid Delta6-desaturase gene in the oil-producing fungus Mortierella isabellina by Homologous recombinatio," Curr Microbiol 55: 128-134.
Zhang et al. (2009) "Coregulated expression of loline alkaloid-biosynthesis genes in Neotyphodium uncinatum cultures," Fungal Genet Biol 46: 517-530.
Zhang et al. (2009) "Regulation of a Chemical Defense against Herbivory Produced by Symbiotic Fungi in Grass Plants," Plant Physiology, Jun. 2009, vol. 150, pp. 1072-1082.
Zuccaro et al. (2009) "Karyotype analysis, genome organization, and stable genetic transformation of the root colonizing fungus Piriformospora indica," Fungal Genet Biol 46: 543-550.
GenBank accession No. ABQ57512.1, Sep. 2007.
UniprotKB accession No. 74663825, Oct. 2006.
UniProtKB accession No. 74583992, Oct. 2006.
NCBI reference sequence No. XP_016595151.1, Aug. 2017.

(56) References Cited

OTHER PUBLICATIONS

A. Ortiz-Urquiza et al., "Molecular Genetics of Beauveria bassiana Infection of Insects", Ortiz-Urquiza, A., & Keyhani, N. O. (2016), 165-249, University of Florida, Gainesville, FL, United States.
Timothy R. Gottwald, "Colonization, Transmission, and Longevity of Beauveria bassiana and Metarhizium Anisopliae (Deuteronmycotina: Hypomycetes) on Pecan Weevil Larvae (Coleoptera: Curculionidae) in Soil", Environmental Entomology, Apr. 1984, 5 pgs.
Office Action mailed Apr. 4, 2024 received in corresponding Brazilian Application No. BR112020012297-1, 5 pages.
Office Action mailed May 27, 2023 received in corresponding Chinese Application No. 2018800856757, 8 pages.

* cited by examiner

SEQUENCE LISTING

```
Sequence total quantity: 74
SEQ ID NO: 1            moltype = AA  length = 473
FEATURE                 Location/Qualifiers
source                  1..473
                        mol_type = protein
                        organism = Epichloe festucae
SEQUENCE: 1
MTVDTITSTS NGNQDVPKEF FLKEFETQLL HVGRFPDILG SCAVPVYSSA AFEFNSVAHG   60
ARLLNLTQFG NIYSRFTNPT VNVLQNRLAG LEGGVAACAV ASGSAAVVVT VMALAGVGDN  120
FVSSFHVHAG TFHQFESLAK QMGIECRFVK SRDPADFAAA IDDKTKFVWL ETISNPGNVI  180
LDLEAVSMVC HTKGIPLICD NTFGCAGYFC RPINHGVDIV VHSATKWIGG HGTTVGGIIV  240
DGGTFDWGQH PDRFPQFHDP RTRLWERFSR RAFAVRCQFE ILRDTGSTLS APAAQQLLVG  300
LESLAVRCER HAQNAAKIAD WLREHPLVAW VSYVGHPNHP DYQGALKYLK RGFGSVICFG  360
LRGGFEAGAL FCDALKMVIT TTNLGDAKTL ILHPASTTHE HFRSEHRAEA GVTDDMIRLS  420
VGIEQINDIK ADFEQAFEQV LRGKKSLRKP CIGKILLQDE INEDLFGPSA CRT         473

SEQ ID NO: 2            moltype = AA  length = 418
FEATURE                 Location/Qualifiers
source                  1..418
                        mol_type = protein
                        organism = Epichloe festucae
SEQUENCE: 2
MATAVREAFE NHVKLVESRN SPGHVLASSE ASFFVADLND VVRKWAAWKE ALPDATPFFA   60
VKSSYDRRLI QTLATCGAGF DCASAEEIEL TLSLGIGAER IIFTHPCKPV SSLGLCRKLG  120
ITLITFDNEC ELRKLHHHYP EAQTVLRIFA DDPTNADPLG TKFGAARNDF DGLVRLVKEL  180
NMQLAGASFH AAPSVAVDAA AYVRGIRDAA EVFARARQVG LNPTVLDIGG GYTDSTFQQI  240
AGAVRPAIAE CFTSQVGEGR LRILAEPGTL FSCSPFYLAV KVVARRVNAT AFGHEPATRL  300
YINDGIYSNF MMRFIVNMTF SPTAVIREGV WHDQADHTMR GEACSLWGRS CDSNDCINRD  360
CRLGMKVGVG DWLVFKDMGA YTTVCNTTFN GFTSSNHTIY LEPTQVDKAQ STFEQLAI    418

SEQ ID NO: 3            moltype = AA  length = 540
FEATURE                 Location/Qualifiers
source                  1..540
                        mol_type = protein
                        organism = Epichloe festucae
SEQUENCE: 3
MTLTNLDVIV VGAGFSGILA AHRLRKLGFR VQGFERQERL GGVWRENAYP GAAVDSLFPF   60
YQFYDAELLQ DWEWGEQFPT RAEMLRYFDH VDKRWEISTS FEFGVSVSAA RYSETTQRWT  120
VSLEDGRRAE AQWFIPAVGF SSVLNIPKIP GMSRFRGPIY HTAKWPHDAV SMRGKRVAVI  180
GTGPSGVQII QAVGKIAKAM TIFQQSPCLT LRKYGSPSQT ATALCMRPDD HREALRLGLQ  240
TSNGFGYVIR DQDTLDVPIE ERNHFYQQRY LAGGWAFWMA GFRDLCQNIQ ANRDAYDFWA  300
RRTRARISDV TKRELLVPQI PPFAFGIKRP CLEEDLYEVM DQPHVKVIDI SNQQIELITE  360
TGIRVHGQTV ECEAIIFATG FGDEASGLRS LHIRGRNGIR LEDAWSDGVE SHLGMAIHSF  420
PNMFFLYGPQ CPTLLVNSPA VITVQVEWLC EIISRCQQAG IYQLEATSKS HCQWEKKMSL  480
LWDKTLYHTH ARKSKTTAAA NKEEKTWVGG LILYRRELEN CLANNLEGFQ AWHVEEAALL  540

SEQ ID NO: 4            moltype = AA  length = 209
FEATURE                 Location/Qualifiers
source                  1..209
                        mol_type = protein
                        organism = Epichloe festucae
SEQUENCE: 4
MLDESPMRKG DSVSNDQGNP ESNASVSIHQ QNQIITCVSP DPVCPNAIRI KRDIVIVRLR   60
PVESCPGYRF FRRVFETLEK WQLQVDMFST SLGRITLALG AAALQAGIGD SCSARNDMMS  120
RDLMHGMQKL LPDDHIELFP HMTIISVVEH PSRRMAGHIF ATMDANDIPT VMISHDAARL  180
GIACAISEQY TAKALCVFEQ CLFRYSLTH                                    209

SEQ ID NO: 5            moltype = AA  length = 454
FEATURE                 Location/Qualifiers
source                  1..454
                        mol_type = protein
                        organism = Epichloe festucae
SEQUENCE: 5
MTVNSKRIPF GKPMLEAFCM DPEYTNLNSS SCGSWPKVVS KQIRDYWSLL EAQPDLFSEF   60
SQGLVLQEAR LGLARLVHAA VSECVLVSNV TTGIFTVLYN QAFEERDVVV TLSTTYGAID  120
HGITSLAEAR PFKTRRVEFE LPTTGEKIVS RFETTMAQIR AEGLRPRLAI LETIVSIPAV  180
RMPFEDLLRV CQKEGIMTLV DGAHSVGQFE VNLQELQPDF FVSDCHKWLF VPRPCAFLYV  240
AERNQHMMRS AIPTSFGFIP KNGNSRLPLW SQMVSASETA SSFETLFAYT ATSDNMPHLC  300
IPTALRFRRD VCGGETAIYE YIKWLATEGG DKVANILQTE VLEEPSLGAG VDGQMRDCGI  360
VTVRLPLAIA TGPSTAPAHV PMPGGALTEK EVGPAVRYLT KALAERYKTW IPIIDYRGWI  420
WARLCAQVYL EVSDFEMAGN ALKGICEEIL SRER                              454

SEQ ID NO: 6            moltype = AA  length = 257
FEATURE                 Location/Qualifiers
source                  1..257
                        mol_type = protein
                        organism = Epichloe festucae
SEQUENCE: 6
```

```
MIAASSPHSG VVSAEDIEFY QANGYLRLPQ EAHGLFDDLA KLQVWVAKIS QWGLETGKWR    60
HYYETTNGKH LLWGTEKLME YHAPMRDLIA GDAPLALLKS LTGKDMVVFK DEIGWKLPGG   120
KGAVPHLDRP AYSMFAPEFI EIMIAVDAHT VENGCLQFVP GSHKEAVPIS ADGRIASAWL   180
EGKEFIPMVL DPGDVLIFNE SMAHRLEPNK TDQRRAAVFG TYHFDLSQPD LRDKFYAHRL   240
IHSPPENAWV ETVGAQT                                                  257

SEQ ID NO: 7             moltype = AA   length = 363
FEATURE                  Location/Qualifiers
source                   1..363
                         mol_type = protein
                         organism = Epichloe festucae
SEQUENCE: 7
MTVTNKPVKP ANVPVMDFEA IHASVGNERK KYLRQLDEAW SHHGAIYVIN HSIGTETLEE    60
AFAWCKKFFD LPLAVKNSVH IPPDVSKHFQ GWTGTGEAIS SQGVWDPDEI ERLRKEMPTE   120
LKEAMELQDP CGTYPPGLPD LNLVEQHLPG YLDFLKKWFA ACYRQSLQNM RLVCEILGME   180
DLDYIGKKFA PRHMSTHSTW NYFLGQPVSQ LARGSANRLN AHTDYCQFTM LFQDMVGGLE   240
LHDYEEDIYR PVPPIKGAMI VQVGDLLEKQ TNGRWRSALH RVTAPSRYMY EGSAGDNDEL   300
VQRYSLVFFG HLNLDEMIEP LPGCEKPGKW STLEWKDRMT AGQWLARRVA LEYERKKTAA   360
TVM                                                                 363

SEQ ID NO: 8             moltype = AA   length = 496
FEATURE                  Location/Qualifiers
source                   1..496
                         mol_type = protein
                         organism = Epichloe festucae
SEQUENCE: 8
MVSAGNCAIV APGWTRSEDG TLTRPLDLVE NWLLARIQRA NTPPGREAEG LTYKLKLRLP    60
HDIDDPIPYL RRAWLVFRYV QPLIGAIYPP YSERDETGRY LVTVPPMDPE EWLRLSFHVN   120
QGSQAVFRDV DDAGKIFRPR ETAMAYWFPS SSTLVIRSTH LRFDAVGLYK ATNTFMLGLE   180
SVFRLGLDAN LYCYTTDVKQ PSLPPGIDYI LGFPPQETPV SHRVERAVDE LMRHWHHGLY   240
SLSLPVREGS EDAAPANTQH LVTLFDEPTL EAIVAGCKKL GVSVSAAVHA SIVRVWASFP   300
QQQHTGARNN MLIPLVANLR PLLDPKWVVP DYALSLCIFV VPPCLTGGFE DLTQRLGAVY   360
SRDLSALPSD PAGDPVSFLE LLPLYDSGEA AFLGSLPVAG CPPFRVPNLS SLGVLERYLA   420
RAYGKRGAQA PVCEIEDVAL VNATTDPTIE FQLFTFRGTM RLYLYYNDAY YTEDFLAPVM   480
EMVRDSLLQE LGLGRS                                                   496

SEQ ID NO: 9             moltype = AA   length = 279
FEATURE                  Location/Qualifiers
source                   1..279
                         mol_type = protein
                         organism = Epichloe festucae
SEQUENCE: 9
MTVNSSVKQE YDAQAAIYDG YMDRPSGVIE RQLFTAALGN CTGLTVLDLG GGTGLKAREA    60
ADAGASAVDV IDLSPEMMRV GRDAEQAGPR RGKDILRWYE GDVTSADLVE TLPGLRGPYD   120
LVIVGWTFDH AHNRAQLEAM WHNAVVRLKP STGRLLVVRN GDPRSPAVTG GRYGIRYAGH   180
VPIPGGFRFR DQMIRWGGGG QQQGTKPDQF EILADYETTA LEVMYSGSHE MYHQFGLTDI   240
RTQPYEETAA VRADPAFWAQ FLENPCLAVV TARKMGKVE                          279

SEQ ID NO: 10            moltype = AA   length = 572
FEATURE                  Location/Qualifiers
source                   1..572
                         mol_type = protein
                         organism = Epichloe festucae
SEQUENCE: 10
MSNMRATIAG GARWQEVAAD CQQHRDATVT KIHPPIPDTQ ALESLFASGD PRDVSSIPTL    60
VLSEGELAIT SANVEDLVPR LASGEWSAST VLKAFLRRAA LAQRLVNCVT EMLSETALKR   120
AAELDEHLAV HGKPIGPLHG VPISVKEHIA MKGLDVNGGY VSEVGRVAEE DALILNILRD   180
AGAIFYVRTT EPQSSMHLET SSSLYGETVN PFNTTLTSGG SSGGEAIIA MRGSVLGVGS    240
DIGGSIRSPA HCNGIFGFKP TTGRLPTLGW FALMVGSEAI HATTGPLSTS IEGLRLFTKT   300
LLDAKPWLQD PSLTPMEWRD MSTAFAGRRL KVAVMWDDGV VKPHPPVTRA LKSVVEDLKK   360
SEKIEVVDWK PWKHDLAWSI IAGLYFCDGG AQLNAAFEAA KEPLRPLSHW ILKENPHVKH   420
HSIASLWSAC AERDAYRLKY AELWNDTAKG GGGPVDVILC PAGPGAAPKL NTSRYWGYTA   480
QWNLLDYPAV VFPTGDIVSV EKDGAAGEQG GGDPASGADL DNWSLWTEHG AEGYSNAPLA   540
LQLVARRCDD EKLLHALEMV MKEAGLATEL VG                                 572

SEQ ID NO: 11            moltype = AA   length = 496
FEATURE                  Location/Qualifiers
source                   1..496
                         mol_type = protein
                         organism = Epichloe festucae
SEQUENCE: 11
MDLTQFKTAG IVWPTVAAMA ISYILLSSFL SWYRLRHIPG PFLASISSLW NVLNIVTGRT    60
SPVLEKLPGK YGPMVRTGPN YVLTDDAEIL RHVNGARSTY PRNGWYEGFK VDEHDHMGSH   120
IDTSVHDAIK SKVIGGYNGK DGIDLEGAIG SQVKTLVSEI RRRHLGQPVD FSRLMRQMAL   180
DAITAVAFGE ALGFLTAEDG DVFGYVSAVD KMLTYLTLAS DLPIVRSFVR SRRMAPAVRC   240
VLAYTGIGRM LNHTRRVVAE RYAADDPGKG DMTASFIRKG LTQIECEGES HLQLIAGADT   300
AVTVLRSTLL YIMTTPRVYT RLKAEIKAAV DAGEVVEVIT MAQAQGLPYL QAVVLEGFRM   360
RPAVVYGHFK SVPAGGDTLP NGVRLPAGTA IAPNYIALTR RTDVYGADVD LFRPERFLDA   420
EPAKRHEMER AMDLNFGLGR WQCAGRNIAL MEMNKVFFEL LRHFDLQIVY PGKAWDEYTG   480
```

```
VVYSQHNMWV QITESS                                                   496

SEQ ID NO: 12              moltype = AA  length = 473
FEATURE                    Location/Qualifiers
source                     1..473
                           mol_type = protein
                           organism = Epichloe uncinata
SEQUENCE: 12
MTVDTITSTS NGNQDVPKEF FPKEFETQLL HVGRFPDILG SCAVPVYSSA AFEFNSVAHG     60
ARLLNLTQFG NIYSRFTNPT VNVLQNRLAG LEGGVAACAV ASGSAAVVVT VMALAGVGDN    120
FVSSFHVHAG TFHQFESLAK QMGIECRFVK SRDPADFAAA IDDKTKFVWL ETISNPGNVI    180
LDLEAVSMVC HTKGIPLICD NTFGCAGYFC RPINHGVDIV VHSATKWIGG HGTTVGGVIV    240
DGGTFDWGQH PDRFPQFHDP RTRLWERFSR RAFAVRCQFE ILRDTGSTLS APAAQQLLVG    300
LESLAVRCER HAQNAAKIAD WLREHPLVAW VSYVGHPNHP DHQGALKYLK RGFGSVICFG    360
LRGGFEAGAL FCDALKMVIT TTNLGDAKTL ILHPASTTHE HFSSEHRAEA GVTDDMIRLS    420
VGIEQIKDIK ADFEQAFEQV LRGKKSLRKP CIGKILLQDE INEDLFGPSA CRT           473

SEQ ID NO: 13              moltype = AA  length = 473
FEATURE                    Location/Qualifiers
source                     1..473
                           mol_type = protein
                           organism = Epichloe uncinata
SEQUENCE: 13
MTVDTITSTS NGNQDVPKEF LPIEFETQLL HLGRFPDILG SCAVPVYSSA AFEFNSVAHG     60
ARLLNLTQFG NIYSRFTNPT VNVLQNRLAG LEGGVAACGV ASGSAAVVVT VMALTGVGDN    120
FVSSFHVHAG TFHQFDSLAK QMGIECRFVK SRDPADFAAA IDDKTKFVWL ETISNPGNVI    180
LDLEAVSTVC HTKGIPLICD NTFGCAGYFC RPIDHGVDIV VHSATKWIGG HGTTVGGIIV    240
DGGTFDWGQH PDRFPQFHDP RTRLWERFSR RAFAVRCQFE ILRDTGSTLS APAAQQLLVG    300
LESLAVRCER HAQNAAKIAD WLREYPLVAW VSYVGHPNHP DHQGALKYLK RGFGSVICFG    360
LRGGFEAGAL FCDALKMVIT TTNLGDAKTL ILHPASTTHE HFSSEHRAEA GVTDDMIRLS    420
VGIEQIKDIK ADFEQAFKQV LRGKKSLRKP CIGKILMQDE INEDLFGPSA CRT           473

SEQ ID NO: 14              moltype = AA  length = 420
FEATURE                    Location/Qualifiers
source                     1..420
                           mol_type = protein
                           organism = Epichloe uncinata
SEQUENCE: 14
MATVVREAFE NHVKLVESRN SPGHVLASSE ASFFVADLND IVRKWAAWKK ALPDVTPFFA     60
VKSSYDRRLI QTLATCGAGF DCASVEEIEL ILSLGIGAER IVFTHPCKPV SSLGLCRKLG    120
ITLITFDNEC ELRKLHHHYP EAQTVLRVFA DDPTNADPLG TKFGAAREDI DGLVRLVKEL    180
NMKLAGASFH AAPSVAVDAA AYVRGIRDAA EVFARARRVG LNPTVLDIGG GYTDSTFQQI    240
AGAVRPAIAE CFKSQVVEGR LRILAEPGTL FSCSPFYLAV KVVARRRNAA AFGNEPATRL    300
YINDGIYSNF MMRFIVNMTF SPVAVIRKGV WYDQTEQTMR REACSLWGRS CDSNDCINRD    360
CRLDPEVGVG DWLVFKDMGA YTTVCNTTFN GFTSSNHTIY IEPTQVDKAQ STFEQLELAI    420

SEQ ID NO: 15              moltype = AA  length = 415
FEATURE                    Location/Qualifiers
source                     1..415
                           mol_type = protein
                           organism = Epichloe uncinata
SEQUENCE: 15
MTTVVREAFE NHVKLVESRN SPGHVLASSE ASFFVADLND VVRKWAAWKE ALPDVTPFFA     60
VKSSYDRRLI QTLATCGAGF DCASTEEIEL ILSLGIGAER IIFTHPCKPV SSLGLCRKLG    120
ITLITFDNEC ELRKLHHHYP EAQTVLRVFA DDPTNADPLG TKFGAARDDF DGLVRLVKEL    180
NMQLAGASFH AAPSVAVDAA AYVRGIRDTA EVFARARQVG LNPTVLDIGG GYTDSTFQQI    240
AGAVRPAIAE CFKSEVGEGR LRILAEPGTL FSCSPFYLAV KVVARRVNAT APGHEPATRL    300
YINDGIYSNF MMRFIVNMTF SPAAVIREGV WHDQADHTMR GEACSLWGRS CDSNDCINRD    360
CRLGPEVRVG DWLVFKDMGA YTTVCNTTFN GFTSSNHTIY LEPGTHPSRR SPVDL         415

SEQ ID NO: 16              moltype = AA  length = 540
FEATURE                    Location/Qualifiers
source                     1..540
                           mol_type = protein
                           organism = Epichloe uncinata
SEQUENCE: 16
MTLTNLDVIV VGAGFSGILA VYRLRKLGFR VQGFERQERL GGVWRENAYP GAAVDSLFPF     60
YQFYDAELLQ DWEWVEQFPT RAEMLRYFDH VDKRWEISAS FEFGVSVSAA RYSETTQRWT    120
VSLEDGRRAE ARWFIPAVGF SSVLNIPRIP GMSRFRGPIY HTAKWPHDAV SMRGKRVAVI    180
GTGPSGVQII QSVGKIAKAM TIFQQSPCLT LRKYGSPSQT ATALCMRPDD HREALRLGLQ    240
TSNGFGYVPR DQDTLDVPIE ERNHFYQQRY LAGGWAFWMA GFRDLCQNIQ ANRDAYDFWA    300
RRTRARISDV AKRELLVPQI PSFAFGIKRP CLEEDLYEVM DQPHVKVIDI SNQQIELITE    360
TGIRVHGQTV ECEAIILATG FGDEASGLRS LHIRGRNGIR LEDAWSDGVE SHLGMAIHSF    420
PNMVILYGPQ CPTLLVNSPA VITVQVEWLC EIIARCQQAG ICQLEATSKS HCQWERKMSL    480
LWDKTLYHTH ARKSKKTAEA NKEEKTWVGG LILYRRELEN CLANNLEGFQ AWHVEETGLL    540

SEQ ID NO: 17              moltype = AA  length = 540
FEATURE                    Location/Qualifiers
source                     1..540
```

```
                        mol_type = protein
                        organism = Epichloe uncinata
SEQUENCE: 17
MTLTNLDAIV  VGAGFSGILA  VYRLRKLGFR  VQGFERQERL  GGVWRENAYP  GAAVDSLFPF   60
YQFYDAELLQ  DWEWGEQFPT  RAEMLRYFDH  VDKRWEISAS  FEFGVSVSAA  RYSETTQRWT  120
VTLEDGRRAE  ARWFIPAVGF  SSVLNIPRIP  GMSRFRGAIY  HTAKWPHDAV  SMRGKRVAVI  180
GTGPSGVQII  QSVGKIAKAM  TIFQQSPCLT  LRKYGSPNQT  ATALCMRPDD  HREALRLGLQ  240
TSNGFGYVPR  DQDTLDVPIE  ERNHFYQQRY  LAGGWAFWMA  GFRDLCQNIQ  ANRDAYDFWA  300
RRTRARIGDV  TKRELLVPQI  PSFAFGIKRP  CLEEDLYEIM  DQPHVKIIDI  SNQQIELITE  360
TSIRVHGQTV  ECEAIIFATG  FGDEASGLRS  LHIRGRNGIR  LEDAWSDGVE  SHLGMAIHSF  420
PNMFFLYGPQ  CPTLLVNSPA  VITVQVEWLC  EIISKCQQAG  ICQLEATSKS  HCQWEKKMSL  480
LWDKTLYHTH  ARKSKKTAEA  NKEEKTWVGG  LILYRRELEN  CLANNLEGFQ  AWYVEETALL  540

SEQ ID NO: 18           moltype = AA  length = 209
FEATURE                 Location/Qualifiers
source                  1..209
                        mol_type = protein
                        organism = Epichloe uncinata
SEQUENCE: 18
MLDESPMRKG  DSVSNDQSNP  ESNASVSIHQ  QNQIITCVSP  GPVCPNAIEI  KRDIVIVRLR   60
PVESCPGYRF  FRRVFETLEK  WQLQVDMFST  SLGRITLALG  AAALQAGISD  SCSARNDMMS  120
RDLMHGMQKL  LPDDHIELFP  HMAIISVVGH  PSRRMAGHIF  ATMDANDIPT  VMISHDAARL  180
GIACACAISEQY  TAKALCVFEQ  CLFRYSLTH                                     209

SEQ ID NO: 19           moltype = AA  length = 210
FEATURE                 Location/Qualifiers
source                  1..210
                        mol_type = protein
                        organism = Epichloe uncinata
SEQUENCE: 19
MLDESPMRKG  NSVSNDQGNP  ESNASVSIHQ  QNQIITCASP  GPVCPNAIGI  KRDIVVVRLR   60
PVKSCPDYRF  FRRVFETLEK  WQLQVDMFST  SLGRITLALG  AAALQAGIGD  SCSARNDMMS  120
RDLMHGMQKL  LPDDHILELF  PHMAIISVVG  HPSRRIAGHI  FATMDANDIL  TVMISHDAAR  180
LGIACVISEQ  HTAKALGVFE  QCLFRYSLTH                                      210

SEQ ID NO: 20           moltype = AA  length = 454
FEATURE                 Location/Qualifiers
source                  1..454
                        mol_type = protein
                        organism = Epichloe uncinata
SEQUENCE: 20
MTVNSKRIPF  GKPMLEAFCM  DPEYTNLNSS  SCGSWPKVVS  KQIRDYWSLL  EAQPDLFSEF   60
SQGLVLQEAR  IGLAHLVHAA  VSECVLVSNV  TTGIFTVLYN  QAFEERDVVV  TLSTTYGAID  120
HGITSLAETR  PFKTRRVEFE  LPTTGQKIVS  QFETAMAQIR  ADGLRPRLAI  LETIVSIPAV  180
RMPFEDLLRV  CQKEGIMTLV  DGAHSVGQFE  VNLQELQPDF  FVSDCHKWLF  VPRPCAVLYV  240
AERNQHMMRS  VIPTSFGFIP  KNGNSRLPLW  SQMVSASETA  SSFETLFAYT  ATSDYMPHLC  300
IPAALRFRRD  VCGGEAAIYE  YIKWLAKEGG  DKIADILQTE  VLEEPGLGAG  VDGQMRNCGI  360
VTVRLPLAIA  TGPSTAPAHV  PGGALTEKEV  GPAVRYLTKA  LAERYKTWIP  IIDYRGWIWA  420
RLCAQVYLEV  SDFEMAGNSL  KVICEEILNR  EMGQ                                454

SEQ ID NO: 21           moltype = AA  length = 464
FEATURE                 Location/Qualifiers
source                  1..464
                        mol_type = protein
                        organism = Epichloe uncinata
SEQUENCE: 21
MTVNSKRIPF  GKPMLEAFCM  DPEYTNLNSS  SCGSWPKVVS  KQIRDYWSLL  EAQPDLFSEF   60
YQGLVLQEAR  LGLARLVHAA  VSECVLVSNV  TTGIFTVLYN  QEFEERDVVV  TLSTTYGAID  120
HGITSLAETR  SFKTRRVEFE  LPTTGEKIVS  QFETTIAQIR  AKGLRPRLAI  LETIVSIPAV  180
RMPFEDLLRV  CQKECIMTLV  DGAHSVGQFE  VNLQELHPDF  FVSDCHKWLF  VPRPCAFLYV  240
AERNQHMMRS  AIPTSFGFIP  KNGNSQLPLW  SQMVSANGTA  SSFETLFAYT  ATSDNMPHLC  300
IPTALRFRRD  VCGGEAAIYE  YIKWLAKEGG  DKVAEILQTE  VLEEPGLGAG  ADGQMRDCGI  360
VTVRLPLAIA  TGPSTAPAHV  PGGALTEKEV  GPAVRYLTKA  LADRYKTWIP  IADCRGWIWA  420
RLCAQVYLEV  SDFEMAGNAL  KVICEEILSR  EMGQEISDSY  RWHD                    464

SEQ ID NO: 22           moltype = AA  length = 256
FEATURE                 Location/Qualifiers
source                  1..256
                        mol_type = protein
                        organism = Epichloe uncinata
SEQUENCE: 22
MTAASSPHPG  VSAEDIEFYQ  ANGYLRLPQE  AHGLFDDLAK  LQAWVAEISQ  WGLETGKWRH   60
YYETTNGKHL  LWGTEKLMEY  HAPMRDLIAG  EAPLTLLKSL  TGKDMVVFKD  EIGWKLPGGK  120
GAVPHLDRPA  YSMFAPEFIE  IMIAVDAHTV  ENGCLQFVPG  SHKEAVPISA  DGRIASAWLE  180
GKEFIPMVLD  PGDVLIFNES  MAHRLDPNKT  DQRRAAVFGT  YHFDRSQPDL  RDKFYAHRLI  240
HSPPENAWVE  TVEAQT                                                      256

SEQ ID NO: 23           moltype = AA  length = 256
FEATURE                 Location/Qualifiers
```

```
source                          1..256
                                mol_type = protein
                                organism = Epichloe uncinata
SEQUENCE: 23
MTAASSPHPG VSAEDIEFYQ ANGYLRLPQE AHGLFDDLAK LQVWVAEISQ WGLETGKWRH    60
YYETTNGKHL LWGTEKLMEY HAPMQDLISG EAPLALLKSL TGKDMVVFKD EIGWKLPGGK   120
GAVPHLDRPA YSMFAPEFIE IMIAVDAHTV ENGCLQFVPG SHKEAAPISA DGRIASAWLE   180
GKEFIPMVLD PGDVLIFNES MAHRLEPNKT DQRRAAVFGT YHFDLSQPDL RDKFYAHRLI   240
HSPPENAWVE KVGAQT                                                  256

SEQ ID NO: 24                   moltype = AA   length = 362
FEATURE                         Location/Qualifiers
source                          1..362
                                mol_type = protein
                                organism = Epichloe uncinata
SEQUENCE: 24
MTVTNKPVKP ANVPVMDFEA IHASVGNERK KYLRQLDEAW SHHGAIYVIN HSIGTRTLEE    60
AFAWCKKFFD LPLAVKNSVH IPPDVSKHFQ GWTGTGEAIS SQGVWDPDEI ERLRKETPTE   120
LKEAMELQDP CGTYPPGAPD LNLVEQHLPG FLDFLKKWFA ACYKQSLQNM RLVCEILGME   180
DLDYIGKKFE PRHMSTHSTW NYFLGQPVSQ LASGSANRLN AHTDYCQFTM LFQDMVGGLE   240
LHDYEEDIYR PVPPIKGAMI VQVGDLLEKQ TNGRWRSALH RVTAPSRYMY EGSAGDDDEL   300
VQRYSLVFFG HLNLDEMIEP LPGCEKQGKW STLEWKDRMT AGQWLARRVA LEYERKTAAT   360
VM                                                                 362

SEQ ID NO: 25                   moltype = AA   length = 362
FEATURE                         Location/Qualifiers
source                          1..362
                                mol_type = protein
                                organism = Epichloe uncinata
SEQUENCE: 25
MTVTNKPVEP ANVPVMDFEA IHASVGNERK EYLRQLDEAW SHHGAVYVIN HSIGTETLEE    60
APVWCKKFFD LPLAVKNSVH IPPDVSKHFQ GWTGTGEAIS SQGVWDPDEI ERLRKEMPTE   120
LKEAMELQDP CGTYPPGNPD LNLVEQHLPG YLDFLKKWFA ACYKQSLQNM RLVCEILGME   180
DLDYIGKKFE PRHMSTHSTW NYFLGQPVSQ LASGSSNRLN AHTDYCQFTM LFQDMVGGLE   240
LHDYEEDIYR PVPPIKGAMI VQVGDLLEKQ TNGRWRSALH RVTAPSRYMY GGSPGGDDEL   300
VQRYSLVFFG HLNLDEMIKP LPGCEKPGKW STLEWKDLMT AGQWLARRVA LEYERKTAAT   360
VM                                                                 362

SEQ ID NO: 26                   moltype = AA   length = 495
FEATURE                         Location/Qualifiers
source                          1..495
                                mol_type = protein
                                organism = Epichloe uncinata
SEQUENCE: 26
MASPGNHAIV APGWTRSEDG SLTRPLDLVE NWLLARIQRA NTPPGREAEG LTYKLKLRLP    60
QDIDDPIPYL RRAWLVFRYV QPLIGAIYPP YSERDETGRY LVTVPLMDPE EWLRLSFHVN   120
QGTQAVFRDV DDAGKIFQPR PTAMAYWFPP SSTLIIRSTH LRFDAVGIYK ATNTFMLGLE   180
SVFRLGLDAN LDCYTTDVKQ PSLPPGIDYI LGFPPQETPV PHRVERAVDE LMRHWHHGLY   240
SLSLPVREGS EDAAPANTQH LVTLFDEPTL EAIVAGCKKL GVSVSAAVHA SIVRVWASFP   300
QQQHTGARNM LIPLVANLRP LLDPKWVVPD YALGLCIFVV PFCLTGGFED LTQRLGAVYS   360
RDLSALPSDP AGDPVSFLEL LPLYESREAA FLGSLPVAGC PPFRVPNLSS LGVLERYLAR   420
AYGKKGAQAP VCEIEDVALV NATTDPTIEF QLFTFRGTMR LYLYYNDAYY TEDFLAPVME   480
MVRDSLLQEL GLGGS                                                   495

SEQ ID NO: 27                   moltype = AA   length = 506
FEATURE                         Location/Qualifiers
source                          1..506
                                mol_type = protein
                                organism = Epichloe uncinata
SEQUENCE: 27
MVSAGNHAIV ALGWTTSEDG TLTRPLDLVE NWLLARIQRA NTPPGREAEG LTYKLKLRLP    60
QDIDDPIPYL RRAWLVFRYV QPLIGAIYPP YSERDETGRY LVTVPPMDPE EWLRLSFHVN   120
QGSQAVFRDV DDAGMIFRPR PTAMAYWFPP SSTLVIRSTH LRFDAVGLYK ATNTFMLGLE   180
SVFRLGLDAN LDCYTTDVKQ PSLPPGIDYI LGFPPQETPV SHRVGCAVDE LMRHWHHGLY   240
SLSLPVREGS EDAAPANTQH MVTLFDEPTL EAIVAGCKEL GVSVSAAVHA SIVRVWASFP   300
QQQHTGARNM LIPLVANLRP LLDPKWVVPD YALSLCIFVV PFCLTGGFED LTQRLGAVYS   360
RDLSALPSDS AGDPVSFLEL LPLYDSQEAA FLGSLPVAGC PPFRVPNLSS LGVLERYLAR   420
AYGQKGAQAP VCEIEDVALV NATTDPTIEF QLFTFRGTMR LYLYYNDAYY TEDFLASVME   480
MVRESLLQEL GLDGSESSEG LDPKEA                                       506

SEQ ID NO: 28                   moltype = AA   length = 279
FEATURE                         Location/Qualifiers
source                          1..279
                                mol_type = protein
                                organism = Epichloe uncinata
SEQUENCE: 28
MTVNSSVKQE YDAQAAIYDG YMDRPSGVIE RQLFTAALGN CTGLTVLDLG GGTGLKAREA    60
ADAGASAVDV IDLSPEMMRV GRDAEQAGPR RGKDILRWYE GDVTRADLVE TLPGLRGPYD   120
LVIVGWTFDH AHDRAQLEAM WHNAVVRLKL GTGRLLVVRN GDPRSPAVTG GRYGIRYADH   180
```

```
VPIPGGFRFR DQMIRWGGGG QKQGKNPDQF EILADYECTA LEVMYSGSHE MYHQFGLTDI    240
RVQPYEETAA VRADPAFWAQ FLENPCLAVV TARKMGMVE                           279

SEQ ID NO: 29           moltype = AA  length = 578
FEATURE                 Location/Qualifiers
source                  1..578
                        mol_type = protein
                        organism = Epichloe uncinata
SEQUENCE: 29
MSNIRATIAG GARWQEVAAD CQQHRDATIA KIHPPIPDTQ ALESLFAGGD PRDVLSIPTL    60
VLTKGELAIT SANVEDLVPR LASGEWSAST VLKAFLRRAA LAQRLVNCVT EMLSETALKR    120
AAELDEHLAV HGKPIGPLHG VPISVKEHIA MKGLDVNGGY VSEVGRVAEE DALILGILRD    180
AGAIFYVRTT EPQSSMHLET SSSLYGETVN PFNTTLTSGG SSGGEGAIIA MRGSVLGVGS    240
DIGGSIRSPA HCNGIFGFKP TAGRLPTLGW FALMVGSEAI HATTGPLSTS IEGLWLFTKT    300
LLDAKPWLQD PSLTPMEWRD MSTAFAGRRL KVAVMWDDGV VKPHPPVTRA LKSVVEALKK    360
SEKIEVVDWK PWKHDLAWSI IAGLYFCDGG AQLNAAFEAA KEPLRPLSHW ILKENPHVKH    420
HSIASLWSAC AERDAYRLKY AELWNDTAKG GGGPVDVILC PAGPGAAPKL NTSRYWGYTA    480
QWNLLDYPAV VFPTGDIVSV EKDGAAGEQG GGDPASGADL DNWSLWTEHG AEGYSNAPLT    540
LQLVARRYDD EKLLHALEMV MKEAGLPTEL VGRSRGPA                           578

SEQ ID NO: 30           moltype = AA  length = 496
FEATURE                 Location/Qualifiers
source                  1..496
                        mol_type = protein
                        organism = Epichloe uncinata
SEQUENCE: 30
MDLTQFNTAG IVWPTVAAIA ISYILLSSFL SWYRLRHIPG PFLASISSLW NVLNIVTGRT    60
SPVLEKLPGK YGPLVRTGPN YVLTDDAEIL RHVNGARSTY PRNGWYEGFK VDEHDHMGSH    120
IDTSVHDAIK SKVIGGYNGK DGIDLEGAIG SQVKTLVSEI RRRHLGQPVD FSRLMRQMAL    180
DAITAVAFGE ALGFLTAEDG DVFGYVSAVD KMLTYLTLAS DLPVVRSVVR SRRMAPAVRC    240
VLAYTGIGRM LNHTRRVVAE RYAADDPGKG DMTASFIRKG LTQIECEGES HLQLIAGADT    300
AVTVLRSTLL YIMTTPRVYT RLKAEIKAAV DAGEVVEVIT MAQAQRLPYL QAVVLEGFRM    360
RPAVVYGHFK SVPAGGDTLP NGVRLPAGTA IAPNYIALTR RADVYGADVD LFRPERFLDA    420
EPAKRHEMER AMDLNFGLGR WQCAGRNIAL MEMNKVFFEL LRHFDLQILY PGKAWDEYTG    480
VVYSQHNMWV QITESS                                                   496

SEQ ID NO: 31           moltype = DNA  length = 1808
FEATURE                 Location/Qualifiers
source                  1..1808
                        mol_type = unassigned DNA
                        organism = Epichloe festucae
SEQUENCE: 31
atgacagtag atacgattac ttcgacttct aacgggaacc aagatgttcc aaaggaattc    60
ttcctaaaag aattcgaaac tcagcttctc catgttgggt aggttatcgc gcctcatatg    120
acggtcctct atcccaaaac taatcagttt tcggttcaag ccggttcccg gacatttag    180
gcagttgcgc ggtgcctgta tacagttcgg cagtaagatc aagccatcgc ctcctcgaaa    240
cccaccaact atgccacatg cactgacctt ttttttgcgc at cttaataggc             300
ctttgagttc aacagcgttg cccacggtgc gcgtcttcta aacttgacgc agttcggcaa    360
catctacagc cgcttcacca atgtttgtct ctttctcctc ctcccatg actgcttttc      420
cccaacgagg acacaagcta ataaaacaca accaacccct cacagcccac cgtcaatgta    480
ttgcaaaatc gactggccgg actggaagga ggcgtcgtc cttgtgccgt cgcatccggt     540
tctgctgctg tagtcgtgac ggtaatggcc ctcgcaggcg ttggcgacaa cttcgtctca    600
tccttcacg ttcatgctgg cactttccac cagttcgaga gttagccaa gcagatgggc      660
atcgagtgcc gctttgtgaa gtctcgagac cctgcagact ttgcggcggc catcgacgac    720
aagaccaagt tcgtctggct tgagaccatc agcaacccgtc gcaacgtaat actagaccct   780
gaggcagtct cgatggtctg ccacaccaag ggcattcctt tgattgttag tatcccaatg    840
aatactgtcc gtcccatagg ggggttgggg ctaaaattag gggggatggg gttcccatcc    900
aagatttag tgcgataaca cctttggctg tgccgggtac ttttgtcgtc ccatcaacca     960
cggcgtcgat atcgtcgttc actcggccac caagtggatc ggcggccacg gcactacggt    1020
aggcgtatc atcgtcgacg gcggtacctt tgactgggcg cagcaccccg atcggttccc    1080
ccagttccat gatccacgga cgcgactctg ggaacgcttt tccgtcggg cgtttgctgt      1140
ccgctgccag tttgagatcc tgcgtgatac ggggagcacc ctcagcgctc ctgcggccca    1200
gcagctgctg gttggcctcg aatcccttgc cgtgcgatgc gagcgccacg cgcagaatgc    1260
ggccaagatt gctgactggc tgcgtgaagca tcccctgggtca gctatgttgg             1320
tcacccgaac caccccgatt accagggagc gctcaagtac ctcaagcgag gctttgctc     1380
ggtcatctgt tttggtctac ggggggggttt cgaggcaggt gccctgttct gcgatgcgtt    1440
gaagatggtc atcaccacta ccaagtgcgt aattaaacta gcccttctt ctcccgagag      1500
agcatcgttc tgccattcta acctcgcttt gcagcctggg gatgccaag accctgatcc     1560
tccatcccgc ctcgactact catgagcact tcaggtccga acatcgagct gggctggcg     1620
tcacagatga tatgatcagg ctgtctgtgg gtattgagca gatcaatgat atcaaggccg    1680
acttcgagca ggccttgag caagtgcttc ggggtaagaa gagtcttcgt aagcttgca      1740
tcggaaagat tctcttgcag gatgagatca tgaagactt atttggacct tcagcttgtc    1800
gtacgtaa                                                            1808

SEQ ID NO: 32           moltype = DNA  length = 1516
FEATURE                 Location/Qualifiers
source                  1..1516
                        mol_type = unassigned DNA
                        organism = Epichloe festucae
```

SEQUENCE: 32
```
atggccacag ccgtacgaga agcatttgag aaccatgtca agctggtcga gagtcggaac   60
tcgcccggcc atgtgcttgc ttcttctgag gcctccttct ttgttgccga cttgaacgac  120
gttgttcgta agtgggcggc gtggaaggaa gctctcccag atgccacccc ttttttttggt  180
acgtcttcaa ttccccccccc catttcatgt ctcactaagc tggaagtcc cgtccgagga  240
tccgaatcaa ttgacttgga ggcagccgtg aaaagcagct atgatcgacg gctgatccga  300
actctggcca cctgtggagc cggatttgac tgtgcctcgg cagaggagat tgagttgacc  360
ctgtccttgg gcattggcgc agaacgaatc atcttcactc acccgtgcaa gcccgtctcc  420
tccctcgggc tgtgccgcaa gcttgggatc acgctcatca ctttcgacaa tgaatgtgag  480
ctccgtaagc tccaccatca ctatcccgaa gctcagaccg tcctccgcat tttcgccgac  540
gacccaacca atgccgatcc tttgggtacc aagtttggcg ccgcgcggaa cgactttgat  600
ggactcgtcc gtctggttaa ggagttgaac atgcagctgg ccggcgccag ctttcatgca  660
ggtgcgtctc gctcccggta ccttggctgc atgcagctag ctaacggcgg caattccacg  720
ccctgttcta gccccctagcg tcgccgtcga tgcagctgca tacgtacggg gcatccggga  780
cgcagctgag gtcttcgcgc gggcccgcca ggtcggggctg aaccctacgg tgctggatat  840
cggcggcggc tacactgact cgacgtttca acagattgca ggggcggtca ggccggcgat  900
tgccgagtgc ttcacgtcgc aagtgggcga gggacgcctg cgcatccttg cggagccggg  960
gactctcttc tcctgcagcc cgttctatct agcagtcaag gttgtcgcgc ggagggtgaa 1020
cgccactgcg tttgggcatg agccagccac gcgtctctac atcaacgacg gcatctacag 1080
caacttcatg atgcgtttca tcgtcaacat gaccttctcg cccacggccg tcatccggga 1140
gggtgtgtgt cacgatcagg cggatcatac gatgcgcggc gaggcgtgct ctcttttggg 1200
tcggagctgc gactccaacg actgtatcaa cagggattgc cggcttggta tgaaagtggg 1260
ggtcggggac tggcttgtct tcaaagacat gggggggtgag cgtttcccct tttcccttt 1320
ttcctttttcg tttttgggtc cctgtggagg agagtggcat acatgtatgt aggagctaac 1380
catgcatggt gtggcagcct acacaacggt atgcaacacc accttcaatg gcttcaccag 1440
ctccaaccac acaattacc tggaacccac ccaagtcgac aaagcccagt cgacctttga 1500
acagttggcc atctga                                                 1516
```
SEQ ID NO: 33      moltype = DNA   length = 1748
FEATURE            Location/Qualifiers
source             1..1748
                   mol_type = unassigned DNA
                   organism = Epichloe festucae SEQUENCE: 33
```
atgacattga ccaatttgga cgtaatcgtc gttggcgctg gtttttcagg tattctcgct   60
gcccacaggt gagtctacgt tgccatccaa gacacgaata gagtagagag gtaggactga  120
actatgacta aagactgcga aagctcggat ttcgagtcca agggttggag cgccaggaac  180
gtcttggagg tgtctggcgc gagaacgctt atccgggagc agcagtcgac agcctgtttc  240
ccttctacca gttctatgat gcggagcttc tccaagattg gaatggggga gagcaatttc  300
ccacccgtgc agagatgctc agatattttg accacgtgga caagcgatgg gaaatctcta  360
ctagtttga gtttggcgtt tcggtttccg cggcccggta tcggaaaact acccagagat  420
ggaccgtctc tttagaagat ggcagaagag ccgaggcgca atggttcatt ccagctgtag  480
gtgttttcgtc cgttctcaat atccccaaga ttccaggaat gtctcgattc cggcgtccga  540
tctaccacac cgcaaaatgg cctcatgacg ctgtcagtat gcgcggtaag agggtggctg  600
tcatcggaac ggggccaagc ggagttcaga tcatccaagc tgtgggtaag atagccaagg  660
ccatgacgat atttcagcag tctccatgcc tcactctacg caagtacggc agcccgagcc  720
agacgcaaag ggcactttgc atgagacccg acgaccaag agaagccta cgacttggac  780
tgcagacttc gaacggtttc ggctacgtga tccgtgacca ggacacgctg gatgttcaa  840
tagaggagcg aaaccatttt tatcagcagc gctatcggc gggaggctgg gctttctgga  900
tggctggggtt ccgggatctg tgccagaaca tccaagccaa ccgagatgcg tatgatttct  960
gggctcggcg gacacgagcg agaatcagcg atgtgaccaa acgggagctc ctggtgccca 1020
agattccacc ttttgccttt ggtatcaagc gaccctgttt ggaagaggat ctttacgagg 1080
tcatgaccac accccatgtg aaggttattg acatcagcaa ccagcaaatc gagttaatta 1140
cagagacagg tatccgcgtt catgggcaga cagttgaatg cgaagccatc attttttgcca 1200
ccgggtttgg cgacgaggca agcgggctca ggagtcttca tatcagaggc cggaaatggca 1260
tccgtttaga agatgcctgg tccgatggtg tcgagtcgca tctcggaatg gccattcatt 1320
cattccccaa catgttcttc ctctatggac cccagtgtcc tacacttctg gtcaactccc 1380
ccgcggtcat cactgttcag gtagagtggt tgtgcgaaat catctcaagg tgccaacagg 1440
cgggcatttta tcaacttgag gcgacttcca gtcccactg ccagtgggag aagagatga 1500
gcctactttg ggacaagaca ctctaccata cacatgcacg caaaagcaag acaacagctg 1560
cggctaacaa ggaagagaaa acttggtagg ttgcacaagg gctcttgtcg ctttgttctg 1620
tggactgctc taacaaaaccg gccagggttg gggggttgat tctgtatcgt cgcgagctgg 1680
aaaactgtct ggctaacaac ctggaggggt tcaagcatg gcatgtagag gaggcggctc 1740
ttctgtga                                                         1748
```
SEQ ID NO: 34      moltype = DNA   length = 698
FEATURE            Location/Qualifiers
source             1..698
                   mol_type = unassigned DNA
                   organism = Epichloe festucae SEQUENCE: 34
```
atgctcgatg aaagcccgat gcggaagggt gattctgtga gcaacgacca aggcaacccg   60
gagagcaatg catctgtttc aatccatcag cagaatcaaa tcatcacctg tgtctcccca  120
gacccagtct gccccaatgc gatacgaatc aagcgtgaca ttgtgatcgt gagactgcgg  180
cccgtcgaaa gttgtccagg ctatcgcttc tttcgccgag tctttgagac actagagaaa  240
tggcagctgc aagtcgacat gttctcaacc agtctgggc gaataaccct ggcgctgggg  300
gccgcagcgc tgcaagccgg cattggtgac tcatgcagtg ccagaaacga catgatgagc  360
cgggatctca tgcacggcat gcagaagctg ctcccgacg atcacataga gctctttcct  420
cacatgacca tcatctcggt cgttgaacac ccgagccgac gaatggccgg ccacatcttc  480
```

```
gccaccatgg atgccaatga tattcccacg gtcatgattt cgcacggtat ggcctcaatc    540
ctttcccgtt tccatagcaa ataatcgtcc cattgttctg accagcatgt tcagacgccg    600
ccaggctcgg tatagcctgt gccatctcgg agcagtacac tgctaaagct ttgtgcgtct    660
tcgagcaatg cttattccgg tactccttga cacattga                            698

SEQ ID NO: 35              moltype = DNA   length = 1518
FEATURE                    Location/Qualifiers
source                     1..1518
                           mol_type = unassigned DNA
                           organism = Epichloe festucae
SEQUENCE: 35
atgacagtga acagcaagcg tatcccattc ggcaagccta tgctggaggc tttctgcatg     60
gatccggaat acaccaacct caattcttgt cagttgctcg tcacacgatg tgcccgtttc    120
agtttccatg tgactgtatc tgaactaaca cgatgtggtc gtagcatctt gtgggtcgtg    180
gcccaaggtg gtgagcaagc agatcagaga ttactggtcc ctgctggagg cccagcccga    240
cttgttctcc gagttttccc aaggcttggt gctgcaggag gcacgtctcg gcctcgctcg    300
tctcgttcac gccgccgtct cggagtgcgt cctcgtctcc aacgtcacta ctggtatctt    360
caccgtcctt tacaaccagg catttgagga acgagacgtc gtggtgactc tatcaactac    420
ttacggtgcc atcgaccatg gcatcacttc cttggccgag gcggggccct tcaaaacacg    480
tagggtggag tttgagctcc ccacgacggg cgaaaagatt gtgtctcggt ttgagactac    540
catgcccaa atcagggctg agggtctacg cccgcgccta gcaattctag agacgatagt     600
gagcatcccct gctgttagga tgccgtttga agacttgctg gcgtatgcc agaaggaagg    660
catcatgacg ttggtcgacg gggcgcatag cgtgggccag tttgaggtca atctccagga    720
gctgcagccc gacttcttcg tctctgattg ccacaagtat gcagatccaa cgtcacgcac    780
gcccttgtaa tacggtgatt ccatgctgat actctacgat ttcactttac taggtggcta    840
tttgttcctc gaccttgtgc tttcttatac gttgccgagc gcaaccagca catgatgcgc    900
tccgccatcc cgacctcttt cggatttatt cccaagaatg gcaactcctg acttccccta    960
tggtcgcaga tggtcagtgc cagcgaaacg gcgtcttcgt tcgagacact gttcgcctac   1020
acagccacga gcgataacat gccccatctg tgcatcccga ccgccctccg cttcaggcgg   1080
gacgtctgtg gtggcgagac ggcaatttat gagtatataa agtggctcgc tacagagggt   1140
ggtgacaagg tcgccaatat tcttcagaca gaggtcttgg aggagcctag tctcggggcc   1200
ggggtagatg ccagatgag agactgcggc atcgtgacag tgcgactccc tttgccatt    1260
gccacgggcc cgtccactgc cccagctcac gtgccgatgc cgggcggcgc tctgacggag   1320
aaagaggtcg gcccagcagt tcgttacttg acaaaggctc tggcggaaag atacaagacc   1380
tggataccca tcatcgacta ccgcggatgg atatgggcta gactctgtgc gcaagtacac   1440
ttggaggtca gtgattttga gatggccggc aatgctctca agggaatatg cgaagagata   1500
ctcagcaggg agaggtga                                                 1518

SEQ ID NO: 36              moltype = DNA   length = 853
FEATURE                    Location/Qualifiers
source                     1..853
                           mol_type = unassigned DNA
                           organism = Epichloe festucae
SEQUENCE: 36
atgatcgctg cttcttcccc tcactcaggc gtcgtctctg cagaggacat cgaatttac      60
caagccaacg gatatcttcg cttgcccaa gaggctcacg gccgttcga cgacttggca     120
aagctggcag tatgggtggc aaaaatctcc cagtggggcc tggaaacagg gaaatggcga    180
cattattacg agacgacgaa tggcaagcat cttctctggg ggacggagaa gctcatggaa    240
tatcacgcgc ccatgcgaga cctgattgcc ggcgatgcac ctctcgcact gctcaagtcg    300
ctgacggca aagacatggt ggtcttcaag gacgagatag ggtggaaact cccaggcggg     360
aaggggcggg tccctcacct cgaccggccc gcgtactcca tgtttgcccc cgagttcatc    420
gagatcatga tcgccgtcga tgcccatacg gtcgagaatg gttgtttgca atttgtgcca    480
ggctctcaca aggaggcagt cccgatctcg gccgacggcc gcattgcatc ggcgtggcta    540
gagggcaagg aattcatccc catggtcctc gatccgggcg acgtcttgat cttcaacgag    600
agcatggccc atcggttgga gcctaacaag acggaccaaa gacgtgcagc tgtctttgcc    660
acctaccact ttgacctgtc ccagcccgac ctgcgggaca aattctacgc ccaccgctc    720
atccacagcc ccccggaaaa cggtaaggct tttccttggc cagatgatat ttgcatgttt    780
ggaggccaat gctaacatga tgcgtgacca atctcacgta gcctggggttg aaacagtggg   840
agcgcagact tga                                                       853

SEQ ID NO: 37              moltype = DNA   length = 1184
FEATURE                    Location/Qualifiers
source                     1..1184
                           mol_type = unassigned DNA
                           organism = Epichloe festucae
SEQUENCE: 37
atgacggtaa caaacaagcc tgttaagcct gctaatgtgc cagtgatgga ctttgaggca     60
atccatgcca gtgtcgggaa tgagcgcaag aaatacttgc gacagctcga cgaggcatgg    120
agccatcacg gagccatcta cgttattaat cacagtattg gcactgagac gtcgaggaa    180
gcattcgcct gggtaagtag ctggcctggt tactcaagaa tgggctggca ttcctcatgc    240
aagttaggag cgctaaatga tcttgtgtgc cttttgaaat gcagtgcaag aagttttttg    300
acctgcctct ggcggtcaag aactcggttc acatcccacc tgacgtatcc aagcattcc    360
agggctggac gggcacaggt gaggccatct cctcgcaggg cgtctgggat cccgacgaga    420
tcgagaggct ccgcaaggag atgccgacgg agctcaaagg cgcatggagc ctgcaggacc   480
cttgcggaac gtaccccccg ggcctcccag atctaaactt ggtggagcag catctcccgg    540
gctatctcga cttcttgaag aagtggttcg cggcctgcta caggcaatct ctccagaaca    600
tgcggctcgt gtgcgaaatc ctcgggatgg aggatttgga ttacattgga aaaaagtttg    660
cgccgcgcca catgagcacc cactcaacct ggaactactt cctcggggcag cccgttcac     720
agctggccag gggatccgcg aaccggctca acgcgcatac ggactactgc cagttcacca    780
```

```
tgctcttcca ggacatggtc ggggggcttg agctgcacga ctacgaggaa gacatttatc    840
gacctgtgcc tccgatcaag ggggctatga ttgttcaagt tggggacctg cttgagaagc    900
agaccaacgg cagatggcgg agcgccctcc accgcgtcac ggcgccgagc cggtacatgt    960
acgaaggaag tgccggtgac aatgacgagc tggtgcagcg ctactcgctc gtcttcttcg   1020
gacacttgaa tctggacgag atgatcgaac tctgccggtg ctgcgagaag ccaggaaagt   1080
ggagcacgct cgagtggaag gatcggatga cggcaggcga gtggctggcc cgccgagttg   1140
ctcttgagta tgagcgcaag aagacagcag caacggtcat gtag                    1184

SEQ ID NO: 38           moltype = DNA  length = 1491
FEATURE                 Location/Qualifiers
source                  1..1491
                        mol_type = unassigned DNA
                        organism = Epichloe festucae
SEQUENCE: 38
atggtcagtg cagggaattg tgccattgtc gctcccggat ggaccagatc agaagacggc     60
actctcactc gcccctcga cttggtggag aactggctgc ttgcccgtat tcaacgcgcc    120
aacacgcctc ctggtcgtga agccgagggc ctcacctaca agctcaaatt acgactgccc   180
cacgacattg atgacccat cccctacctc cgccgagctt ggcttgtttt tcgatatgtc    240
caaccgctca taggcgcaat ctatccgccc tattcagaac gagatgagac agggcggtac   300
ctggttacgg ttccccaat ggatcctgag gagtggctgc ggctaagttt ccacgtaaac    360
caagggagcc aggccgtttt cagggacgtg gacgatgccg aaagatctt tcgacctcgt   420
gaaacgcaa tggcctactg gttttccttcg tcgtcgaact tggttattcg cagcactcac   480
ctccgatttg acgctgtggg actatacaag gcgacaaaca ccttcatgct cggtcttgag   540
tcagtctttc gtctcggcct cgacgccaac ctatattgct acactaccga tgtcaaacaa   600
ccgtccctcc cgcccggcat cgactatatt ctggggttcc cgcccaggaa acacccgtc   660
tcacacgcg tggagcgtgc cgtcgatgag ctgatgcgac attggcatca tggtttgtac    720
agcttgtctc tccctgtgcg tgaggggtcc gaggacgctg cgcctgccaa cacccaaacc    780
ctggtgacct tattcgatga gccgacgctt gaggccatcg tggcgggttg caagaagctg    840
ggtgtgagcg tctcggccgc cgtgcacgcg agtattgtcc gcgtctgggc ctcattccct    900
caacagcagc acactggagc gcgcaacaac atgctcattc ccctcgtcgc gaacctgcgt    960
ccacttctgg accccaaatg ggtggttccg gactacgcac ttagcctctg tatctttgtc   1020
gtgccgttct gtctcacggg tggctttgag gacctcacgc aacgtctggg tgctgtttac   1080
tcgcgagatc tgtcggcgct gccctcagac ccggcaggcg accctgtgag cttttctcgag  1140
ttgctgccgc tgtatgacag cggggaggcc gcttttcctt tg gctccttgcc cgttgccggc   1200
tgtccgccct tccgggtacc caacctcagt agcctcggcg tgttggagag atatctagcg   1260
cgtgcgtacg ggaaaagggg ggcacaagcc cctgtttgtg agatcgaaga cgtagccctc   1320
gtcaatgcaa cgactgatcc aaccatcgag ttccagttat ttaccttccg cggcactatg   1380
cggctgtact tgtactacaa tgatgcatac tatacgaag actttctggc tcccgtcatg    1440
gagatggtgc gcgacagtct tctccaggag ctaggactcg tagaagtta g              1491

SEQ ID NO: 39           moltype = DNA  length = 840
FEATURE                 Location/Qualifiers
source                  1..840
                        mol_type = unassigned DNA
                        organism = Epichloe festucae
SEQUENCE: 39
atgacggtga atagcagcgt gaagcaggag tacgacgccc aagccgccat ctacgatggc     60
tacatggacc ggcccagcgg cgtgatcgag cggcagctct tcacggcagc actcggcaac    120
tgcacagggc tgacggtgct cgacctgggc ggcgggacgg ggctcaaggc gcgcgaggcg    180
gccgacgcag gagcgtcagc cgtcgacgtg atcgacctgt cgcccgagat gatgcgggtg    240
ggccaggtca cggagcaggc gggccctcgc cgcggaaaag acattctccg gtggtacgag    300
ggcgacgtga caagcgccga cctcgtcgag acgctgccgg gactccgcgg gccgtacgac    360
ctcgtcatcg tcggctggac cttcgaccac gcacacaacc gggcgcagct tgaggccatg    420
tggcacaacg ccgtggtgag gctcaagccc agcactggcc gcctgctcgt cgtccgcaac    480
ggcgatccgc gcagccctgc cgtcaccggc ggccgctcag gcatccgcta cgccggccat    540
gtacccatcc ccggcgggtt ccggttccgc gatcagatga ttcgttgggg aggcggcggc    600
caacagcagg ggacaaaacc cgaccagttc gagatcctcg ccgactacga gaccaccgcc    660
ctcgaggtca tgtactccgg ctcgcacgag atgtaccatc agttcggcct taccgacatc    720
cgcacccagc cctatgaaga gacggctgcc gtccgagccg accggccttt tgggcccag    780
ttcctcgaga acccgtgtct ggccgtcgtc acggcccgga agatgggcaa ggtggaatag    840

SEQ ID NO: 40           moltype = DNA  length = 1987
FEATURE                 Location/Qualifiers
source                  1..1987
                        mol_type = unassigned DNA
                        organism = Epichloe festucae
SEQUENCE: 40
atgtcgaaca tgagagctac gattgcgggg ggtgcgcggt ggcaagaggt agcagcagac     60
tgccaacagc atcgcgatgc gactgttacc aaaatcgacc ctcccattcc agatacacaa    120
gcactggaga gccttttcgc aagcggtgat ccgcgcgacg tctcgagcat tccaactctc    180
gtcctcagcg aggggggaact tgccatcacg tcggccaatg tcgaggatct tgttcccagg    240
ctggccagcg gagagtggag cgccagcacg gttttgaagg ccttcttgcg cagggcggcg    300
ctagcccagc ggctcgtgaa ttgcgtgaca gagatgcttt cagaaacggc cttgaagaga    360
gcagcagaac tggatgagca ccttgcggtc cacgggaagc ccattgcccc actccacggc    420
gtccccatca cgtcaaagaa gcacatcgct atgaaaggat tggacgtcaa tggtggctac    480
gtatccgagg ttgggcgcgt tgctgaggaa gatgcgctga tcttgaacat cctccggat    540
gcgggcgcca tcttctacgt taggacaaca gagccacagt catcaatgca cctggagacg    600
agtagcagtc tctatggggtg agtcatacgc ggcaatttgg cgtctacttg acaaacaatc    660
gactaaccat tggacagaga gactgtgaac cccttaaca ccaccctcac atcgggcggg    720
```

```
tcttcgggcg gagagggcgc catcatcgcc atgcgaggct cggtgctagg ggtcggcagt   780
gacatcgggg gaagcatccg ctcaccagcg cattgtaacg gcatcttcgg gttcaagcct   840
actaccggac gtctacccac cctcggatgg ttcgcgctca tggtgggctc tgaggctatc   900
cacgcaacta ctggtcccct ctctaccagc atagaaggtc ttcggctgtt taccaaaaca   960
ctgttggacg cgaagccatg gctccaggac cccagcctga cacccatgga tggagagat   1020
atgtccacgg cctttgccgg gcgaagactg aaggtcgcgg tgatgtggga cgatggcgtc  1080
gttaagccgc atccgcccgt cacgcgggct ttgaaaagcg tggtgaaaga tttgaagaag  1140
agcgagaaga ttgaggtggt ggactggtga ggactattct aggggaatca ccccttttt   1200
ccctccccc cttgtcattc catcgtcggc ccgcaagtct ttgcttctcg tcggtctggc   1260
gcccccaaaa caacgagcgg gcaacatcaa gtcagactaa cggctgatat tcttgtagga  1320
aaccatggaa acacgacctt gcctggtcca tcattgtaag ctgctccaca aagtcacctt  1380
tcaccttccc gactaaggca taagtgatta ggcaggcttg tacttttgcg acggcggtgc  1440
tcagctaaac gctgcgtttg aagcagccaa ggaaccgctg cggccgcttt cacactggat  1500
tttgaaggag aacccccacg tcaagcatca ctccataggc tcactgtgga gtgcgtgcgc  1560
cgagagagac gcataccgtc tcaaatatgc cgagctctgg aacgacactg caaagggggg  1620
gggcgggcca gtgacgtgga tcctgtgccc ggccgggcca ggagcggcgc ccaaactcaa  1680
tacttcgcga tattgggggtt atacggcaca gtggaaccta ctggactatc cggccgtcgt  1740
gttccccacg ggtgatatcg tcagcgtcga gaaggatggc gcgggggcg agcagggagg  1800
cggcgacccg gccagtggtg ccgacctgga caattggagt ctatggacag agcatggggc  1860
tgaagggtac agcaatgcgc ccctcgcttt gcagctcgta gctcgcagat gtgacgacga  1920
aaagctcctg cacgctttag agatggtaat gaaggaggct ggactagcca cggagctcgt  1980
tggatga                                                             1987

SEQ ID NO: 41          moltype = DNA   length = 1818
FEATURE                Location/Qualifiers
source                 1..1818
                       mol_type = unassigned DNA
                       organism = Epichloe festucae
SEQUENCE: 41
atggatctga ctcaattcaa aacagcgggc atcgtttggc cgacggttgc tgccatggcc    60
atatcctata tcctgctgtc gagctttctc tcttggtaca ggctacggca catccccggc   120
ccgttcctgg cctcgatctc aagtctttgg aatgttctaa acatcgtgac tgggcgcacg   180
tcgcctgtgc tcgagaaact gccaggaaag tacggcccga tggtgcgaac cggccccaac   240
tacgttctta cagatgatgc cgaaattttg cgtcacgtta atggcgctcg cagcacatac   300
ccccgtaatg ggtgtaagtc tgtccatatc acatgtcttt tgaaatgtag ggagactcag   360
agactcactc acactgtggc ttccagggta tgaaggcttc aaggtcgatg aacacgacca   420
tatgggggtcc catatcgaca cgtcggtaca tgacgccatc aaaagcaagg tgattggggg   480
gtacaacggc aaggatggga tagacctcga ggggccatc ggatcgcagg tcaagaccct   540
ggtcagtgag atccggcgcc gtcacctagg gcaacctgtc gacttctctc gtctgatgcg   600
tcagatggcg ctcgacgcca tcaccgccgt agcttttggc gaggccctcg ggttcctgac   660
ggccgaagac ggagacgtgt tcggctatgt cagcgccgtt gacaagatgc tgacctacct   720
gacacttgcc agcgacctgc ccatagtgcg cagctttgtc cgttcacgcc gcatggcgcc   780
ggccggtgcgt tgcgtcctgg cctatactgg catcggccgc atgctcaacc atacacgccg   840
ggtggtggcg gagcgctacg cggccgacga ccccggggaag ggcgacatga cggcctcatt   900
cattcgcaag gggctcacgc agatcgagtc cgagggcgag agccacctgc agctcatcgc   960
cggcgccgac actgccgtca cggtgctgcg ctccacgctg ctgtacatca tgacgacgcc  1020
gcgcgtgtac acgcggctca aggccgagat caaggccgtg gtggatgccg gcgaggtggt  1080
cgaggtcatc accatggccc aggcccaggg gctgccgtat ctgcaggctg tcgtgctcga  1140
gggcttccgc atgcgcccgg ccgtcgtgta cgggcacttc aagtcggtgc cggccggcgg  1200
cgatacgctg ccgaatggtg tacgcctgcc tgccggcact gccatcgccc caactatat   1260
agcactgacc cggcgaaccg acgtctatgg cgctgatgtc gatttgttcc gagcccgagcg  1320
tttcctcgac gccgagccgg ccaagcgcca cgagatggag cgcgccatgg acctgaattt  1380
cgggcttggc cgctggcagt gcgctggcag gaacattgct ctcatggaaa tgaataaggt  1440
tttcttcgag gtcggtggat gtgcatctcc gtctcttttgc ttcggttctt ttttcctgcc  1500
attgccctcg ccctccttgg ctatcctgac gcaggcgagg tatgagacga gatgagagac  1560
tgattcaatg cgcagttatt acgccacttc gacctccaga tcgtgtatcc aggcaaagca  1620
tgggatgaat acacgtaagg ccttctgaac ccttttttt tttttttttt tttcccacc   1680
tttcgcgcat atgcgtctcg ggtggcgtga gcagcatgcc atggatattg gagtgctaac  1740
caggttactt cttaacctctg caggggcgtg gtatattcgc agcataacat gtgggtacaa  1800
atcacggaga gctcgtga                                                 1818

SEQ ID NO: 42          moltype = DNA   length = 2055
FEATURE                Location/Qualifiers
source                 1..2055
                       mol_type = unassigned DNA
                       organism = Epichloe uncinata
SEQUENCE: 42
agaacaagtt ggcgattttc caacttggtt actcacccaa gccgtcactc tgttcatatc    60
attactcgcc ttccagtgtc ttgcccacct tgtttcaata ttgtcgtcga gcaaaatgac   120
agtagatacg attacttcga cttctaacgg gaaccaagat gttccaaagg agttcttccc   180
aaaagaattc gaaactcagc ttctccatgt tgggtaggtt atcgcgcctc atatgacggt   240
cctctatccc agaactaatc agtttgcgat tcaagccggt tcccgacat tttaggcagt   300
tgcgcggtgc ctgtatacag ttcggcagta agatcaagcc accgcctcct cgaaacccac   360
caactatgcc acatgtactg aattcttttc ccttttgcta catcttgata ggcctttgag   420
ttcaacagcg ttgcccacgg tgcgcgtctt ctaaacttga cgcagttcgg caacatctac   480
agccgcttca ccaatgtttg tctctttctc cttctccctc atgactgctt ttttaacgag   540
gacacaagct aataaaacaa aaccatcctt caacagccca ccgtcaatgt attgcaaaat   600
cgactggccg ggctggaagg aggcgtcgct gcttgtgccg tcgcatccgg ctctgcgcg   660
gtagtcgtga cggtaatggc cctcgcaggc gttggcgaca cttcgtgtc atccttcac   720
```

```
gttcatgctg gcactttcca ccagttcgag agtttagcca agcagatggg catcgagtgc   780
cgctttgtga agtctcgaga ccctgcagac tttgcggcgg ccatcgacga caagaccaag   840
ttcgtctggc ttgagaccat cagcaaccct ggcaacgtaa tactagacct tgaggcagtc   900
tcgatggtct gccacaccaa gggcattcct ttgattgtta gtatcccaat gaaaactgtc   960
cgtcccatag gggggggttgg ggctaaaatt cgggggggttg tggttcccat ccaagatttt  1020
agtgcgataa cacctttggc tgtgccgggt acttttgtcg tcccatcaac cacggcgtcg  1080
atatcgtcgt tcactcggcc accaagtgga tcggcggcca cggcactacg gtaggcggtg  1140
tcatcgtcga cggcggtacc tttgactggg gccagcaccc ggatcggttc ccccagttcc  1200
atgatccacg gacgcgactc tgggaacgct ttcccgtcg ggcgtttgct gtccgctgc   1260
agtttgagat cctgcgcgat acggggagca ccctcagcgc tcctgcggcc cagcagctgc  1320
tggttggcct cgaatccctt gccgtgcgct gcgagcgcca cgcgcagaat gcggccaaga  1380
ttgccgactg gctgcgtgag catccctcg tggcctgggt cagctatgtt ggtcacccga   1440
accaccccga tcaccaggga gcgctcaagt acctcaagcg aggctttggc tcggtcatct  1500
gctttggtct acggggggt ttcgaagcag gtgccctgct ctgcgatgcg ttgaagatgg  1560
tcatcaccac taccaagtgc gtaattaaac tagccccttc ttctcccgag agagcatcgt  1620
tctgccattc taacctcgct ttgcagcctg ggggatgcca agaccctgat cctccatccc  1680
gcctcgacta ctcatgagca cttcagttcc gagcatcgag ctgaggctgg cgtcacagat  1740
gatatgatca ggctgtctgt gggtattgag cagatcaagg atatcaaggc cgacttcgag  1800
caggcctttg agcaagtgct tcggggtaag aagagtcttc gtaagccttg catcggaaag  1860
attctcttgc aggatgagat caatgaagac ttatttggac cttcagcttg tcgtacgtaa  1920
ataggggtca ttgcgaggca tggtaaatgt tctaccagaa gtggcatgga agtattttcc  1980
aatagacctg taattcacgg ttgctacgtt ttttcatact taccatgcgg atttattttg  2040
ataatatttc tttaa                                                  2055

SEQ ID NO: 43        moltype = DNA   length = 1875
FEATURE              Location/Qualifiers
source               1..1875
                     mol_type = unassigned DNA
                     organism = Epichloe uncinata
SEQUENCE: 43
atgacagtag atacgattac ttcgacttct aacgggaacc aagatgtccc aaaggaattc    60
cttccaattg aattcgaaac tcagcttctt catcttgggt aggttatcgc atctcatatg   120
acggtcctct attccagaac taatcagttt gcgattcaag ccgattcccg acatttttag   180
gcagttgcgc agtgcctgta tacagttcgg cagtaagatc aagccaccgc ctcctcgaaa   240
cctaccaact atgcacatgt actgaattgt tttcttttt gcgcattctt aataggcctt    300
tgagttcaac agcgttgccc acggtgcgcg tcttctaaac ttgacgcagt tcggcaacat   360
ctacagccgc ttcaccaatg tttgtctctt tctccttctc ccgcatgact gcttttccct   420
gacgaggata caagctaata aaacacaacc atccttcaac agcccaccgt caatgtattg   480
caaaatcgac tggccgggct ggaaggaggc gtcgctgctt gtggcgtcgc atccggctct   540
gcggcggtag tcgtgacggt aatggccctc acaggcgttg gcgacaactt cgtctcatcc   600
tttcacgttc atgctggcac tttccaccag ttcgacagtt tagccaagca gatgggcatc   660
gagtgccgct tgtgaagtc tcgagaccct gcagactttg cggcggccat cgacgacaag    720
accaagtttg tctggcttga gaccatcagc aaccctggca acgtaatact agaccttgag   780
gcagtctcga cggtctgcca caccaagggc attcctttga ttgttagtat cccaatgaat   840
actgtccatc ccatagggg agttgggct aaaattaggg gggatgggggt ttccatccgg    900
gggattttag tgcgataaca ccctttggctg tgccgggtac ttttgtcgtc catcgacca    960
cggtgtcgat atcgtcgttc actcggccac caagtggatc ggcggccacg gcactacggt  1020
aggcggtatc atcgtcgacg gcggtacctt tgactggggc cagcaccgg atcgcttcc  1080
ccagttccat gatccacgga cgcgactctg ggaacgcttt cccgtcgggg cgtttgctgt  1140
ccgctgccag tttgagatcc tgcgcgatac ggggagcacc ctcagcgccc tgcggccca   1200
gcagctgctg gtaggcctcg aatcgcttgc cgtgcgctgc gagcgccacg cgcagaatgc  1260
ggccaagatt gccgactggc tgcgcgagta tcccctcgtg gcctgggtca gctatgttgg  1320
tcacccgaac caccccgatc accagggagc gctcaagtac ctcaagcgag gctttggctc  1380
ggtcatctgc ttcggtctac gggggggttt cgaagcaggt gccctgttct gcgatgcgtt  1440
gaagatggtc atcaccacta ccaagtgcgt aattaaacta gccccttctt tcctgcgag   1500
aacatcgttc tgccattcta acctcgcttt gcagcctggg ggatgccaag ccctaatcc   1560
tccatcccgc ctcgactact catgagcact tcagttccga gcatcgagct gaggctggcg  1620
tcacagatga tatgattagg ctgtctgtgg gtattgagca gatcaaggat atcaaggcc   1680
acttcgagca ggcctttaag caagtgcttc ggggtaaaaa gagtcttcgt aagccttgca  1740
tcggaaagat tctcatgcag gatgagatca atgaagactt atttggacct tcggcttgt   1800
gtacgtaaat aggggtcatt gcgaggcatg gtaagttttc ctaatagacc cgtaattcac  1860
ggttgttact ttttt                                                  1875

SEQ ID NO: 44        moltype = DNA   length = 1854
FEATURE              Location/Qualifiers
source               1..1854
                     mol_type = unassigned DNA
                     organism = Epichloe uncinata
SEQUENCE: 44
ttgccattgt attactccag aacacgtatc ttgcacaaac tccaatctca gcaatggcca    60
ccgtcgtacg agaagcattt gagaaccatg tcaagctggt cgagagtcgg aactcgcccg   120
gccatgtgct tgcttcttct gaggcctcct tctttgttgc cgacttgaac gacattgttc   180
gtaagtgggc ggcgtggaag aaagctctcc cggatgtcac ccctttttt ggtacgtcct    240
caattccccc catttcatgt ctcactaagc tgggaagtcc cgtccgaggg tccgaatcaa   300
ttgacttgga ggcagccgtg aaaagcagct acgatcgacg gctgatccag actctggcca   360
cctgtggagc cggatttgac tgtgcctcgg tggaggagat tgagttgatc ctctccttgg   420
gcattggcgc agaacgaatc gtcttcactc atccgtgcaa gcccgtctcc tccctcgggc   480
tttgccgcaa gcttgggatc acgctcatca cttttgacaa cgaatgcgag ctccgtaagc   540
tccaccatca ctatcccgag gctcagaccg tcctccgcgt cttcgccgac gacccaacca   600
```

-continued

```
atgccgatcc tttgggtacc aagtttggcg ccgcgcggga ggacattgat ggactcgtgc     660
gtctggtcaa ggagttgaac atgaagctgc ccgcgccag cttttcatgca ggtgcgtctc     720
gctctcggta cctcggccgg tgaaatgcat gcagctcgct aacggcggca attccacgcc     780
ctgttctagc ccctagcgtc gctgtcgacg cagctgcata cgtgcggggc atccgggacg     840
cagccgaggt cttcgcgcgg gcccgacggg tcgggttgaa ccctacggtg ctggatattg     900
gcggcggcta cacagactcg acgtttcaac agattgcagg ggcggtcagg ccggccatcg     960
ccgagtgctt caagtcgcaa gtggtcgagg gacgccttcg catccttgcg gagccgggga    1020
ctctcttctc ctgcagcccg ttctatctag cagtcaaggt tgtcgcgcgg aggaggaacg    1080
ccgctgcgtt tgggaatgag ccagccacgc gtctctacat caacgacggc atctacagca    1140
acttcatgat gcgtttcatc gtcaacatga ccttctcgcc cgtggccgtc atccggaagg    1200
gggtgtggta cgatcagacg gagcaaacga tgccgcgcga ggcgtgctct ctttggggcc    1260
ggagctgtga ctccaacgac tgcatcaaca gggattgccg gctcgatccg gaagtggggg    1320
tcggggactg gcttgtcttc aaagacatgg gtggtgagcg tctcaactttt tccccccttt    1380
tccttttcgt ttttgggtcc ctgtggagaa tagcatatgt aggagctaac catgcatggt    1440
gggcagccta cacaacggta tgtaacacca ccttcaatgg cttcaccagt tccaatcaca    1500
caatctacat tgaacccacc caagtcgaca aagcccagtc gacctttgaa cagttggagt    1560
tggccatctg agtgccagtt cggggagacc cacacgcggc acgtgccgtc ccgggttccc    1620
gggcgtggct gcatgacgct agacgcgcta gtctagtacc tactccgttc cgtactgtcc    1680
ttgcagcagt ccgtagtcac aacagatggc ttggatcaat tgatgcacac tccctgatta    1740
gcttgtttga cacattccat ttggcttcgt gcacatcatg atacaaccag tacatgtttc    1800
ctccagtcct tttgtacatg gccacgccga gctcttgtaa gtacctcgtc gagc          1854

SEQ ID NO: 45         moltype = DNA   length = 1555
FEATURE               Location/Qualifiers
source                1..1555
                      mol_type = unassigned DNA
                      organism = Epichloe uncinata
SEQUENCE: 45
ttgccattgt tttacttcag aacacgtatc ttgcacaatt ttcagtcgca gcaatgacga      60
cagtcgtacg agaagcattt gagaaccatg tcaagctgat cgagagtcgg aactcgcccg     120
gccatgtgct tgcttcttct gaggcctcct tctttgttgc cgacttgaac gacgtcgttc     180
gtaagtgggc ggcgtggaag gaagctctcc cagatgtcac ccctttttt ggtacgtctt      240
caattccccc ccatttcatg tctcactaag ctgggaagtc ccgtccgagg gtccgaatca     300
attgacttgg aaggcagccg t gaaaagcagc tatgatcgac ggctgatcca gactcctggcc    360
acctggag ccggatttga ctgtgcctcg acggaggaga ttgagttgat cctgtccttg       420
ggcattgggg cagaacgaat catcttcact catccgtgca agcccgtctc ctccctgggg     480
ctgtgccgca agcttgggat cacgctcatc acttttgaca acgaatgtga gcttcgtaag     540
ctccaccatc actatcccga ggctcagacc gtgctccgag tcttcgccga cgatccaacc     600
aatgccgatc ccttgggtac caagtttggc gccgcgcggg acgactttga tggactcgtc     660
cgtctggtta aggagttgaa catgcagctg gccggcgcca gctttcatgc aggtgcgtct     720
cgctctcggt atcttggccg gtaaaatgca tgcatacagc tcgctaacgg cggcaattcc     780
acacctgtt ccactgttcc agcccccagc gtcgctgtcg atgcagctgc atacgtacgg     840
ggcatccggg acacagccga ggtcttcgcg cggcccgcac aggtggggct gaaccctacg     900
gtgctggata tcggcggcgg ctacacggac tcgacgtttc aacagattgc aggggcggtc     960
aggccggcga ttgccgagtg cttcaagtcg aagtgggcg agggacgcct gcgcatcctt    1020
gcggagccgg ggactctctt ctcctgcagc ccgttctatc tagcagtcaa ggttgtcgcg    1080
cggagggtga acgccactgc gtttgggcat gagccagcca cgcgtctcta catcaacgac    1140
ggcatctaca gcaacttcat gatgcgtttc atcgtcaaca tgaccttctc gcccgcggcc    1200
gtcatccggg agggtgtgtg gcacgatcag gcggatcata cgatgcgcgg cgaggcgtgc    1260
tctctttggg gccggagctg cgactccaac gactgcatca cagggattg ccggctcggt    1320
ccggaagtga gggtcgggga ctggcttgtc ttcaaaagaca tgggggtga gcgttttccc    1380
ttttccccct gtgagaata gcatacatgt attagcatag gagctaacca tgcatggtgt    1440
ggcagcctac acaacggtat gcaacaccac cttcaatggc ttcaccagct ccaatcacac    1500
aatctacctg gaacctggaa cccacccaag tcgacgaagc ccagtcgacc tttga          1555

SEQ ID NO: 46         moltype = DNA   length = 1820
FEATURE               Location/Qualifiers
source                1..1820
                      mol_type = unassigned DNA
                      organism = Epichloe uncinata
SEQUENCE: 46
ttctgcatat gattatttaa ttcttcttca tttcactaag atgacattga ccaatttgga      60
cgtaatcgtc gttggcgctg gttttttcagg tattctcgct gtctacaggt gagagtctac     120
gttgccatcc aagacacgaa tagagtagag aggtaggact gaactatgac tacagactac     180
gaaagctcgg atttcgagtc caagggtttg agcgccagga acgtcttgga ggtgtctggc     240
gcgagaacgc ttatccggga gcagcagtcg acagcctgtt tcccttctac cagttctatg     300
atgcggagct ctctccaagat tgggaatggg tagagcaatt tcccacccgt gcagagatgc     360
tgagatattt tgaccacgtg gacaagcgat gggaaatctc tgctagtttt gagtttggcg     420
tttcggtttc cgcggcccgt tactcagaaa ctacccagaa atggaccgtc tctttagaag     480
atggcagaag agccgaggcg cgatggttca ttccagctgt agggttttcg tccgttctca     540
acatccccag gattccagga atgtctcgat tccgcggtcc catctaccac accgcaaaat     600
ggcctcatga cgctgtcagt atgcgcggta agagggtggc tgtcattgga acggggccaa     660
gcggagttca gatcatccaa tctgtgggta agatagccaa ggccatgacg atattccagc     720
agtctccatg cctcactcta cgcaaatacg gcagcccgga caggcacttt     780
gcatgagacc cgacgaccac agagaagccc tacgactttgg actgcagact tcaaacggtt     840
tcggctacgt gccccgtgac caggacacgt tggatgtccc aatagaggag cgaaccatt      900
tttatcaaca acgctatctg gcgggaggct gggcttctg gatggctggg ttccgggatc      960
tgtgccagaa catccaagcc aaccgggatg cgtatgattt ctgggctcgg cggacgcgag    1020
ctagaatcag cgatgtggcc aaacgggagc tcctggtgcc tcaaatttca tcttttgcct    1080
```

```
ttggtatcaa gcgaccctgt ttggaagagg atctttacga ggttatggac caaccccatg    1140
tgaaggttat tgacatcagc aaccagcaaa tcgagttaat tacagagaca ggtatccgcg    1200
ttcatgggca gacagttgaa tgcgaagcca taattcttgc caccgggttt ggcgacgagg    1260
caagcgggct caggagtctt catatcgagg ccggaatgg catccgttta gaagatgcct     1320
ggtccgatgg tgtcgagtcg catctcggaa tggccattca ttcattcccc aacatggtca    1380
tcctctatgg accccagtgc cctacacttc tggtcaactc ccccgcggtc atcaccgttc    1440
aggtagagtg gttgtgcgaa atcatcgcaa ggtgccaaca ggcgggcatt tgtcaactcg    1500
aggcgacttc caaatcccac tgccagtggg agaggaagat gagcctactt gggacaaga    1560
cactctacca tacacatgca cgcaaaagca agaaaacagc tgaggctaac aaggaagaga    1620
aaacttggta ggttgcacaa gggctcttgt cgctttgttc tgtggactgc tctaacaaac    1680
tgatcagggt tgggggttg attcgtatc gtcgggagct ggaaaactgt ctggccaaca     1740
acctggaggg gtttcaagcg tggcatgtag aggagacggg tcttctgtga agccactttc    1800
tgtcgtatat cgagtcgata                                               1820

SEQ ID NO: 47           moltype = DNA   length = 1776
FEATURE                 Location/Qualifiers
source                  1..1776
                        mol_type = unassigned DNA
                        organism = Epichloe uncinata
SEQUENCE: 47
ttcttcattt cactaagatg acattgacca atttggacgc aatcgtcgtt ggcgctggtt    60
tttcaggtat tctcgctgtc tacaggtgag tctacggtgc catccaagac acgaatagag    120
tagagaggta ggactgaact atgactacag actgcgaaag ctcggatttc gagtccaagg    180
gttcgagcgc caggaacgtc ttggaggtgt ctggcgcgag aacgcttatc cgggagcagc    240
agtcgacagc ctatttccct tctaccagtt ctatgatgca gagcttctcc aagattggga    300
atgggagag caatttccca cccgtgcaga gatgctcaga tattttgacc acgtggacaa     360
gcgatgggaa atctctgcta gttttgagtt tggtgtttcg gtttccgcgg cgaggtactc    420
agaaactacc cagagatgga ccgtcacttt agaagatggc agaagagccg aggcgcgatg    480
gttcattcca gctgtagggt tttcgtcggt tctcaatatc cctaggattc caggaatgtc    540
tcgattccgc ggtgccatct accacaccgc aaaatggcct catgacgctg tcagtatgcg    600
cggtaagaga gtggctgtca ttggaacggg gccaaggcga gttcagatca tccaatctgt    660
gggtaagata gccaaggcca tgacgatatt ccagcagtct ccatgcctca ctctacgcaa    720
gtacggcagc ccgaaccaga cggcaacggc actttgcatg agacccgacg accagagaga    780
agccctacga cttggactgc agacttcgaa acggttccgc tcgtgcccc gtgaccagga     840
cacgttggat gtcccaatag aggagcgaaa ccattttat caacacgtct atctggcgg     900
aggctgggct ttctgatgg ctgggttccg ggatctgtgc cagaacatcc aagccaaccg     960
ggatgcgtat gatttctggg ctcggcggac acgagctaga atcggcgatg tgaccaaacg    1020
ggagctcctg gtgcctcaga ttccatcttt tgcctttggc atcaagcgac cctgtttgga    1080
agaggatctt tacgagatca tggaccaacc acatgtgacc attattgaca tcagcaacca    1140
gcaaatcgag ttgattacag agacaagtat tcgcgttcat gggcagacag ttgaatgcga    1200
agcgatcatt tttgccaccg ggtttggtga cgaggcaagc gggctcagga gtcttcatat    1260
cagaggccgg aatggcatcc gtttagaaga tgcctggtcc gatggtgtcg agtcgcatct    1320
cggaatggcc atccattcat tccctaacat gttttcctc tatggcctac                1380
acttctggtc aactccccg cggtcatcac tgttcaggta gagtggttgt gcgaaatcat     1440
ctcaaagtgc caacaggcgg gcatttgtca actcgaggcg acttccaagt cccactgcca    1500
gtgggagaag aagatgagcc tactttggga caagacactc taccatacac atgcacgcaa    1560
aagcaagaaa acagctgagg ctaacaagga agagaaaact tggtaggttg cacaaaggct    1620
cttgtcgctt tgtactgtgg actgctctaa caaaccggtc agggtgggg ggttgattct     1680
gtatcgtcgg gagctggaaa actgtctggc caacaacctg gaggggtttc aagcatggta    1740
tgtagaggag acggctcttc tgtgaagcca ctttct                              1776

SEQ ID NO: 48           moltype = DNA   length = 843
FEATURE                 Location/Qualifiers
source                  1..843
                        mol_type = unassigned DNA
                        organism = Epichloe uncinata
SEQUENCE: 48
gtcagtgaca ccaaacccat tcagcccacc cacaaaatct caattcgact gtattttcta    60
acgatgctcg atgaaagccc aatgaggaag ggtgattctg tgagcaacga ccaaagcaac    120
ccggagagca atgcatctgt ttcaatccat cagcagaatc aaatcatcac ctgtgtctcc    180
ccaggcccag tctgcccaa tgcgatagaa atcaagcgtg acattgtgat cgtgagacta     240
cggcccgtcg aaagttgtcc aggctatcgc ttctttcgcc gagtctttga cacactagag    300
aaatggcagc tgcaagtcga catgttctca accagtctgg ggcgaataac cttggcgctg    360
ggggccgcag cgctgcaagc cggcattagt gactcatcga gtgccagaaa tgacatgatg    420
agccgggatc tcatgcacgg catgcagaag ctactcccgg acgatcacat agagctcttt    480
cctcacatgg ccatcatctc ggtcgttgga caccccgagcc gacgaatggc cggccacatc    540
ttcgccacca tggatgccaa tgatattccc acgtgcatga tttcgcacgg tatggcctca    600
atcctttccc gtttccatag caaatcatcg tcccattctt ctgaccagca tgttcagacg    660
ccgccaggct cggtatagcc tgtgccatct cggagcagta cactgctaaa gccttgtgcg    720
tcttcgagca atgcttattc cggtactcct tgacacattg aaccgttatc tcagtctctt    780
catcaaaact cttctcgttg cagaattaga tagattagat gcacaagaca ctcgttgtgg    840
gct                                                                 843

SEQ ID NO: 49           moltype = DNA   length = 944
FEATURE                 Location/Qualifiers
source                  1..944
                        mol_type = unassigned DNA
                        organism = Epichloe uncinata
SEQUENCE: 49
```

```
acggaacgtc agtaacacca aacccatcca gcccacccac aaaatctcaa ttgaactgta    60
ttttctaacg atgcttgatg aaagcccgat gcggaagggt aattctgtga gcaacgacca   120
aggcaaccca gagagcaatg catctgtttc aatccaccag cagaatcaga tcatcacctg   180
tgcctcccca ggtccagtct gccccaatgc cataggcatc aagcgtgaca ttgtggtcgt   240
gagactacgg cccgtcaaaa gttgtccaga ctatcgcttc tttcgccgag tctttgagac   300
actagagaaa tggcagctgc aagtcgacat gttctcaacc agtctggggc gaataaccttt  360
ggcgctgggg gccgcagcgc tgcaagccgg cattggtgac tcatgcagtg ccagaaatga   420
catgatgagc cgggatctca tgcacggcat gcagaagctg ctcccggacg atcacatatt   480
agagctcttt cctcacatgg ccatcatctc ggtcgttgga cacccgagcc gacgaattgc   540
tggccacatc ttcgccacca tggatgccaa tgatattctc acggtcatga tttcgcacgg   600
tatggcctca atcctttccc gtttccatag aaggtcatcg tcccactctt ctgaccagca   660
tgttcagacc ccgccaggct cggtatagcc tgtgtcatct cggagcagca cactgctaaa   720
gctttgggcg tcttcgagca atgcttattc cggtactcct tgacacattg aacagttatc   780
tcagtctctt catcaaaacg cttctcattg cagaatcata ttagatgcac aagacactcc   840
ttgtgggcta tggttttttt ggccgcgata gacagctaaa actaaattct cattgtagct   900
acaagcagct ttatcacttc ccgtgatact gactttttct tggc                    944

SEQ ID NO: 50          moltype = DNA  length = 1517
FEATURE                Location/Qualifiers
source                 1..1517
                       mol_type = unassigned DNA
                       organism = Epichloe uncinata
SEQUENCE: 50
atgacagtga acagcaagcg tatcccattc ggcaagccta tgctggaggc tttctgcatg    60
gatccggaat acaccaacct caattcttgt cagttgcccg tcacacgatg tgcccgtttc   120
aatttccatg ttgactgtat ctgaactaac aagacgtact cgtagcatct tgtgggtcat   180
ggcccaaggt ggtgagcaag cagatcagag attactggtc cctgctggag gcccagcccg   240
acttgttctc cgagttttcc caaggcttgg tgctgcagga ggcacgtatc ggcctcgctc   300
atctagttca tgccgccgtc tcggagtgcg tcctcgtctc caacgtcact actggtatct   360
tcaccgtcct ttacaaccag gcatttgagg aacgggacgt cgtggtgact ctatcaacta   420
cttacggtgc catcgaccat ggcatcactt ccttggccga gactcggccc ttcaagacac   480
gtagggtgga gtttgagctc cccacgacgg ccaaaagat tgtgtcccag tttgagactg   540
ccatggccca aatcagggct gacggtctac gcccgcgcct agcaattcta gagacgatag   600
tgagcatccc tgctgttagg atgccgttcg aagacttgct gcgcgtatgc cagaaggcag   660
gcatcatgac gttggtcgac ggggcgcata gcgtgggcca gttcgaggtc aatctccagg   720
agctgcagcc tgacttcttc gtctctgatt gccacaagta gcagatcca acgtcacaca   780
cgcccttaat acggcggttc catgctgata ctctacgcat tgatcttact aggtggttat   840
ttgttcctcg accttgtgct gtcctatacg ttgccgagcg caaccagcac atgatgcgct   900
ccgtcatccc gacctcttc ggatttattc ccaagaatgc cttcctctga cttccccgtt   960
ggtcgcagat ggtcagtgcc agcgaaacgc gtcttcgtt tgagacactg ttcgcctaca  1020
ctgccacgag cgattacatg cccatctgt gcatcccggc cgcctccgc ttcaggcgag   1080
acgtctgtgt ggcgaggcg gcaatttacg agtacataaa gtggctcgcg aaagagggtg   1140
gtgacaagat cgccgatatt cttcagacag aggtcttgga ggagcctgtg cttggggcgg   1200
gggtagatgg ccagatgaga aactgcggca tcgtgacagt gcgacttccc ttggccattg   1260
ccacggggccc gtccactgcc ccagctcatg tgccggggcgg cgctctgacg gagaaagagg  1320
tcggcccggc agttcgttac ttgacaaagg ctctggcgga aagatacaag acctggatac   1380
ccatcatcga ttaccgcgga tggatatggg ctagactctg tgcgcaagta tacttggagg   1440
tcagtgattt tgagatggcc ggcaattctc tcaaggtaat atgcgaagag atactcaaca   1500
gggagatggg acaatag                                                 1517

SEQ ID NO: 51          moltype = DNA  length = 1558
FEATURE                Location/Qualifiers
source                 1..1558
                       mol_type = unassigned DNA
                       organism = Epichloe uncinata
SEQUENCE: 51
ccttgtcaag atgacagtga atagcaagcg tatcccattt ggcaagccta tgctggaggc    60
tttctgcatg gatccggaat acaccaacct caattcttgt cagttgctca ttacacgatg   120
tgcccgtttc agtttccatg tgaaatgtat ctgaactaac aagacgtggt cgtagcatct   180
tgtgggtcat ggcccaaggt ggtgagcaag cagatcagag attactggag cctgctggag   240
gcccagcccg acttgttctc cgagttttac caaggcttgg tgctgcagga ggcacgtctc   300
ggccttgctc gtctcgttca cgccgccgtc tcggagtgcg tcctcgtctc caacgtcact   360
actggcatct tcacgtcct ttacaaccag gaatttgagg aacgagacgt tgtggtgact   420
ctatcaacta ccttacgtgc catcgaccat ggcataactt ccttggccga gactcggcca   480
ttcaaaacac gtagggtaga gtttgagctc cccacgactg gcgaaaagat tgtgtctcag   540
tttgagacta caatagctca aatcagggct aagggtctac gcccgcgcct agcaattcta   600
gagacgatag tgagcatccc tgctgttagg atgccgtttg aggacttgct gcgcgtatgc   660
cagaaggaat gcatcatgac attggtcgac ggggcgcaca gcgtgggcca gtttgaggtc   720
aatctccagg agctgcagcc tgacttcttc gtctctgatt gccacaagta gcggatcca   780
acgtctctcc acgcccttga tacggtggtc catgctgat cctctgcgca ttcactttac   840
taggtggcta tttgttcctc gaccttgtgc tttcttatac gttgccgagc gcaaccagca   900
catgatgcgc tccgccatcc cgacctcttt cggatttatt cccaagaatg caactctca   960
acttccccta tggtcgcaga tggtcagtgc aaacggaaca gcgtcttcat tcgagacact  1020
gtttgcctac acagcccgga gcgataacat gcccatcctg tgcatcccgg ccgcccctccg  1080
cttcaggcga gacgtctgtg tggcgaggcg gcaatttacg agtacatca agtggctcgc   1140
taaagagggt ggtgacaagg tcgccgagat acttcagaca gaggtcttgg aggagcctgg  1200
tctcggggcc ggggcggatg ccagatgag agactgcggc atcgtgacag tgcgacttcc   1260
cttgccattg ccacgggcc cgtccactgc cccagctcat gtgccgggcg gcgctctgac   1320
ggagaaagag gtcggcccgg cagttcgtta cttgacaaag gctctggcgg atagatacaa   1380
```

```
gacctggata cccatcgccg attgccgcgg atggatatgg gctagactct gtgcgcaagt   1440
atacttggag gtcagtgatt ttgagatggc cggcaatgct ctcaaggtaa tatgcgaaga   1500
gatactcagc agggagatgg gacaagagat ttcggactca tataggtggc acgactaa    1558

SEQ ID NO: 52           moltype = DNA   length = 852
FEATURE                 Location/Qualifiers
source                  1..852
                        mol_type = unassigned DNA
                        organism = Epichloe uncinata
SEQUENCE: 52
tcatgaccgc tgcttcttcc cctcacccag gcgtctctgc agaggacatc gaattctacc   60
aagccaacgg atatcttcgc ctgccccaag aggctcacgg cctgttcgac gacttggcaa   120
agttgcaggc atgggtggca gaaatctccc agtggggcct ggaaacgggg aaatggcgac   180
attactacga gacgacgaat ggcaagcatc ttctctgggg gacggagaag ctcatggaat   240
accacgcgcc catgcgagac ctgattgctg cgcaggcacc tctcacactg ctcaagtcgc   300
tgacgggcaa agacatggtg gtcttcaagg acgagatagg gtggaaactc ccaggcggga   360
aggggggcggt ccctcacctc gaccggcccg cgtactccat gtttgccccc gagttcatcg   420
agatcatgat cgccgtcgat cgcccatacg tcgaaaatgc ttgtttacag tttgtaccag   480
gctctcacaa ggaggcagtc ccgatttcgg ccgacggccg cattgcatcg gcgtggctag   540
agggcaagga gttcatcccc atggtcctcg atcccggcga cgtcttgatc ttcaacgaga   600
gcatggccca tcgttggat cctaacaaga cggaccaaag acgtgcagct gtcttttggca   660
cctaccactt tgaccggtcc cagcccgacc tgcgggacaa attctacgc caccggctca   720
tccacagccc cccagaaaac ggtaaggctt tccttggcc agatgatgtt tgcatgtttg   780
gaggccaatg ctaacatgat gcgtgaccaa tctcacgtag cctgggttga aacagtggaa   840
gcgcagactt ga                                                      852

SEQ ID NO: 53           moltype = DNA   length = 917
FEATURE                 Location/Qualifiers
source                  1..917
                        mol_type = unassigned DNA
                        organism = Epichloe uncinata
SEQUENCE: 53
aaagaacagt ccaacctacg agacaatcac ggtgaagccc tctgtttcct gtaatccatc   60
atgaccgctg cttcttcccc tcacccaggc gtctctgcag aggacatcga attctaccaa   120
gccaacggat atcttcgcct gccccaagag gctcacggtc tgttcgacga cttggcaaag   180
ctgcaggtat gggtggcaga aatctcccag tggggcctgg aaacgggaaa atggcgacat   240
tattacgaga caacgaatgg caagcatctt ctctggggga cggagaaact aatgaaatac   300
cacgcgccca tgcaagactt gatttctggc gaggcacctc tcgcactgct caagtcgctg   360
acgggcaaag acatggtggt cttcaaggac gagataggg ggaaactccc aggcgggaag   420
ggggcggttc ctcacctcga ccggcccgcg tactccatgt ttgccccga gttcatcgag   480
atcatgatcg ccgtagatgc ccatacggtc gagaatggtt gtttgcagtt tgtgccaggc   540
tctcacaagg aagcagcccc gatctcggcc gacgccgcat tgcatcggc gtggctagag   600
ggcaaggagt tcatccccat ggtcctcgac ccgggcgacg tcttgatctt caacgagagc   660
atggccatc ggttggagcc taacaagacg gaccaaagac gtgcagccgt ctttggcacc   720
taccactttg acctgtccca gcccgacctg cgggataaat tctacgccca ccggctcatc   780
cacagccctc cggaaaacgg taaggctttt ccatgaaaag atgatgtttg catgtttgga   840
gaccaatgct aacatgatac gtgaccaatc ttacgtagcc tgggttgaaa agtgggagc   900
gcagacttga caagaac                                                 917

SEQ ID NO: 54           moltype = DNA   length = 1372
FEATURE                 Location/Qualifiers
source                  1..1372
                        mol_type = unassigned DNA
                        organism = Epichloe uncinata
SEQUENCE: 54
atatcacgat tcctcactct ttccgaggca ctaatcccaa attcaacatc aagattctat   60
ctgttcaact cccaagatga cggtaacaaa caagcctgtt aagcctgcta atgtgccagt   120
gatggacttt gaggcaatcc atgccagtgt cgggaatgag cgcaagaaat acttgcgaca   180
gctcgacgag gcatggagcc atcacgagc catctacgtt attaaccaca gtattggaac   240
taggacgctc gaggaagcat tcgcctgggt aagtagctgg cctggttact caagaatggg   300
ctggcattcc ccatgcaagt taggatcgct aattgatctt gtgtgccttt tgaaatcag   360
tgcaagaagt tttttgacct gcctctggcg gtcaagaact cggttcacat cccacctgac   420
gtatcaaagc atttccaggg ctggacgggc acaggcgagg ccatctcctc gcagggcgtc   480
tgggatcccg acgagatcga gaggctccgc aaggagacgc cgacggatga caaagagcc   540
atggagctgc aggaccttg cggaacgtac ccccgggcg cccccgatct aaacttggtg   600
gagcagcatc tcccgggctt tctcgacttt ctgaagaagt ggttcgcggc tgctacaag   660
caatctctcc agaacatgcg gctcgtgtgc gaaatcctcg gatgcgagga tctgattac   720
attggaaaaa agtttgagcc gcgccacatg agcacccact caacttggaa ctacttcctg   780
gggcagcccg tttcacagct ggccagcgga tccgcgaacc ggctcaacgc gcatacgaag   840
tactgccagt tcaccatgct cttccaggac atggtcgggg gcttgagct gcacgactac   900
gaggaagaca tttaccgacc tgtgcctccg atcaaggggg ctatgattgt tcaagttggg   960
gacctgcttg agaagcagac caacggcaga tggcggagcg ccctccaccg cgtcacgcg   1020
ccgagccggt acatgtacga aggaagtgcc ggtgacgatg acgagctggt gcagcgctac   1080
tcgctctctg tcttcggaca cttgaatctg gacgagatga tcgaacctc gcctggctca   1140
gagaagcaag gaaagtggag cacgctcaga tggaaggacc ggatgacggc agggcagtgg   1200
ctggcccgcc gagttgctct tgagtatgag cgcaagacag cagcaacggt catgtaggag   1260
gcgacgagg cctgaggctt gtagtagtga agtgatttgc actgaaacaa cgaactagtc   1320
cgtacagtct gctacctagt attcaatcat gagcacttat gccagtcggt ca          1372
```

| SEQ ID NO: 55 | moltype = DNA length = 1376 |
| --- | --- |
| FEATURE | Location/Qualifiers |
| source | 1..1376 |
| | mol_type = unassigned DNA |
| | organism = Epichloe uncinata |

SEQUENCE: 55

```
acaaatcaca attcttcact ctttccgaga cgctaatccc aaattcagca tcaagatttt   60
atctgtctaa ctccaaagat gacggtaaca aacaagcctg ttgagcctgc taatgtgcca  120
gtgatggact ttgaggcaat ccatgccagt gtcgggaatg agcgtaagga atacttgcga  180
cagcttgacg aggcgtggag ccatcacgga gccgtctatg ttattaatca cagtattggc  240
actgagacgc tcgaggaagc attcgtctgg gtaagtagct ggcctggtta ctcaagaatg  300
ggctggcatt cccatacaa gttaggagcg ctaattgatc ccgtgtgcct ttgaaatgca  360
gtgcaagaag ttttttgacc tgcctctggc ggtcaagaac tcggttcaca tcccacctga  420
cgtatcaaag catttccagg gctggacggg cacaggtgga gccatctcct cgcagggcgt  480
ctgggacccc gacgagatcg agaggctccg caaggagatg ccgacggagc tcaaagaggc  540
catggagctg caggaccctt gcggaacgta cccccggggc aacccagatc taaacttggt  600
ggagcagcat ctcccgggct atctcgactt cttgaagaag tggttcgcgg cctgctacaa  660
gcaatctctc cagaacatgc cctcgtgtg cgaaatcctc gggatggagg atttggatta  720
cattggaaaa aagtttgagc cgcgccacat gagcacccat tcaacctgga actatttcct  780
ggggcagccc gtttcacagc tggccagcgg atcctcgaac cggctcaacg cgcatacgga  840
ctactgccag ttcaccatgc tcttccagga catggtcggg gggcttgagc tgcacgacta  900
cgaggaagac atttacagac ctgtgcctcc gatcaagggg gctatgattg ttcaagttgg  960
ggacctgctt gagaagcaga ccaacgcag atgcggagc gccctccacc gcgtgacggc 1020
gccgagccgg tacatgtacg gaggaagtcc cggtggcgat gacgagctgg tgcagcgcta 1080
ctcgctcgtc ttcttcggac acttgaatct ggacgagatg atcaaacctc tgcctggctg 1140
cgagaagcca gggaagtgga gcacgctcga gtggaaggat ctgatgacgg cagggcagtg 1200
gctggcccgc cgagttgctc ttgagtatga gcgcaagaca gcagcaacgg tcatgtagga 1260
ggggacggag gcctgaggct tatagcagtg aagtgatttg caccgaaaca atgaactagt 1320
ccgtacagtc tgctgctacc tagtattcaa tcatgagcac ttctgccagt cggtca      1376
```

| SEQ ID NO: 56 | moltype = DNA length = 1735 |
| --- | --- |
| FEATURE | Location/Qualifiers |
| source | 1..1735 |
| | mol_type = unassigned DNA |
| | organism = Epichloe uncinata |

SEQUENCE: 56

```
ggtgctggtt tgaaacttac ttcttacatt gcaaggtttt cgtcgtcaat atccaatagc   60
cctcactgct ttactctccc agactatccc cgctgttctt aacaggcaga gcagccatgg  120
ccagcccagg gaatcatgcc attgtcgctc ccggatgacc cagatcagaa gacggctctc  180
tcacacggcc cctcgacttg gtggagaact ggctgcttgc ccgtatccaa cgcgccaaca  240
cgcctcctgg tcgtgaagcc gagggtctca cctacaagct caaattacga ctgccccaag  300
acattgatga ccccatcccc tacctccgcc gcgcttggct tgttttttcga tatgtccagc  360
cgctcatagg cgcaatatat ccgccctatt cagaacgaga tgagacaggg cgattacctg  420
ttacggttcc cctcatggat cctgaggagt ggctgcggct aagttccac gtaaaccaag  480
ggacccaggc tgtttttcagg gacgtggacg atgccggaaaa gatctttcaa cctcgtccaa  540
cggcaatggc ctactggttt cctccttcgt cgaccttgat tattcgcagc actcacctcc  600
gatttgacgc tgtgggaata tacaaggcga caaacacctt catgctcggt ctcgagtcag  660
tcttccgtct cggcctcgac gccaacctag attgctacac taccgatgtc aaacaaccgt  720
ccctcccgcc cggcatcgac tatattctgg ggttcccgcc gcaggagaca cccgtcccac  780
accgcgtgga gcgtgccgtc gatgagctga tgcggcattg gcatcatggt ttgtacagct  840
tgtctctccc cgtgcgtgag gggtccgagg acgccgcgtc tgccaacacc caacacctgg  900
tgactttgtt cgacgagccg acgctcgagg ccatcgtggc gggttgcaag aagctgggcg  960
tgagcgtctc ggccgccgtc cacgcgagta ttgtccgcgt ctgggcctca ttccctcaac 1020
aacagcacac cggagcgcgc aacatgctca ttccctcgt cgcgaacctg cgtccacttc 1080
tggaccccaa gtgggttgtt ccggactacg cactcggcct ctgtatcttt gtcgtgccgt 1140
tctgtctcac gggtggcttc gaggacctca cgcaacgtct gggtgctgtt tactcgcgag 1200
atctgtcggc gctgccctca gacccggcag gcgaccctgt gagctttctc gagctgctgc 1260
cgctgtatga aagccgggag gccgctttcc ttggctcctt gcccgttgcc ggctgtccgc 1320
ccttccgggt acccaacctc agtagcctcg gcgtgttgga gagatatcta gccgcgcgt 1380
acgggaaaaa gggggcacaa gccctgtttt gtgagatcga agacgtagcc ctcgtcaatg 1440
caacgactga tccaaccatc gagttccagc tatttacctt ccgcggcact atgcggctgt 1500
acttgtacta caatgatgca tactatacgg aagactttct ggctcccgtc atggagatgg 1560
tgcgcgcacg tcttctccag gagctaggac tcggtggaag ttagtcttca gaagcactag 1620
atccgaagga atcttgaacg ttgttgtcac tagagtggtc gatcagctgc taaagaaaag 1680
tcagtatcac gggaagtact aaagctgctt gtaactacaa tgaggtttta gtttt        1735
```

| SEQ ID NO: 57 | moltype = DNA length = 1629 |
| --- | --- |
| FEATURE | Location/Qualifiers |
| source | 1..1629 |
| | mol_type = unassigned DNA |
| | organism = Epichloe uncinata |

SEQUENCE: 57

```
ctctcccaga ctatcccgc cgttcttaac aggcagagca gccatggtca gcgcagggaa   60
tcatgccatt gtcgctctcg gatgaccac atcagaagc gcactcctca cacgcccct   120
cgacttggtg gagaactggc tgcttgcccg tatccaacgc gccaacacgc tcctggtcg   180
tgaagcgag ggcctcacct acaagctcaa attacgactg cccaagaca ttgatgaccc   240
catcccctac ctccgccgcg cttggcttgt ttttcgatac gtccagccgc tcataggcgc   300
aatctatccg ccctattcag agcgagatga gacagggcgg tacctggtta cggttccccc   360
aatggatcct gaggagtggc tgcggctaag ttttcacgta aaccaaggga gccaggccgt   420
```

```
tttcagggac gtggacgatg ccggaatgat ctttcgacct cgtccaacgg caatggccta    480
ctggtttcct ccgtcgtcga ccttggttat tcgcagcact cacctccgat ttgacgctgt    540
gggactatac aaggcgacaa acaccttcat gctcggtctt gagtcagtct tccgtctcgg    600
cctcgacgcc aacctagatt gctacactac cgacgtcaaa caaccgtccc tcccgcccgg    660
catcgactat attctggggt tcccgccgca ggagacaccc gtctcacacc gggtggggtg    720
tgccgtcgat gagctgatgc ggcattggca tcatggtttg tacagcttgt ctctccctgt    780
gcgtgagggg tccgaggacg ccgcgcctgc caacacccaa cacatggtga ccttgttcga    840
cgagccgacg cttgaggcaa tcgtggcggg ttgcaaggag ctgggcgtga gcgtctcggc    900
cgccgtgcac gcgagtattg tccgcgtctg ggcctcattc cctcaacagc agcacaccgg    960
agcgcgcaac atgctcattc ccctcgtcgc gaacctgcgt ccacttctgg accccaaatg   1020
ggtggttccg gactacgcac ttagcctctg tatctttgtc gtgccgttct gtctcacggg   1080
tggcttcgag gacctcacgc aacgtctggg tgctgtttac tcgcgagatc tgtcggcgct   1140
gccctcagac tcggcaggcg accctgtgag ttttctcgag ttgctgccgc tgtatgacag   1200
ccaggaggcc gctttccttg gctccttgcc cgttgccggc tgtccgccct tccgggtacc   1260
gaacctcagc agcctcggcg tgttggagag ataccctagcg cgtgcgtacg ggcaaaaggg   1320
ggcacaagct cctgtttgtg agatcgaaga cgtagccctc gtcaatgcaa cgactgatcc   1380
aaccatcgag ttccagctat ttaccttccg cggcactatg cggctgtact tgtactacaa   1440
tgatgcttac tatacggaag acttttctgg ttccgtcatg gagatggtgc gcgaaagtct   1500
tctccaggag ttgggactcg atggaagtga gtcttcagaa ggactagatc cgaaggaggc   1560
ttgaacgtcg ttgtcatgtc actagagtgg tcggtcagct gccaaagaaa agtcagtatc   1620
acgggaagt                                                           1629

SEQ ID NO: 58           moltype = DNA   length = 840
FEATURE                 Location/Qualifiers
source                  1..840
                        mol_type = unassigned DNA
                        organism = Epichloe uncinata
SEQUENCE: 58
atgacggtga acagcagcgt gaagcaggag tacgacgccc aggccgccat ctacgatggc     60
tacatcgacc ggcccagcgg cgtgatcgag cggcagctct tcacggcaac actcggcaac    120
tgcacagggc tgacggtgct cgacctgggc ggcgggacgg ggctcaaggc gcgcgaggcg    180
gccgacgcag gggcatcggc cgtcgacgtg atcgacctgt cgcccgagat gatgcgggtg    240
ggtcgagatg ccgagcaggc gggccctcgc gcggaaaag acattctccg gtggtacgag    300
ggcgacgtga ctcgcgccga cctcgtcgag acgctgccgg gactgcgcgg gccgtacgac    360
ctcgtcatcg tcggctggac cttcgaccac gcgcacgacc gggcgcagct tgaggccatg    420
tggcacaacg ccgtggtgag gctcaagctc ggcactggcc gcctgctcgt cgtccgcaac    480
ggcgatccgc gcagccctgc cgtcaccggc ggccgctacg gcatccgcta cgccgaccat    540
gtacccatcc ccggcgggtt ccggttccgc gatcagatga ttcgttgggg aggcggcggc    600
caaaagcagg ggaaaaaccc cgaccagttc gagatcctcg ccgactacga gtgcaccgcc    660
ctcgaggtca tgtactccgg ctcgcacgag atgtaccatc agttcggcct taccgacatc    720
cgcgtccagc cctatgaaga gacggctgcc gtccgagccg accgccctt ttgggcccag    780
ttcctcgaga acccgtgtct ggcgtcgtc acggccggga gatgggcat ggtggaatag     840

SEQ ID NO: 59           moltype = DNA   length = 2005
FEATURE                 Location/Qualifiers
source                  1..2005
                        mol_type = unassigned DNA
                        organism = Epichloe uncinata
SEQUENCE: 59
atgtcgaaca taagagctac gattgcgggg ggtgcgcgt ggcaagaggt agcagcagac      60
tgccaacagc atcgcgatgc gactattgcc aaaatccacc ctcccattcc agatacacaa    120
gcactcgaga gccttttcgc aggcggtgat ccgcgcgacg tcttgagcat tcccactctc    180
gtcctcacga agggggaact tgccatcacg tcggccaatg tcgaggatct tgttcccagg    240
ctggctagcg gagagtggag cgccagcacg gttttgaagg ccttcttgcg cagggcggcg    300
ctagcccagc ggctcgtgaa ttgcgtgaca gagatgcttt cagagacggc cttgaagaga    360
gcagcagaac tggatgaaca ccttgcggtc cacgggaaac ccattggccc actccacggc    420
gtccctatca gcgtcaaaga gcacatagct atgaaaggat tggacgttaa tggtggctac    480
gtatccgagg ttgggcgcgt cgctgaggaa gatgcgctga ttctaggcat cctccgggat    540
gcgggcgcca tcttctacgt caggacaaca agccacagt catcaatgca cctggagacg    600
agtagcagtc tctatgggta agtcgcacgc ggcaatttgg cgcctgcttg accaacaatc    660
gactgaccat tggacagaga gactgtgaac ccctttaaca ccaccctcac ttcgggcggg    720
tcttcgggcg gagagggcgc catcatcgcc atgcgaggct cggtgctagg ggtcggcagt    780
gacatcgggg gaagcatccg ctcaccggcg cattgcaacg catcttcgg gttcaagcct    840
actgccgggac gtctacccac cctcggatgg ttcgcgctca tggttcgatc tgaggctatc    900
cacgcaacta ctggtcccct ctctaccagc atagaaggtc tttggctgtt caccaaaaca    960
ctgttggacg cgaagccatg gctccaggac cccagcctga cacccatgga gtggagagat   1020
atgtccacgg cctttgccgg gcgaagactg aaggtcgcgg tgatgtggga tgatggcgtc   1080
gttaagccgc atccgcccgt cacgcgggct ttgaaaagcg tggttgaagc tttgaagaag   1140
agcagagaaga ttgaggtggt ggactgtgaa ggactatact atgggaataa ccccttttc   1200
cccctcccc cttgccattc catcgtcggc cctcaagtct ttgcttctcg tcggctggtg   1260
ccccccaaaa caacgaccgg gcaacatcaa gtcagactaa cgcctgacat tcttgtagga   1320
aaccatggaa acacgacctt gcctggtcca tcattgtaag ctgctccaca aactcacctt   1380
gcaccttccc gactaaggca taagtgatca ggcaggcttg tactttgcg acggcggtgc   1440
tcagctaaac gctgcgtttg aagcagccaa ggaaccgctg tgtgccttt cacactggat   1500
tttgaaggag aaccccacg tcaagcacca ctccatagcc tcgctgtgga gtcgtcgcgc   1560
cgagagagac gcataccgtc tcaaatatgc cgagctctgg aacgcactg caaagggggg   1620
gggcgggcca gtgacgtga tcctgtgccc ggcggccca ggagcggcgc ccaagctcaa   1680
tacttcgcga tattgggtt atacggcaca gtggaaccta ctggactatc cgccgtcgt   1740
gttccccacc ggtgatatcg tcagcgtcga gaaggatggg gcagcaggcg agcagggagg   1800
```

```
cggcgacccg gccagtggtg ccgacctgga caattggagt ctatggacag agcatggggc   1860
tgaagggtac agcaatgcgc ccctcacttt gcagctcgta gctcgcagat atgacgacga   1920
aaagctcctg cacgctttgg agatggtgat gaaggaggct ggactaccca cggagctcgt   1980
cggaagaagc cggggcccgg cgtga                                         2005

SEQ ID NO: 60           moltype = DNA    length = 1990
FEATURE                 Location/Qualifiers
source                  1..1990
                        mol_type = unassigned DNA
                        organism = Epichloe uncinata
SEQUENCE: 60
cttgatggat ctgacccagt tcaacacagc gggcatcgtt tggccgacgg ttgctgccat     60
cgccatctcc tatatcctgc tgtcgagctt tctctcttgg tataggctac ggcacatccc    120
cggcccttc ttggcctcga tctcaagtct ttggaatgct ctaaacatcg tgactgggcg     180
cacgtcgcca gtgctcgaga aactgccagg aaagtacggc ccgctggtgc gaaccggccc    240
caactacgtt ctcacagatg atgccgaaat tttacgtcac gtcaatggcg ctcgcagcac    300
ataccccgt aatgggtgta agtctgtcca tatcacatgt cttttgaaat gtaggagac      360
tcagagaccc actcacactg tggcttccag ggtatgaagg cttcaaggtc gatgaacacg    420
accatatggg gtcccatatc gacacgtcgg tacatgacgc catcaaaagc aaggtgattg    480
gggggtacaa cggcaaggat gggatagacc tcgaggggc catcggatcg caggtcaaga    540
ccctggtcag tgagatccgg cgccgtcacc ttgggcaacc tgtcgacttc tctcgtctga   600
tgcgtcagat ggcgctcgac gccatcaccg ccgtagcctt tggcgaggcc cttgggttcc    660
tgacggccga agacgagac gtgttcggct acgtcagcgc cgttgacaag atgctgacct    720
acctgacact tgccagcgac ctgccgtag tgccagctt tgtccggtca cgccgcatgg     780
cgccggcggt gcgttgcgtc ctggcctata ctggcattgg ccgcatgctc aaccatacac    840
gccgggtggt ggcggagcgc tacgcggccg acgaccccgg gaaggcgcac atgacgcgct    900
cattcatccg caaggggctc acgcagatcg agtgcgaggg cgagagccac ctgcagctca    960
tcgccggcgc cgacactgcc gtcacggtgc tgcgctccac gctgctgtac atcatgacga   1020
cgccgcgcgt gtacacgcgg ctcaaggccg agatcaaggc cgcggtggat gccggcgagg   1080
tggtcgaagt catcaccatg gcccaggccc agaggctgcg gtatctgcag gctgtcgtga   1140
tcgagggctt ccgcatgcgc ccggccgtcg tgtacgggca cttcaagtcg gtgccggccg   1200
gcggcgatac gctgccgaat ggtgtacgcc tgcctgcagg caccgccatc gcccccaact   1260
acatagcact gacccggcgc gccgacgtct atggcgccga tgtcgatttg tttcggcccg   1320
agcgttttcct cgacgccgag ccggccaagc gccacgagat ggagcgcgcc atggacctga   1380
acttcgggct tggccgctgg cagtgcgctg caggaaacat tgctctcatg gagatgaaca   1440
aggttttctt cgaggtcggt ggatgtgcat ctccgctctt tgcttttgtt tctttttcctg   1500
ctattactct cgccctcctt tgctatcctg acgcgggcga ggtatgagac gagatgagag   1560
actgattcaa tgccagtta ttacgccact tcgacctcca gatcttgtat ccggggcaaag    1620
catgggatga atacacgtaa ggccttctga aacctttttt aataccttttc gcgcataggc    1680
gtctcgggtg gcgtgagcag cgtgccatga atattggagt gctaaccagg ttacctctta   1740
cctctgcagg ggcgtggtat attgcagca taacatgtgg gtacaaatca ccgagagctc    1800
gtgagagagc gcaaaggtga gtatagtgta cagggataca catggcaggg gtggctacga    1860
acgtccatga ccacgtacga ggcggtaccg atgggcggga aaggacacga ctgagacggc    1920
tggagagaac gatgaagatg gggtaaggaa ttatagcaat cagaataacg atcgtgtttg    1980
tgcgcgtcgg                                                         1990

SEQ ID NO: 61           moltype = AA    length = 446
FEATURE                 Location/Qualifiers
source                  1..446
                        mol_type = protein
                        organism = Penicillium expansum
SEQUENCE: 61
MTVTAEIEAS PSRDPRAFET LLLHGGRFPD VLGSCAVPVY NSAPTVNVLQ NRIALLEGGV     60
AACAVSSGSA AVALTMMALA GTGDNFVSSF HVHGGTFHQF SVLAKQMGIE CRFIKSEDPQ    120
AYADAVDERT KFVWIETISN PGNVIPDFEE LAKVARENGL PLICDNTFGC AGYFCRPIDY    180
GVDIVVHSAT KWIGGHGTTI GGLIVDGGTF DWGRHRDRFP QFHATDTRLW EKFGRRAFAM    240
RCQFEILRDT GSTLSASSAQ QLLIGLESLA VRCQRHAENT QALADWLCGN SNSQKRQVSW    300
VNYIGHPDHP HHALAKRYLR RGFGSVFTFG ITGGVAASAR FCDALKLVII TTNLGDAKTL    360
VVHPASTTHE HFTPEDRKAC GVTDEMIRLS VGIEQIDDLQ ADFAQAFAQL HIPCAPQPPE    420
LALLEEAQEE VVAALYNYPP GIFMGN                                        446

SEQ ID NO: 62           moltype = AA    length = 409
FEATURE                 Location/Qualifiers
source                  1..409
                        mol_type = protein
                        organism = Penicillium expansum
SEQUENCE: 62
MIEPQTIKGA IERQIQQNNA QKTSHLSEAS FFVADLSEVI TKYNLWQKTL PGVTPFFEAN     60
IQPQTAVKSN NDRQLLQTLS QCGAGFDCAS AEEIELVLSL GVPAKRIIYT HPCKPISSIE    120
FCRRASIELI TFDNVEELQK MKDHYPEARL MLRVFADDHT GVDPLGSKFG VATQDAPSLL    180
TTIKALQLNF EGVSFHVAPT NADPAGYVRA IQDAAKVFKD ARGLGLQPNT LDIGGGYTDE    240
TFPHIAAEAK RTLDECFGNG SIIPRPQLIA EPGTLLSCSS FHLAVQVIAR RTNATGFGGE    300
APTRLYINDG IYSNFMMRFI VTSSFVPVAV IRDGKWHDEN AQGTLECSVW GRSCDQNDCI    360
NSRCMFSQEV RTGDWLVFKD MGAYTTVCST TFNGFTSPNH VIYLDAPLN               409

SEQ ID NO: 63           moltype = AA    length = 531
FEATURE                 Location/Qualifiers
source                  1..531
                        mol_type = protein
```

```
                             organism  = Penicillium expansum
SEQUENCE: 63
MTRDVLDVAI VGAGFSGILA LHRLRQLGLR VRGFERKASL GGVWRENAYP GAAVDSPFPF      60
YQFYDAGLLQ DWQWREEYPS RAEMLRYFEQ VDREWSISEG FEFGAHITGA RFSAESQQWA     120
ISLADGREIY AQWFIPAVGF NSVVNMPQIP GLDRFQGQVY HTAQWPHDAV SMENKNVAII     180
GTGPSGVQII QSVGEVAKSL TIYQQTPFLT LPKYGNRPPK LAGSDLLEMG VEAFDAAFQR     240
GLQSFSGFDY TMRDQDTLSA STTERLEFYQ KRIREGGWAF WMGGFRDLNY DARANRDTYD     300
FWAENVRPRL QDAMKRDLLV PHQPGSPFGV KRPCLEDRLY EMIDRHHVDM IDVSQRPIQA     360
ITIGGIQAHD EIRSFDVIIM ATGFGDDASG LKQLSIHGRD GVSLAEMWSD DIHSFLGMAV     420
HNFPNMLYLY GPQCPSLLVS SPAVIHQVE  WICQALMCFR KAGVVQVEST AESQKLWREK    480
IDRLWSKSLY CRPGAKNKGA TWIGGLVEYQ KELCKCLDEG FPGFDLTFAQ N             531

SEQ ID NO: 64              moltype = AA  length = 474
FEATURE                    Location/Qualifiers
source                     1..474
                           mol_type = protein
                           organism = Penicillium expansum
SEQUENCE: 64
MPALPLSENE GWKRPTTPFG KPMLKHFCMN PEYRNLNAPS CGSWPKTVRD QWRRYLDDLE      60
AQPDYFSEVK QGPVIQEARR EVAQLLHARV SECVFISNAT TGIYTVLHNI PFDKDDVIIT     120
FSTTYGAIDN AIASMAETQP FQTRKVTVDL PMRGEDIVAR FEGMVAQIKA EGLHPRLAVL     180
ETIVSIPAIR MPFESLVQAC QREGVLSLVD GAHSIGQFSL NLEVLQPDFF IMDCHKWLFV     240
PRPCAALYVP ERNQHYIRST IPPSFGFIPR DGKPALPLWS KQSGGGSSGS TATDFETIFA     300
YVATSDNMPH MCIPTALKFR REVCGGEEAI YQYLRVLAKE GGDRVAAILG TEVLDEKPAG     360
EYKSQRTPSE MRDCGIATVR LPLAVSSSLK PPPHSGTPYS PLSDEEVGPA VHYLSMTLAE     420
THKTWLPLID HGGYIWVRLC AQIYLDTSDF EWIGNVLKEI CETIGKKGHV ISKH           474

SEQ ID NO: 65              moltype = AA  length = 262
FEATURE                    Location/Qualifiers
source                     1..262
                           mol_type = protein
                           organism = Penicillium expansum
SEQUENCE: 65
MPSLPSLAHD PAPKLPTLTP KQIQHYQEKG YLILPQAQHH LFPSLQSFKS WIHEVSVWPS      60
PPDPTKPESY RLYYEPSPVP GEDPLLFDTE RVSESHQPLA NIITGPAAIS LLHQLTGQQM     120
LLFKDEVAWK LPGGRGAIPH IDLPAYGDFA PEFVEIMIAV DAHTAENGCM EVVDGSHREE     180
VPFGEGGRIV GDWVQKLEGQ GREFVPVVLE AGDILIFGEK LAHRLGPNKT DQRRAAVFAT     240
YHFDLEKPDL RDEFFAHRLV FD                                              262

SEQ ID NO: 66              moltype = AA  length = 361
FEATURE                    Location/Qualifiers
source                     1..361
                           mol_type = protein
                           organism = Penicillium expansum
SEQUENCE: 66
MVGIEIVEPA DVPVIDLNAL SSPSPAERRV ALAQLDEAYR TYGAIWLVNH SIGVDLVEEA      60
LAWRFFQLPR EQKQTVSMPT KNASERIEGW SDVGASISSQ GVWDPNELEK IRAASSIELK     120
EVLDSLDPTS EAAQDSERLR KLDQMLPGFP AFIERWWDAC FKQQTELMRC LCEILGIADT     180
DFIVKQQQTP RHGSTHLTWN YFLGMPLSPL SSGSANRLNP HTDYGQLTLL FQDMQGGLEI     240
LDPVAGIYRP VPPLKGAMII QVGDILEKQS NGRWRSPLHR VTAPNHLMYG GNPGERSDQQ     300
EDALVSRCSI VFLCYPGYET VIEHLPGCEK KGNWKTLEWE GNMTAGEWIK RRAALEYERP     360
E                                                                     361

SEQ ID NO: 67              moltype = AA  length = 554
FEATURE                    Location/Qualifiers
source                     1..554
                           mol_type = protein
                           organism = Penicillium expansum
SEQUENCE: 67
MAVASQQKLS WQESARQVQA ARDRSIEDVD SAIAALPATY TGRVIDFPRK HLSQTEIAIT      60
ESSAETLVAS LATGKLTATA VANAFLRRAA IAQKLTNCIY ELLPDRAIAR AKELDDYLAK     120
HGKPSGPLHG LPISIKGHIG LKGRDLSAGF VAWLDRESPD DANIVKILLD AGAVVYARTT     180
EPQGLMALET CSNITGITTN PHNTALTPGG SSGGESALQA LHGSPLGIGS DIGGSIRSPA     240
ANCGLYGLKP STGRLPLIGC ASYVLGCETI VGTLGPISPT FGGIELFLKT IIESKPWVKD     300
SMMLPIPWRD QEKHIHLDNK KLTVGVMWTD DVVTPAPAVT RALKEVVGRL KLVDSVEVIE     360
WKAYQQKEAL EILTRLYAPD GGKAFAGHLE ASGEPFTPLT AWSLRDAPGI EELSQQGLWD     420
WTGKREMFRY AYLQQWNNVA PEMDVILCPA FPTPAPLHFT SRYWGYTSLF NLLDYPALVF     480
PVTKVDPDRD AKHTTYTPKN EFDSWAYEHY DSVKQKDAPV SLQLVSKKLE EEKLLQAFKE     540
IQERIGLPFV NCLA                                                       554

SEQ ID NO: 68              moltype = DNA  length = 1802
FEATURE                    Location/Qualifiers
source                     1..1802
                           mol_type = unassigned DNA
                           organism = Penicillium expansum
SEQUENCE: 68
atgacagtga ctgctgaaat tgaggcttct cctagtcggg atccgagagc gtttgagacg      60
ctgcttctcc atgagggtgg gtttgattg aaggagagct agaggaatat cagtaatgct     120
aagtgattta ttgtggcgca ggagatttcc cgacgtgttg gcagttgtg ctgtaccgt      180
```

```
ttacaattcc gcggtagggt attcaattca agttcatgca gtctcaagcc cttctctaac    240
tctcccttcg tgtctttgg ggtcgctatc taggctttcc aattcaacag taccgagcat    300
ggtgcgcgat tgttgaatgt tacacaactc ggacacatct atagtcggtt cacaaatgtc    360
tgtctctatc actttctaga tcctttcgga tcttatatgc tggtagccac tgacactttg    420
tttctagccc acggtaaatg ttcttcagaa ccgcatcgct ctcctggaag gaggagtagc    480
cgcttgtgcg gtctcgtcgg ggtctgcggc agtggcgttg acgatgatgg cactggcggg    540
cacgggggac aatttcgttt cctcgttcca tgtccacggg ggcactttcc accaatttag    600
cgtcttggct aaacgatgg gcatcgagtg tcggtttatc aagtccgagg atccgcaggc    660
ctatgccgac gccgtggatg agcgcaccaa gtttgtatgg atcgaaacca tcagcaatcc    720
cggtaatgtg atcccggact tcgaagagtt ggccaaggtg gcacgggaaa acggactacc    780
actgattgta agactactga ttctttgctt cttgattttg tttaccggat taggctcttc    840
ccatgactca gtactcgtgg aaatctaaca atctggcagt gcgacaacac cttcggctgc    900
gccggatatt tctgccgacc tatcgattat ggggtgata ttgtggttca ctcagccacc    960
aaatggattg gcgggcacgg cacgaccatc gggggtctca tcgtggacgg cggcaccttc   1020
gattggggcc ggcaccgcga ccggttcccc cagttccacg cgaccgacac gcgcctatgg   1080
gagaagttcg gccggcgggc gttcgcgatg cggtgccagt ttgagatctt gcgggacacg   1140
gggagcacac tcagcgcgag ctcggcgcag cagctgctga tcgggctcga gtcgctggcc   1200
gtgcgatgtc aacgccacgc ggaaaatacg caggcgctgc ctgattggtt gtgcggcaac   1260
agcaacagcc aaaagcgcca ggtcagctgg gtcaactata tcggccatcc ggaccatcca   1320
catcatgccc ttgctaagcg gtatctgcgg cgggggttcg ggtccgtgtt tacatttggc   1380
atcacgggcg gtgttgcggc cagcgcgagg ttctgcgatg cattgaaatt ggtgattatt   1440
acgacgaagt acgtataccc tctctgaggg gatgatactg gcagagtaaa gccgaacaac   1500
actaacagct acatccaagc ctcggagatg ctaagaccct tgtcgttcat cctgccagca   1560
ccacacacga gcatttcacg ccagaggatc gcaaggcctg cggggtgacg gacgagatga   1620
ttcggttgtc ggtggggatt gagcagatcg acgatctgca agccgatttc gcccaggctt   1680
ttgctcagct ccacattccg tgtgcccac agccgcccga gttggctctg ctggaggagg   1740
cccaggaaga agttgtggct gcgctatata attacccacc agggattttt atgggcaatt   1800
ga                                                                 1802

SEQ ID NO: 69           moltype = DNA  length = 1425
FEATURE                 Location/Qualifiers
source                  1..1425
                        mol_type = unassigned DNA
                        organism = Penicillium expansum
SEQUENCE: 69
atgattgaac cccaaacgat caaaggagcg atcgagcgac aaattcagca aaataatgcc     60
caaaagacca gtcatctatc cgaggcttcc ttcttcgtcg ctgacctgag tgaagtcatt    120
accaaatata acctctggca aaagactctc caggggtga caccattttt cggtaagagg    180
tgtgatgatg aagtttccaa atcgacaaaa caaccataaa acaaccggga gaggctaaca    240
tccagcccca aacagctgtc aagagcaaca atgatcgaca gttactccag acgctttccc    300
agtgcggcgc cggcttcgac tgcgcctcag ccgaggaaat tgaattggtt ctctctctcg    360
gggtgccggc gaagcgcatc atctacacgc acccctgcaa gcccatcagt tccatcgagt    420
tctgtcgccg ggccagcatt gagctcataa cctttgacaa tgtcgaggag tccagaaga    480
tgaaagacca ctatccggag gcccggctga tgctgcgagt cttcgccgac gaccacacgg    540
gcgtcgatcc cctgggcagc aagttcggcg tcgccaccca agatgctccc agccttctca    600
cgactatcaa agcactgcaa ttgaactttg agggagtgag cttccatgtt ggttagttct    660
ctcccttccc tcatggagcg atcccgaaaa aaacgactg acaattcttg tttggattt     720
ccagccccga ccaacgccga cccagccggc tacgtgcgcg caattcaaga cgcagccaaa    780
gtattcaaag atgcacgggg cctggggctg cagcctaaca ccctcgatat cggcggcggg    840
tacacggacg aaacattccc gcacatcgcc gccgaagcaa agcggacgct ggacgagtgt    900
ttcggcaacg ggtcgatcat cccacgaccg caacttatcg ccgagcccgg cactgctc     960
tcgtgcagtt ccttccatct agcggtgcag gtcatcgcgc gccgcacgaa tgcgacgggt   1020
tttggcggcg aggcgcctac ccgcctctac atcaatgacg gcatttacag taacttcatg   1080
atgcgcttca tcgtcacctc gagctttgta cccgtgcga ttatccgcga tggcaagtgg   1140
cacgatggaa acgctcaggg tactttggag tgctcggtct gggccgctc ctgtgaccag   1200
aacgactgca tcaatagccg gtgtatgttc agtcaggagg tcaggacggg cgattggttg   1260
gttttcaagg atatgggagg tctgtttgcc cccttcccg gctaatatgc gatagttttg   1320
ctaacaatca tgacgctgc agcgtacact ccgtctgtt caaccacctt taacggattc    1380
actagtccca accacgtcat ttacctggac gctccgttga attag                  1425

SEQ ID NO: 70           moltype = DNA  length = 1727
FEATURE                 Location/Qualifiers
source                  1..1727
                        mol_type = unassigned DNA
                        organism = Penicillium expansum
SEQUENCE: 70
atgactcgcg acgttttaga cgtggccatt gtcggagccg attttcagg catcttggct     60
ctccataggt aagtaagcta gttgacgttc gtttcaggtc cgaatcctag agaccgaacg    120
ctcacgaatc aattagacta cggcagttag ggcttcgagt tcgaggcttc gagcggaaag    180
cgtcgctggg gggggtgtgg cgagaaaatg cctatcccgg ggccgcgggtc gatagtccat    240
ttccattcta ccagttctac gatgctgggt tactccagga ctggcagtgg cgcgaagaat    300
acccccagtcg agccgagatg ttacgatact tcgagcaagt cgacagagaa tggagcatct    360
cggaaggctt cgaattcggg gcccatatca cgggagcccg ttctcggcg gaatcccagc    420
agtgggcaat cagtctgct gatgggcgtg agatctatgc gcggtggttc atcccgcgg    480
tgggcttcaa ctcagtggtc aatatgcccc aaatccccgg cctggatcgg ttccagggcc    540
aggtctatca cacagcccag tggccgcacg atgccgtctc gatggagaac aaaaacgtgg    600
ccatcattgg taccggaccc agtggcgtgc aaatatccca gagcgtgggc gaggtggcca    660
aaagcctaac gatctaccag cagacccct tttgacact ccccaaatac ggcaaccggc     720
caccaaagct ggcgggtctt gacctgctag aaatggcgt ggaagccttt gatgccgcgt    780
```

```
ttcagcgcgg cctgcagtcg ttcagcggat tcgactatac gatgcgcgat caggacacct    840
tatctgcctc gaccacagag aggttggagt tctatcagaa gcgaatccgc gaaggcggct    900
gggcattctg gatgggaggc ttccgtgacc tcaactacga tgcccgcgcc aacgggaca    960
cctatgactt ctgggcagag aacgtccgac cccgtctgca ggatgcgatg aaacgtgatc   1020
tgctagtgcc acaccagccc ggctcaccct ttggggtgca ggcccctgt ctggaggaca   1080
ggctgtatga gatgatcgat agacaccacg tggacatgat cgatgtcagc cagcgaccca   1140
tccaggccat taccattggc ggtatccagg cccacgatga gatccggtcg tttgacgtga   1200
tcatcatggc gacgggattc ggggacgatg cgagtggctt gaagcagctg tcgattcacg   1260
gtcgcgatgg tgtctcgcta gcggagatgt ggtccgacga tatccactcc ttcctcggca   1320
tggctgtgca taatttcccc aacatgctat atctttacgg accgcagtgt ccttccctgc   1380
tagtcagctc tcccgccgtc attcatgtcc aagtcgaatg gatctgtcag gcgctcatgt   1440
gtttccgaaa agctggggtg gtccaggtcg agtcaacggc tgagtcacaa aagttatggc   1500
gcgagaagat cgaccggctt tggtcaaaat ctttgtattg ccggccgggc gcgaagaaca   1560
agggagcaac atggtacgtt atctctctac agatatagta gcttggcacg tttgtctctg   1620
acttaaggcc taataggatt ggaggggttgg ttgaatacca aaggagttg tgcaagtgcc   1680
tagatgaagg gttcccaggg tttgatctga catttgcaca gaattaa                 1727

SEQ ID NO: 71           moltype = DNA  length = 1528
FEATURE                 Location/Qualifiers
source                  1..1528
                        mol_type = unassigned DNA
                        organism = Penicillium expansum
SEQUENCE: 71
atgcctgcac tccctctctc tgagaatgag ggctggaagc gcccgaccac ccccttttgga   60
aagccgatgc tgaagcattt ctgcatgaac cccgagtatc gaaatctcaa tgcgcgtagg  120
taagcttcaa ccgaatatga ggtctcgggg gactaatacg caccagcatc ctgtggttcc  180
tggccgaaga ccgttcgcga tcagtggagg cgttacctcg acgatctcga ggcccagcct  240
gactacttct ccgaggtgaa acaaggcccc gtgattcaag aggcacggcg ggaggttgcc  300
caactacttc atgcccgcgt ctccgagtgt gtgttcatct ccaacgccac cacggggata  360
tacaccgtcc tccataacat tccttttgac aaggacgacg tgtcatcac cttctcgaca  420
acgtacggcg ccatcgataa tgccatcgcc tcgatggcgg agacccagcc cttccagaca  480
cgcaaggtga ccgttgacct gcctatgcgc ggagaggata tcgtcgcccg gtttgagggc  540
atggtagctc agatcaaggc ggaggggttg catcctaggc tggccgtcct cgagaccatc  600
gttagcattc ccgccatacg gatgcccttc gaatccctcg tgcaagcctg ccagagggag  660
gggttttga gtctggtatga tggtgcgcat agtatcggcc aattctccct gaacctcgag  720
gtgctgcagc cggactttt tattatggac tgccacaagt atgaacagaa aactcaattg   780
attcttgaat gttctaaca cagaaaatag atggctgttc gtgcctcgtc cctgcgctgc  840
actgtatgtc cccgagcgca atcagcacta tattcggagc accatccgc catcgttcgg  900
cttcatcccg agggatggca agcccgctct gcccctctgg tctaagcagt ccggcggttgg  960
tagtagtggc tccacggcaa cggatttcga gactatttt gcctatgtgg cgactagcga  1020
caatatgccg catatgtgca tccccacagc cctcaaattc cgtcgtgagg tttgcggcgg  1080
tgaggaggca atttatcagt atctgcgcgt tctagcaaag gaaggcgggg ataggtggc   1140
cgctattctg ggcacggagg tgcttgacga gaaaccagcc ggagaataca agagtcaacg  1200
gacgccgagc gagatgagag attgtggcat tgcaacagtg cgcttgcccc tggccgtatc  1260
gtcatccctt aagcctccac cccacagcgg cacaccgtat tccccactttt cggacgagga  1320
agtgggaccc gcagttcatt atctgtccat gaccttagcc gaaactcaca aaacatggct  1380
tccactcatt gaccacggag gatacatctg ggtgagattg tgtgcacaga tatatctaga  1440
tacctcggac tttgagtgga ttggcaatgt gcttaaggag atatgtgaga caattgggaa  1500
gaaggggcat gtcatttcta aacactag                                     1528

SEQ ID NO: 72           moltype = DNA  length = 955
FEATURE                 Location/Qualifiers
source                  1..955
                        mol_type = unassigned DNA
                        organism = Penicillium expansum
SEQUENCE: 72
atgccttctc tgccatcact tgcccatgat ccggccccta aactcccaac tttaacccc    60
aagcaaatcc aacactacca agaaaaaggc tacctcatcc ttccccaagc acaacaccat  120
ctcttcccct ctctgcagtc cttcaaatcc tggatccatg aagtgtccgt ctggccatca  180
cccccagacc ccacgaagcc cgaatcttac cgcctgtact acgaaccctc ccctgtacca  240
ggggaggacc cactcctctt cgacacagag cgcgtatccg agtcccacca gccactagct  300
aatatcatca cgggcccccgc agccatttcc ctcctccacc aattgaccgg ccagcaaatg  360
ctgctcttca aagacgaagt tgcctggaag ctacccggtt ggcgtggcgc gatcccgcac  420
attgatctcc cggcataccgg ggacttcgca ccggagtttg tcgagatcat gatcgcgagtg  480
gatgctcaca cagccgagaa tgggtgtatg gaggttgtag atgggagtca tcgagagaa   540
gttccgtttg gggagggggg caggattgtt gggattggg ttcagaagtt ggagggacag   600
gggagggaat ttgtgccggt tgtttttgag gctggtatgt atttcttctg gggatttggt   660
tgaggagatg ggctgggctg actatgtgcg tacgtacgta ctataggaga tatactcatc   720
ttcggggaga agctggcaca tcggttgggg ccgaataaga ggaccagctg gcgcgcggcg   780
gtgttcgcaa cttatcattt tgatttggag aagccggatc tgagggacga gttctttgga   840
cacaggcttg tggtgtgtcc accggggatt ggtaggttat ctatttcctt tcattgtgga   900
aataataagg gcatagagga tgtcgctaac atttcgtcta tcttagtttg attaa         955

SEQ ID NO: 73           moltype = DNA  length = 1214
FEATURE                 Location/Qualifiers
source                  1..1214
                        mol_type = unassigned DNA
                        organism = Penicillium expansum
SEQUENCE: 73
```

```
atggtaggaa ttgagatcgt ggaaccggcc gacgtgcccg tgatcgatct aaatgccctc    60
tcctcccctt ccctgcgga acgccgagtt gccctggcgc agctggatga ggcctaccga   120
acctacggtg ccatttggct agtcaaccat agcattggcg tggacctggt tgaggaggct   180
ttagcatggg ttagtagaga tcttttcctc ttcccccttt cctagaaagt tcccagacaa   240
gatagcagca gatggggaaa aaggacccct gaaagtttga gtgaaacaaa gatatctaat   300
agctgctata gtgtcagcgc ttcttccaac tgccgcgcga gcagaaacag acggtctcta   360
tgccgaccaa gaatgcctcc gagcggatcg aagggtggtc ggacgtcggg gcaagcatct   420
catctcaggg ggtgtgggat ccgaacgagc tggagaagat ccgtgcggcc agctcgatcg   480
agctgaagga ggtgctcgac agcctagacc cgacctcgga ggcggcgcag gactcggaac   540
gactgcgcaa gctggaccag atgctgcccg gattcccggc attcatcgaa cggtggtggg   600
acgcttgctt taagcagcag accgaactga tgcgctgcct gtgcgagatc cttggcatcg   660
ccgacaccga tttcattgtc aagcagcagc agacgccccg ccacgctcc actcatctga   720
cctggaatta cttcttgggg atgccgctct cgcctctgag cagcggcagc gccaaccgcc   780
tcaacccgca cactgactat gggcagttga ccctgctctt ccaggatatg caggcgggct   840
tggagatcct tgacccgtc gctggcatct atcgtcctgt cccgcctctg aagggcgcga   900
tgatcatcca ggtaggcgat atcctggaaa agcagtcgaa tggtcggtgg aggagtccgt   960
tgcaccgcgt gacagcgccg aatcatctca tgtatggcgg gaaccctggg gaaagatctg  1020
accagcagga ggatgccttg gtgtcacggt gctccatcgt gttttgtgt tatcccggct  1080
atgagacggt gattgaacat cttcctggat gtgaaaagaa aggaaactgg aagaccttgg  1140
aatgggaggg taacatgacg gcggggagt ggatcaagcg ccgggccgct ctggagtatg  1200
aacggcccga gtga                                                    1214

SEQ ID NO: 74         moltype = DNA  length = 1973
FEATURE               Location/Qualifiers
source                1..1973
                      mol_type = unassigned DNA
                      organism = Penicillium expansum
SEQUENCE: 74
atggctgtgg cgtctcaaca gaagctttct tggcaagagt cggcccgtca ggtccaggca    60
gcgcgcgatc gttcgataga ggacgttgac tcagccatcg ctgctcttcc tgctacatat   120
actggcaggg tgatcgattt ccccagaaag cacctttcgc agaccgagat cgctattaca   180
gagagctccg ctgagacctt ggtggcgtcc cttgcaacgg gtaaactaac tgcgaccgcg   240
gtagcaaacg catttcttcg gcgggctgcg atcgctcaga agttggtgag taaagctgga   300
ggctgtgccc ggacaatgcc ttgaattttc aattctaaca atcaatcgtc ttattagacc   360
aactgtatct atgagcttct tcctgaccgt gccatcgccc gtgccaagga gcttgatgat   420
tatcttgcga agcatggaaa gccctctggt ccgcttcacg gttaccaat tagcatcaaa   480
ggacatatag gcctcaaggg acgagacttg tctgctggat tcgtcgcttg gctcgaccgg   540
gagagcccag acgatgcaaa tattgtcaag attctgttgg atgctggtgc ggttgtttat   600
gcaaggacaa ccgagccgca gggactggtt agcagatcta gctttcctac agtgttgata   660
tgtggctgat atcttgattt cgcggtagat ggctcttgaa acttgcagca atatcactgg   720
catcaccacg aacccacata acaccgctct cacaccaggc ggttcatctg gcggagagtc   780
agctttacaa gcccttcatg gcagccctct aggaattggt tcagacatcg gtatattgcc   840
agattctctg cattaatttc ctaattgtta ataacagatc caggtggtag tattcgttct   900
cccgccgcca attgtggcct ttacggccta aagccatcaa ccggtcgact gccgctaatc   960
ggatgcgcgt cctatgtact cggatgtgag acaattgtgg gcacacttgg gcctatttcg  1020
ccaacatttg gcggtattga acttttcctg aagacgatca tcgaatcaaa gccttgggtc  1080
aaagattcaa tgatgcttcc aatcccgtgg agagaccaag agaaacacat tcacctggat  1140
aacaagaagc taaccgtcgg tgtaatgtgg accgacgatg tcgttactcc cgcaccggca  1200
gtgacaaggg cattgaagga ggtggttggg cgtcttaaat tggtggatag tgttgaggtt  1260
attgaatgga aggcatacca acagaaagag gcactcgaga ttcttgtaag aggtctatat  1320
cgcttcaata atcaatgtga gctgaactaa ccaatgaacg tatatagact aggctttatg  1380
caccagatgg cggaaaggca tttgccgggc atctcgaggc ctctggtgag ccatttacgc  1440
cactcacggc ttggagcctt cgggatgccc ctggcatcga agaacttagc cagcagggct  1500
tatgggactg gaccggaaaa cgagagatgt tccgctacgc ctatttacaa cgttagtaca  1560
gcaataatcc atgatcgttc ctgattctaa tccgaattcg gtccaatgca gagtggaaca  1620
atgttgcgcc cgaaatggat gttatactct gccctgcatt ccccacaccc gcccctcttc  1680
actttacttc gaggtactgg gggtatactt ctttattcaa tcttctcgat tacccggctc  1740
ttgtgttccc ggttaccaag gtggatcccg atagggatgc caagcacacc acttacaccc  1800
cgaagaacga attcgacagc tgggcataca agcattatga ctccgtaaaa cagaaggatg  1860
cgcccgtttc tttacagcta gttttccaaga agttggagga agaaaagtta cttcaagcat  1920
tcaaagagat ccaggagaga atcggcctgc cgtttgtgaa ttgtctggct tga         1973
```

MATERIALS AND METHODS FOR PRODUCING ALKALOIDS

CROSS-REFERENCE TO RELATED APPLICATIONS

This application is a continuation of U.S. patent application Ser. No. 16/956,476, filed Jun. 19, 2020, which is a U.S. National Stage Application filed under 35 U.S.C. § 371 of International Application No. PCT/IB2018/060481, filed Dec. 21, 2018, which claims the benefit of New Zealand Application No. 738615, filed Dec. 21, 2017. All of these applications are hereby incorporated by reference in their entireties

REFERENCE TO AN ELECTRONIC SEQUENCE LISTING

The contents of the electronic sequence listing ("338451_71-20A.xml"; Size; 134,736 bytes; and Date of Creation: Aug. 2, 2022) is herein incorporated by reference in its entirety.

FIELD OF THE INVENTION

The present invention relates to materials and methods of producing loline alkaloids or precursors thereof.

BACKGROUND TO THE INVENTION

Loline alkaloids are produced symbiotically during infection of grasses by *Epichloë* species fungal endophytes. These endophytes are considered to be bioprotective, conferring pest, and possibly drought and disease protection to the symbionts of which they form part.

Lolines are potent broad spectrum insecticidal alkaloids with no observed toxicity to animals. These fungal secondary metabolites are major contributors to the bioprotective pest tolerance conferred on cool season grasses by *Epichloë* endopytes.

A robust and/or scalable method for preparing loline alkaloids in the absence of a symbiotic relationship is not presently available.

There is a need for a method to produce loline alkaloids in fungi that do not natively produce lolines in order to extract and use lolines as a natural pesticide.

It is an object of the present invention to provide improved materials and methods for producing loline alkaloids or precursors thereof, and/or at least provide the public with a useful choice.

SUMMARY OF THE INVENTION

Host Cell

In one aspect, the invention provides a host cell modified or transformed to comprise at least one polynucleotide selected from the group consisting of:
  i) a polynucleotide encoding a polypeptide comprising the sequence of any one of SEQ ID NO:1, 12, 13 and 61 or a variant thereof with at least 40% identity to any one of SEQ ID NO:1, 12, 13 and 61 with at least one of activity of a gamma-class PLP enzyme and an activity substantially equivalent to that of a lolC gene product,
  ii) a polynucleotide encoding a polypeptide comprising the sequence of any one of SEQ ID NO:2, 14, 15 and 62 or a variant thereof with at least 40% identity to any one of SEQ ID NO:2, 14, 15 and 62 with at least one of activity of an alpha-class PLP enzyme and activity substantially equivalent to that of the lolD gene product,
  iii) a polynucleotide encoding a polypeptide comprising the sequence of any one of SEQ ID NO:3, 16, 17 and 63 or a variant thereof with at least 40% identity to of any one of SEQ ID NO:3, 16, 17 and 63 with at least one of monooxygenase activity and activity substantially equivalent to that of the lolF gene product,
  iv) a polynucleotide encoding a polypeptide comprising the sequence of any one of SEQ ID NO:4, 18 and 19 or a variant thereof with at least 40% identity of any one of SEQ ID NO:4, 18 and 19 with at least one of amino acid bridging activity and activity substantially equivalent to that of the lolA gene product.
  v) a polynucleotide encoding a polypeptide comprising the sequence of any one of SEQ ID NO:5, 20, 21 and 64 or a variant thereof with at least 40% identity to of any one of SEQ ID NO:5, 20, 21 and 64 with at least one of activity of an alpha-class PLP enzyme and activity substantially equivalent to that of the lolT gene product.
  vi) a polynucleotide encoding a polypeptide comprising the sequence of of any one of SEQ ID NO:6, 22, 23 and 65 or a variant thereof with at least 40% identity to of any one of SEQ ID NO:6, 22, 23 and 65 with at least one of activity of a non-heme iron dioxygenase and activity substantially equivalent to that of the lolE gene product.
  vii) a polynucleotide encoding a polypeptide comprising the sequence of any one of SEQ ID NO:7, 24, 25 and 66 or a variant thereof with at least 40% identity to any one of SEQ ID NO:7, 24, 25 and 66 with at least one of activity of a non-heme iron dioxygenase and activity substantially equivalent to that of the lolO gene product,
  viii) a polynucleotide encoding a polypeptide comprising the sequence of any one of SEQ ID NO:8, 26 and 27 or a variant thereof with at least 40% identity to any one of SEQ ID NO:8, 26 and 27 with activity substantially equivalent to that of the lolU gene product,
  ix) a polynucleotide encoding a polypeptide comprising the sequence of SEQ ID NO:9 or 28 or a variant thereof with at least 40% identity to SEQ ID NO:9 or 28 with at least one of N-Methyltransferase activity and activity substantially equivalent to that of the lolM gene product,
  x) a polynucleotide encoding a polypeptide comprising the sequence of any one of SEQ ID NO:10, 29 and 67 or a variant thereof with at least 40% identity to any one of SEQ ID NO:10, 29 and 67 with at least one of acetamidase activity and activity substantially equivalent to that of the lolN gene product, and
  xi) a polynucleotide encoding a polypeptide comprising the sequence of SEQ ID NO: 11 or 30 or a variant thereof with at least 40% identity to SEQ ID NO:11 or 30 with at least one of cytochrome P450 monooxygenase activity and activity substantially equivalent to that of the lolP gene product.

In one embodiment the host cell is modified or transformed to comprise at least 2, preferably at least 3, more preferably at least 4, more preferably at least 5, more preferably at least 6, more preferably at least 7, more preferably at least 8, more preferably at least 9, more preferably at least 10, more preferably at least 11 polynucleotides selected from i) to xi)

In a further embodiment the host cell is modified or transformed to comprise the polynucleotides of i), ii), iii), v) and vii). That is the host cell is modified or transformed to comprise a lolC, lolF, lolD, lolT and a lolO gene, or polynucleotides encoding a lolC, lolF, lolD, lolT and a lolO gene product.

In a further embodiment the host cell contains more copies of the at least one polynucleotide than does a control cell.

In a further embodiment the host cell is not modified or transformed to comprise the polynucleotide of vi). That is the host cell is not modified or transformed to comprise a lolE gene, or a polynucleotide encoding a lolE gene product.

In a further embodiment the host cell is not modified or transformed to comprise the polynucleotide of viii). That is the host cell is not modified or transformed to comprise a lolU gene, or a polynucleotide encoding a lolU gene product.

In a further embodiment the host cell is not modified or transformed to comprise the polynucleotides of vi) or viii). That is the host cell is not modified or transformed to comprise a lolE or a lolU gene, or polynucleotides encoding a lolE or a lolU gene product.

In one embodiment the host cell produces more of at least one loline alkaloid or precursor thereof, than does a control cell.

In a further embodiment the host cell produces more of at least one loline alkaloid or precursor thereof, than does a control cell, as a result of the host cell being transformed or modified to comprise at least one polynucleotide.

In a further embodiment the control cell has not been modified or transformed to comprise the at least one polynucleotide.

In a further embodiment the control cell is of the same species or strain as the host cell that has been modified or transformed to comprise the at least one polynucleotide Host Cell where Polynucleotide is Part of an Expression Construct In a further embodiment the at least one polynucleotide is part of an expression construct.

In a further embodiment the at least one polynucleotide is operably linked to a promoter.

In a further embodiment the at least one polynucleotide is operably linked to a terminator.

In a further embodiment the at least one polynucleotide is operably linked to a promoter and a terminator.

Expression Construct

In a further aspect, the invention provides an expression construct comprising at least one polynucleotide selected from the group consisting of:

i) a polynucleotide encoding a polypeptide comprising the sequence of any one of SEQ ID NO:1, 12, 13 and 61 or a variant thereof with at least 40% identity to any one of SEQ ID NO:1, 12, 13 and 61 with at least one of activity of a gamma-class PLP enzyme and an activity substantially equivalent to that of a lolC gene product, ii) a polynucleotide encoding a polypeptide comprising the sequence of any one of SEQ ID NO:2, 14, 15 and 62 or a variant thereof with at least 40% identity to any one of SEQ ID NO:2, 14, 15 and 62 with at least one of activity of an alpha-class PLP enzyme and activity substantially equivalent to that of the lolD gene product, iii) a polynucleotide encoding a polypeptide comprising the sequence of any one of SEQ ID NO:3, 16, 17 and 63 or a variant thereof with at least 40% identity to of any one of SEQ ID NO:3, 16, 17 and 63 with at least one of monooxygenase activity and activity substantially equivalent to that of the lolF gene product, iv) a polynucleotide encoding a polypeptide comprising the sequence of any one of SEQ ID NO:4, 18 and 19 or a variant thereof with at least 40% identity of any one of SEQ ID NO:4, 18 and 19 with at least one of amino acid bridging activity and activity substantially equivalent to that of the lolA gene product, v) a polynucleotide encoding a polypeptide comprising the sequence of any one of SEQ ID NO:5, 20, 21 and 64 or a variant thereof with at least 40% identity to of any one of SEQ ID NO:5, 20, 21 and 64 with at least one of activity of an alpha-class PLP enzyme and activity substantially equivalent to that of the lolT gene product, vi) a polynucleotide encoding a polypeptide comprising the sequence of of any one of SEQ ID NO:6, 22, 23 and 65 or a variant thereof with at least 40% identity to of any one of SEQ ID NO:6, 22, 23 and 65 with at least one of activity of a non-heme iron dioxygenase and activity substantially equivalent to that of the lolE gene product.

vii) a polynucleotide encoding a polypeptide comprising the sequence of any one of SEQ ID NO:7, 24, 25 and 66 or a variant thereof with at least 40% identity to any one of SEQ ID NO:7, 24, 25 and 66 with at least one of activity of a non-heme iron dioxygenase and activity substantially equivalent to that of the lolO gene product, viii) a polynucleotide encoding a polypeptide comprising the sequence of any one of SEQ ID NO:8, 26 and 27 or a variant thereof with at least 40% identity to any one of SEQ ID NO:8, 26 and 27 with activity substantially equivalent to that of the lolU gene product, ix) a polynucleotide encoding a polypeptide comprising the sequence of SEQ ID NO:9 or 28 or a variant thereof with at least 40% identity to SEQ ID NO:9 or 28 with at least one of N-Methyltransferase activity and activity substantially equivalent to that of the lolM gene product, x) a polynucleotide encoding a polypeptide comprising the sequence of any one of SEQ ID NO:10, 29 and 67 or a variant thereof with at least 40% identity to any one of SEQ ID NO:10, 29 and 67 with at least one of acetamidase activity and activity substantially equivalent to that of the lolN gene product, and xi) a polynucleotide encoding a polypeptide comprising the sequence of SEQ ID NO:11 or 30 or a variant thereof with at least 40% identity to SEQ ID NO:11 or 30 with at least one of Cytochrome P450 monooxygenase activity and activity substantially equivalent to that of the 16/P gene product.

In one embodiment the expression comprises at least 2, preferably at least 3, more preferably at least 4, more preferably at least 5, more preferably at least 6, more preferably at least 7, more preferably at least 8, more preferably at least 9, more preferably at least 10, more preferably at least 11 polynucleotides selected from i) to xi).

In a further embodiment the expression construct comprises at least the polynucleotides of i), ii), iii), v) and vii). That is the construct comprises at least a lolC, lolF, lolD, lolT and a lolO gene, or at least polynucleotides encoding a lolC, lolF, lolD, lolT and a lolO gene product.

In a further embodiment the at least one polynucleotide is operably linked to at least one promoter.

In a further embodiment the expression construct does not comprise the polynucleotide of vi). That is the expression construct does not comprise a lolE gene, or a polynucleotide encoding a lolE gene product.

In a further embodiment the expression construct does not comprise the polynucleotide of viii). That is the expression construct does not comprise a lolU gene, or a polynucleotide encoding a lolU gene product.

In a further embodiment the expression construct does not comprise the polynucleotides of vi) or viii). That is the expression construct does not comprise a lolE or a lolU gene, or polynucleotides encoding a lolE or a lolU gene product.

Host Cell Comprising the Construct

In a further aspect the invention provides a host cell comprising at least one construct of the invention.

Those skilled in the art will understand that the desired complement of lol genes or polynucleotides may be present in one or multiple constructs that are transformed into the host.

In a preferred embodiment the at least one polynucleotide, or expression construct, is stably incorporated into the genome of the host cell.

Host Cell is Tolerant of ACPP Production

In a further embodiment the host cell is tolerant of endogenous (3-amino-3-carboxypropyl)proline (ACPP) production.

In a further embodiment the host cell has been pre-selected for tolerance to said level of cellular ACPP.

In a further embodiment the host cell has been pre-selected for tolerance of endogenous ACPP production by transformation with at least one polynucleotide encoding a polypeptide comprising the sequence of SEQ ID NO:1 or a variant thereof with at least 40% identity to SEQ ID NO:1 with at least one of activity of a gamma-class PLP enzyme and activity substantially equivalent to that of a lolC gene product.

In a further embodiment the host cell was supplied, or fed, with O-acetyl-L-homoserine (OAH) during selection. Preferably the host cell was supplied, or fed, with non-limiting amounts of OAH during selection.

In a further embodiment the host cell was supplied, or fed, with L-proline during selection. Preferably the host cell was supplied, or fed, with non-limiting amounts of L-proline during selection.

In a further embodiment the host cell is tolerant to at least 0.2 mM, more preferably at least 0.4 mM, more preferably at least 0.6 mM, more preferably at least 0.8 mM, more preferably at least 1 mM, more preferably at least 1.2 mM, more preferably at least 1.4 mM, more preferably at least 1.6 mM, more preferably at least 1.8 mM, more preferably at least 2 mM, more preferably at least 2.2 mM, more preferably at least 2.4 mM, more preferably at least 2.6 mM, more preferably at least 2.8 mM, more preferably at least 3 mM, more preferably at least 3.2 mM, more preferably at least 3.4 mM, more preferably at least 3.6 mM, more preferably at least 3.8 mM, more preferably at least 4 mM, more preferably at least 4.2 mM, more preferably at least 4.4 mM, more preferably at least 4.6 mM, more preferably at least 4.8 mM, more preferably at least 5 mM, more preferably at least 5.2 mM, more preferably at least 5.4 mM, more preferably at least 5.6 mM, more preferably at least 5.8 mM, more preferably at least 6 mM, more preferably at least 6.2 mM, more preferably at least 6.4 mM, more preferably at least 6.6 mM, more preferably at least 6.8 mM, more preferably at least 7 mM, more preferably at least 7.2 mM, more preferably at least 7.4 mM, more preferably at least 7.6 mM, more preferably at least 7.8 mM, more preferably at least 8 mM ACPP in the growth medium.

In a further embodiment host cell is tolerant of a level of cellular ACPP that is toxic to a control cell of the same strain or species.

Host Cell can Convert 1-AP to AcAP

In a further embodiment the host cell, prior to modification or transformation, is able to convert exo-1-aminopyrrolizidine (1-AP) to exo-1-acetamido-pyrrolizidine (AcAP).

In a further embodiment the host cell, prior to modification or transformation, has been pre-selected for the ability to convert 1-AP to AcAP.

In a further embodiment the host cell has been pre-selected by measuring AcAP production in the host cell.

In a further embodiment the host cell was supplied, or fed, with 1-AP during selection. Preferably the host cell was supplied, or fed, with non-limiting amounts 1-AP during selection.

In a further embodiment the selected host cell can produce at least 0.005 milligrams (mg), preferably 0.01 milligrams (mg), more preferably 0.02 milligrams (mg), more preferably 0.03 milligrams (mg), more preferably 0.04 milligrams (mg), 0.05 milligrams (mg), more preferably at least 0.1 mg, more preferably at least 0.15 mg, more preferably at least 0.2 mg, more preferably at least 0.25 mg, more preferably at least 0.3 mg, more preferably at least 0.35 mg, more preferably at least 0.4 mg, more preferably at least 0.45 mg, more preferably at least 0.5 mg, more preferably at least 0.75 mg, more preferably at least 1 mg, more preferably at least 1.5 mg, more preferably at least 2 mg of AcAP per gram (g) of cellular biomass.

Host Cell Type

In a further embodiment the cell is from a fungal species.

In a further embodiment the cell is from a bacterial species.

In a further embodiment the cell is from the subkingdom Dikarya.

In a further embodiment the cell is from a phylum selected from Chytridiomycota, Neocallimastigomycota, Blastocladiomycota, Glomeromycota, Ascomycota and Basidiomycota or a subphylum incertae sedis selected from Mucoromycotina, Kickxellomycotina, Zoopagomycotina and Entomophthoromycotina.

In a further embodiment the cell is from an order selected from Mucorales, Hypocreales, Eurotiales, Sebacinales and Saccharomycetales.

In a further embodiment the cell is from a genus selected from Metarhizium, *Epichloë*, *Saccharomyces*, *Kluveromyces*, *Trichoderma*, *Aspergillus*, *Beauveria*, *Pichia*, *Penicillium*, *Serendipita*, *Umbelopsis*, *Neurospora*, *Epicoccum*, *Sarocladium*, *Balansia*, *Fusarium*, *Alternaria*, *Ustilago*, *Sebacina*, *Glomus* and *Rhizopus*.

In a further embodiment the cell is from the species *Metarhizium robertsii*. In a further embodiment the cell is from the species *Trichoderma reesei*. In a further embodiment the cell is from the species *Aspergillus niger*. In a further embodiment the cell is from the species *Aspergillus nidulans*. In a further embodiment the cell is from the species *Aspergillus oryzae*. In a further embodiment the cell is from the species *Beauveria bassiana*. In a further embodiment the cell is from the species *Saccharomyces cerevisiae*. In a further embodiment the cell is from the species *Pichia pastoris*. In a further embodiment the cell is from the species *Kluveromyces marxianus*. In a further embodiment the cell is from the species *Epichloë festucae*. In a further embodiment the cell is from the species *Epichloë typhina*. In a further embodiment the cell is from the species *Penicillium chrysogenum*. In a further embodiment the cell is from the species *Penicillium paxilli*. In a further embodiment the cell is from the species *Penicillium expansum*. In a further embodiment the cell is from the species *Serendipita indica*. In a further embodiment the cell is from the species *Umbelopsis isabellina*. In a further embodiment the cell is from the species *Neurospora crassa*. In a further embodiment the cell is from the species *Epicoccum italicum*. In a further embodiment the cell is from the species *Sarocladium zeae*. In a further embodiment the cell is from the species *Fusarium verticillioides*. In a further embodiment the cell is from the species *Ustilago maydis*.

In one embodiment, the cell is a fungal cell other than a yeast cell.

In one embodiment the cell is a yeast cell.

In a further embodiment the cell is from a non-*Epichloë uncinata* fungal species.

Fermentation Suitable Host Cells

In a further embodiment the cell is from species or strain of fungi that is tractable to use in fermentation. In a further embodiment the cell is from a species or strain of fungi capable of a specific growth rate ($\mu$ h$^{-1}$) of at least 0.01, preferably 0.02, more preferably at least 0.03, more preferably at least 0.04, more preferably at least 0.05, more preferably at least 0.1, more preferably at least 0.15, more preferably at least 0.2, more preferably at least 0.25, more preferably at least 0.3, more preferably at least 0.35, more preferably at least 0.4, more preferably at least 0.45.

In a one embodiment the host cells suitable for fermentation is from a phylum selected from: Ascomycota and Basidiomycota or subphylum incertae sedis Mucoromycotina. In one embodiment the host cells suitable for fermentation are from a genus selected from: *Aspergillus, Beauveria, Epichloë, Neurospora, Epicoccum, Sarocladium, Kluveromyces, Metarhizium. Penicillium, Pichia, Rhizopus, Saccharomyces, Serendipita, Trichoderma*, and *Umbelopsis*.

In a one embodiment the host cells suitable for fermentation is from a species selected from: *Aspergillus niger, Aspergillus nidulans, Aspergillus oryzae, Beauveria bassiana, Epichloë festucae, Epichloë typhina, Epicoccum italicum, Metarhizium robertsii, Penicillium expansum, Penicillium chrysogenum, Penicillium paxilli, Saccharomyces cerevisiae, Kluveromyces marxianus, Pichia pastorus, Rhizopus oryzae, Rhizopus stolonifer, Rhizopus microsporus, Serendipita indica, Trichoderma reesei, Neurospora crassa, Sarocladium zeae* and *Umbelopsis isabellina*.

Method for Producing a Host Cell for Producing at Least One Loline Alkaloid, or Precursor Thereof In a further aspect the invention provides a method for producing a host cell for producing at least one loline alkaloid or precursor thereof, the method comprising modifying or transforming a host cell to comprise at least one polynucleotide as herein described.

In a further embodiment the host cell is produced by transforming a cell to comprise at least one polynucleotide or construct as herein described.

Method for Producing at Least One Loline Alkaloid or a Precursor Thereof

In a further aspect the invention provides a method for producing at least one loline alkaloid or a precursor thereof, the method comprising culturing host cells of the invention, or produced by a method of the invention, under conditions conducive to the production of the at least one loline alkaloid or precursor thereof, by the host cells.

In one embodiment the method further comprises separating, purifying, fractionating or isolating the at least one loline alkaloid or precursor thereof.

In a further embodiment the host cells are cultured in the presence of at least one loline alkaloid precursor.

In various embodiments the method comprises maintaining the host cells in the presence of at least one of:
(a) an effective amount of proline or a biosynthetic precursor thereof,
(b) an effective amount of O-acetyl-L-homoserine (OAH) or a biosynthetic precursor thereof,
(c) an effective amount of (3-amino-3-carboxypropyl) proline (ACPP) or a biosynthetic precursor thereof,
(d) an effective amount of exo-1-aminopyrrolizidine (1-AP) or a biosynthetic precursor thereof,
(e) an effective amount of exo-1-acetamido-pyrrolizidine (AcAP) or a biosynthetic precursor thereof, or
(f) any combination of two or more of (a) to (e) above.

In one embodiment the method comprises maintaining the host cells, or a culture thereof, at a temperature of from about 15° C. to about 35° C.

In a further embodiment the method comprises maintaining the host cells, or a culture thereof, at a temperature of from about 15° C. to about 40° C.

In one embodiment the method comprises maintaining the host cells, or a culture thereof, at for at least about 1 day, at least about 3 days, at least about 4 days, at least about 7 days or at least about 10 days.

In one embodiment the method comprises maintaining the host cells, or a culture thereof, in a bioreactor.

In one exemplary embodiment the method is a method of producing one or more loline alkaloids, comprising:
i) providing a culture comprising a host cell of the invention,
ii) maintaining the culture for at least about 1 day at a temperature of from about 15° C. to about 40° C. in the presence of one or more of the following:
(a) an effective amount of proline or a biosynthetic precursor thereof,
(b) an effective amount of O-acetyl-L-homoserine (OAH) or a biosynthetic precursor thereof,
(c) an effective amount of (3-amino-3-carboxypropyl) proline (ACPP) or a biosynthetic precursor thereof,
(d) an effective amount of exo-1-aminopyrrolizidine (1-AP) or a biosynthetic precursor thereof,
(e) an effective amount of exo-1-acetamido-pyrrolizidine (AcAP) or a biosynthetic precursor thereof, or
(f) any combination of two or more of (a) to (e) above, and
iii) separating the one or more loline alkaloids from the culture, or at least partially purifying or isolating the one or more loline alkaloids, thereby to provide the one or more loline alkaloids.

In one embodiment the purification or isolation is achieved via filtration and/or column purification.

In one aspect the invention provides a method for conferring the ability to produce a loline alkaloid or a precursor thereof on an organism, the method comprising transforming the organism with an expression construct of the invention.

In one embodiment the organism, prior to transformation, does not produce the loline alkaloid or precursor thereof.

The cell as herein described may be part of an organism. Thus reference to a cell or host cell can be used interchangeably with reference to an organism or host organism.

In one embodiment the loline alkaloid or precursor thereof is toxic to a pest.

In one embodiment the pest is an insect.

The term "insect" includes, but not limited to, aphids, mealybugs, whiteflies, moths, butterflies, psyllids, *thrips*, stink bugs, rootworms, weevils, leafhoppers and fruit flies, such as *Myzus persicae* (green peach aphid), *Aphis gossypii*

Glover (melon/cotton aphid), *Rhopalosiphum maidis* (corn leaf aphid), *Aphis glycines* Matsumura (soybean aphid). *Brevicoryne brassicae* (cabbage aphid), *Anasa tristis* (squash bug); *Pseudococcus longispinus* (long tailed mealybug). *Pseudococcus calceolariae* (scarlet mealybug), *Pseudococcus viburni* (obscure mealybug), *Planococcus citri* (Citrus mealybug); *Trialeurodes vaporariorum* (greenhouse whitefly), *Bemisia tabaci* (silverleaf whitefly); *Plutella xylostella* (diamondback moth), *Citripestis sagittiferella* (citrus fruit moth), *Helicoverpa armigera* (tomato fruitworm or corn earworm). *Pectinophora gossypiella* (pink lollworm). *Phthorimaea operculella* (potato tuber moth), *Amyelois transitella* (Navel orangeworm), *Cydia pomonella* (codling moth), *Cnephasia jactatana* (black-lyre leafroller), *Epiphyas postvittana* (light-brown apple moth), *Grapholita molesta* (oriental fruit moth), *Ostrinia furnacalis* (Asian corn borer), *Ostrinia nubilalis* (European corn borer), *Scirpophaga excerptalis* (sugarcane top borer) *Diatraea saccharalis* (sugarcane borer), *Chilo plejadellus* (rice stalk borer). *Earias vitella* (spotted lollworm), *Earias insulana* (spiny lollworm), *Spodoptera frugiperda* (fall armyworm), *Spodoptera litura* (tobacco cutworm), *Melittia cucurbitae* (squash vine borer), *Teia anartoides* (painted apple moth), *Trichoplusia ni* (Cabbage looper); *Pieris rapae* (white butterfly); *Bactericera cockerelli* (tomato/potato psyllid), *Diaphorina citri* (Asian citrus psyllid), *Trioza erytreae* (African citrus psyllid); *Thrips obscuratus* (flower *thrips*), *Heliothrips haemorrhoidalis* (greenhouse *thrips*), *Thrips tabaci* (onion *thrips*), *Frankliniella williamsi* (Maize thrip); *Halyomorpha halys* (brown marmorated stink bug), *Oebalus pugnax* (rice stink bug), *Diabrotica virgifera virgifera* (western corn rootworm), *Diabrotica barberi* (northern corn rootworm), *Diabrotica undecimpunctata howardi* (southern corn rootworm), *Diabrotica virgifera zeae* (Mexican corn rootworm); *Pempheres affinis* (cotton stem weevil); *Nephotettix virescens* (green leafhopper), *Nilaparvata lugens* (brown planthopper); *Bactrocera tryoni* (Queensland fruit fly).

In one embodiment the pest is a non-insect pest.

In one embodiment the pest is a nematode.

The term "nematode" includes but is not limited to root-knot nematodes (*Meloidogyne* species), cyst nematodes (*Heterodera* and *Globodera* species), lesion nematodes (*Pratylenchus* species), reniform nematodes (*Rotylenchulus reniformis*), lance nematodes (*Hoplolaimus* species) and stem and bulb nematodes (*Ditylenchus* species).

Preferred LOL genes for use in various aspects and embodiments of the invention are lolC, lolD, lolF, lolT and lolO.

In certain embodiments the host cells and organisms are not transformed to express lolF. In certain embodiments the host cells and organisms and are not transformed to express lolU. In certain embodiments the host cells and organisms are not transformed to express lolE or lolU.

Any one or more of the following embodiments may relate to any of the aspects described herein or any combination thereof.

In will be appreciated that the polynucleotide may be an allelic variant, degenerate sequence, homologue or orthologue of the specified nucleotide sequences.

In various embodiments the variant polypeptide has at least 40%, more preferably at least 41%, more preferably at least 42%, more preferably at least 43%, more preferably at least 44%, more preferably at least 45%, more preferably at least 46%, more preferably at least 47%, more preferably at least 48%, more preferably at least 49%, more preferably at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% amino acid identity with the specified polypeptide sequences.

In various embodiments the polynucleotide variant comprises one or more alternative codons that code for the eventual translation of a polypeptide having at least 40%, more preferably at least 41%, more preferably at least 42%, more preferably at least 43%, more preferably at least 44%, more preferably at least 45%, more preferably at least 46%, more preferably at least 47%, more preferably at least 48%, more preferably at least 49%, more preferably at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% amino acid identity with the specified polypeptide sequences.

In various embodiments the polynucleotide variant having at least 40%, more preferably at least 41%, more preferably at least 42%, more preferably at least 43%, more preferably at least 44%, more preferably at least 45%, more preferably at least 46%, more preferably at least 47%, more preferably at least 48%, more preferably at least 49%, more preferably at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% nucleotide sequence identity to the specified polynucleotide sequence.

Polynucleotide and polypeptide sequence identity may also be calculated over the entire length of the overlap between a candidate and subject polynucleotide sequences using global sequence alignment programs for e.g., the Needleman-Wunsch global alignment program (Needleman and Wunsch, 1970). A full implementation of the Needleman-Wunsch global alignment algorithm is found in the needle program in the EMBOSS package (Rice, et al., 2000) which can be obtained from the World Wide Web at http://www.hgmp.mrc.ac.uk/Software/EMBOSS/. The European Bioinformatics Institute server also provides the facility to perform EMBOSS-needle global alignments between two sequences on line at http:/www.ebi.ac.uk/emboss/align/.

Alternatively, the GAP program may be used which computes an optimal global alignment of two sequences without penalizing terminal gaps (Huang, 1994).

A preferred method for calculating polynucleotide and polypeptide % sequence identity is based on aligning sequences to be compared using Clustal X (Jeanmougin, et al., 1998).

In one embodiment the genome of the untransformed (wild type) host cell does not prior to transformation with a construct of the invention comprise the one or more LOL genes. In another embodiment the genome of the untransformed (wild type) host cell does not prior to transformation with a construct of the invention comprise a gene homologous to the one or more LOL genes. In another embodiment the untransformed (wild type) host cell or does not prior to transformation with a construct of the invention express the one or more LOL genes.

In one embodiment the host cell, expression construct or polynucleotide comprises and/or expresses at least the
a) lolC gene,
b) lolC and lolD genes,
c) lolC, lolD and lolT genes,
d) lolC, lolD, lolT and lolF genes,
e) lolC, lolD, lolT, lolF and lolA genes,
f) lolC, lolD, lolT, lolF and lolE genes,
g) lolC, lolD, lolT, lolF, lolE and lolA genes,
h) lolC, lolD, lolT, lolF, and lolO genes,
i) lolC, lolD, lolT, lolF, lolA and lolO genes,
j) lolC, lolD, lolT, lolF, lolE and lolO genes,
k) lolC, lolD, lolT, lolF, lolA, lolE and lolO genes,
l) lolC, lolD, lolF, lolT, lolO, lolN and lolM genes,
m) lolC, lolD, lolF, lolT, lolO, lolA, lolN and lolM genes,
n) lolC, lolD, lolF, lolT, lolO, lolE, lolN and lolM genes,
o) lolC, lolD, lolF, lolT, lolO, lolE, lolA, lolN and lolM genes.
p) lolC, lolD, lolF, lolT, lolO, lolN, lolM and lolP genes,
q) lolC, lolD, lolF, lolT, lolA, lolO, lolN, lolM and lolP genes.
r) lolC, lolD, lolF, lolT, lolE, lolO, lolN, lolM and lolP genes, or
s) lolC, lolD, lolF, lolT, lolA, lolE lolO, lolN, lolM and lolP genes.
t) lolC, lolD, lolF, lolT lolA, lolE, lolO, lolN, lolM lolP and lolU genes.

In one embodiment the one or more LOL genes are derived from *Epichloë uncinata, Epichloë festucae, Epichloë coenophiala, Epichloë amarillans, Epichloë glyceriae, Epichloë canadensis, Epichloë brachyelytri, Epichloë aotearoae, Epichloë siegelli, Aktinsonella hypoxylon*, or *Penicillium expansum*.

In one embodiment the expression construct, genome or polynucleotide comprises, or the host cell expresses a gene encoding a heterologous acetyltransferase.

In another embodiment the genome of the untransformed (wild type) host cell comprises an endogenous acetyltransferase. In another embodiment the host cell expresses an endogenous acetyltransferase.

Promoters

In one embodiment one or more of the LOL genes are operably linked to a constitutive promoter. In various embodiments the promoter is the histone H3 promoter, the GAPDH promoter, the pna2/tpi hybrid promoter (*Aspergillus nidulans* or *Aspergillus niger*), the gpdA promoter (*Metarhizium, Aspergillus*, or *Serendipita*), the mbfA promoter, the trpC promoter (*Aspergillus nidulans*), the hexokinase-1 promoter (*Metarhizium robertsii*), the class I hydrophobin promoter (*Beauveria bassiana*) or any other constitutive promoter described herein.

In one embodiment one or more of the LOL genes are operably linked to an inducible promoter. In various embodiments the promoter is the alcA promoter, the alcR promoter, amyB promoter, the gas promoter, the glaA promoter, the niiA promoter, the cbhI promoter, the ctr4 promoter, the thiA promoter or any other inducible promoter described herein.

Those skilled in the art will understand that the different LOL genes may be operably linked to and/or expressed under the control of different promoters and/or terminators.

Loline Alkaloids

In one embodiment the loline alkaloid is selected from the group comprising N-acetylnorloline (NANL), norloline, loline, N-acetylloline (NAL), N-methylloline (NML), N-formylloline (NFL) and a combination of any two or more thereof.

In one embodiment the loline alkaloid or precursor thereof is selected from the group comprising N-acetylnorloline (NANL), norloline, loline, N-acetylloline (NAL), N-methylloline (NML), N-formylloline (NFL), (3-amino-3-carboxypropyl)proline (ACPP), exo-1-aminopyrrolizidine (1-AP), exo-1-acetamido-pyrrolizidine (AcAP), and a combination of any two or more thereof.

In one embodiment the loline alkaloid is selected from the group comprising N-acetylnorloline (NANL), norloline, loline, N-methylloline (NML), N-formylloline (NFL) and a combination of any two or more thereof.

In one embodiment the loline alkaloid or precursor thereof is selected from the group comprising N-acetylnorloline (NANL), norloline, loline, N-methylloline (NML), N-formylloline (NFL), (3-amino-3-carboxypropyl)proline (ACPP), exo-1-aminopyrrolizidine (1-AP), exo-1-acetamido-pyrrolizidine (AcAP), and a combination of any two or more thereof.

Other aspects of the invention may become apparent from the following description which is given by way of example only and with reference to the accompanying drawings.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

BRIEF DESCRIPTION OF THE DRAWINGS

The invention will now be described by way of example only and with reference to the drawings in which.

Figure 1:
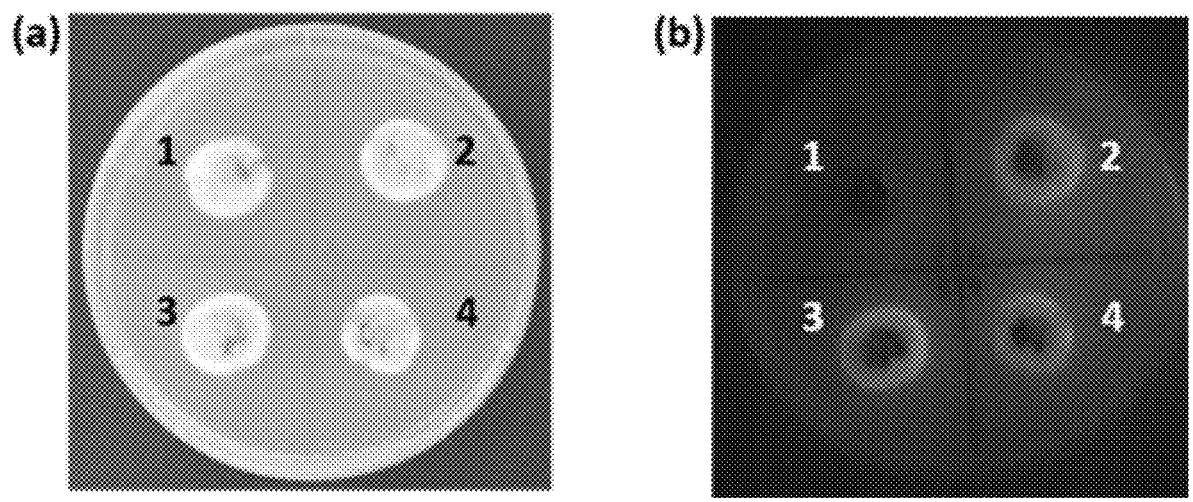
FIG. 1 (a) shows four transformant *M. robertsii* ARSEF 23 isolates cultured on M100 medium containing phosphinothricin observed under visible light, b) the same four transformant isolates observed under blue light. Note that isolate no. 1 is not fluorescent while isolates 2, 3, 4 fluoresce green.
Figure 2:
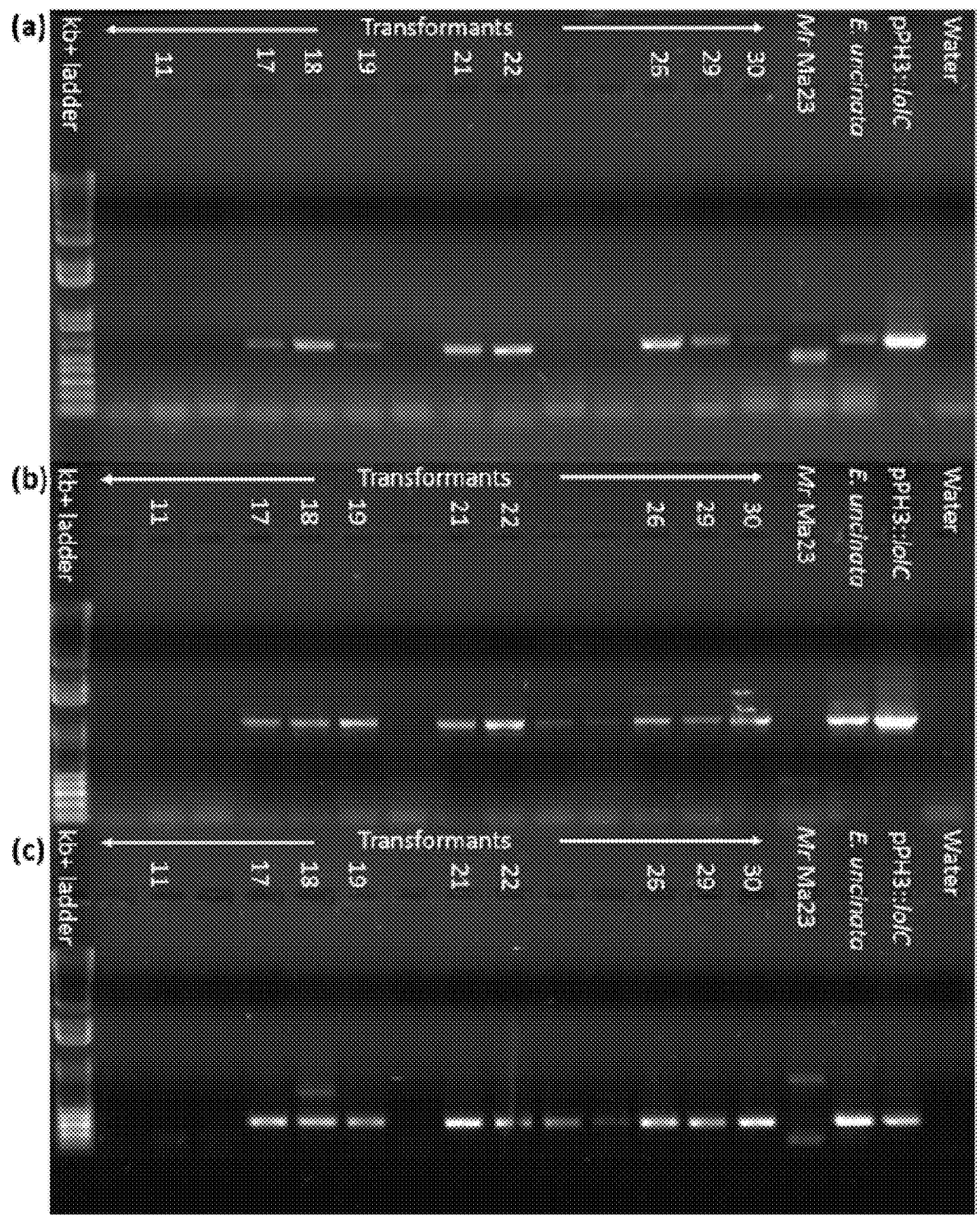
FIG. 2 shows an agarose gel photograph showing PCR amplification results with three sets of primers. Labelled in each gel are lanes carrying gDNA of isolates 17, 18, 19, 21, 22, 26, 29, and 30, which gave the correct band size indicating the presence of the *Epichloë* lolC gene, and the lane with gDNA of isolate 11, which went through the transformation process, but does not carry Epichloë lolC. pPH3-lolC and *Epichloë* gDNA were used as positive controls for lolC. *M. robertsii* ARSEF 23 (Mr Ma23) and water were the negative controls.

The present inventors have for the first time demonstrated production of lolines from heterologous expression of genes in the lolines biosynthetic pathway. This is the first pyrrolizidine alkaloid to be produced in any heterologous host.

As far as the inventors are aware, although there are numerous publications on lolines and loline genes, there is no publication reporting or even considering the production of lolines in a heterologous host.

While there have been some reports of heterologous expression of individual LOL genes, these studies relate to assessing gene function rather than any attempt to produce lolines.

Loline genes have only been reported in *Epichloë*, *Atkinsonella hypoxylon* and *Penicillium expansum*. In *Penicillium* and *Atkinsonella* the products of the LOL gene cluster are only predicted, and the cluster is missing some *Epichloë* LOL gene equivalents. Thus, there is no evidence to suggest that production of the lolines by *Epichloë* outside of *Epichloë* itself is possible.

Furthermore, ACPP, the product of the LolC enzyme, is reported to be toxic even to the producer fungus, even w % ben applied at relatively low amounts of 4 mM (Faulkner, et al., 2006). Heterologous expression of lolC (performed to attempt to complement a cystathionine synthase mutant) in *Aspergillus nidulans* was lost after a single subculture (Spiering, et al., 2005). In addition, attempts to express lolC in *E. coli* were unsuccessful (Schardl, et al., 2007) and the authors state that these results "suggest that lolC or its enzyme product is toxic to cells".

The toxicity of lolC or its enzyme product, thus makes the applicants successful production of lolines via the expression of LOL genes including lolC all the more surprising. The applicant's invention therefore additionally provides for pre-selection of strains tolerant to ACPP for use in the heterologous production of lolines.

In addition, the applicants have surprisingly shown that none of the reported LOL genes, perform the step of converting 1-AP to AcAP in heterologous hosts in their experiments. However, the applicants have surprisingly shown that this step can be performed by endogenous enzymatic activity present in some strains. The applicant's invention therefore additionally provides pre-selection of strains capable of performing the conversion of 1-AP to AcAP for use in the heterologous production of lolines.

1. Definitions

The term "and/or" can mean "and" or "or".

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

The term "polynucleotide(s)," as used herein, means a single or double-stranded deoxyribonucleotide or ribonucleotide polymer of any length but preferably at least 15 nucleotides, and include as non-limiting examples, genes, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments. The term also incudes fragments of polypeptides.

A "fragment" of a polynucleotide sequence provided herein is a subsequence of contiguous nucleotides.

The term "polypeptide", as used herein, encompasses amino acid chains of any length but preferably at least 5 amino acids, including full-length proteins, in which amino acid residues are linked by covalent peptide bonds. Polypeptides of the present invention, or used in the methods of the invention, may be purified natural products, or may be produced partially or wholly using recombinant or synthetic techniques. The term also incudes fragments of polypeptides.

A "fragment" of a polypeptide is a subsequence of the polypeptide that in some embodiments performs a function/activity of and/or influences three-dimensional structure of the polypeptide.

As used herein the term "gene" refers to a polynucleotide sequence or its complement that is involved in producing a polypeptide, including regions preceding (leader) and following (trailer) the coding sequence, and introns between individual coding sequence (exons). It also includes to a codon-optimised polynucleotide sequence of the native gene.

The term "constitutive promoter", as used herein, refers to a promoter that is not regulated and is active in all conditions in the host cell resulting in continuous transcription of its associated gene.

The term "inducible promoter", as used herein, refers to a promoter that is regulated and is active in the host cell only in response to specific stimuli resulting in transcription of its associated gene.

Figure 5:
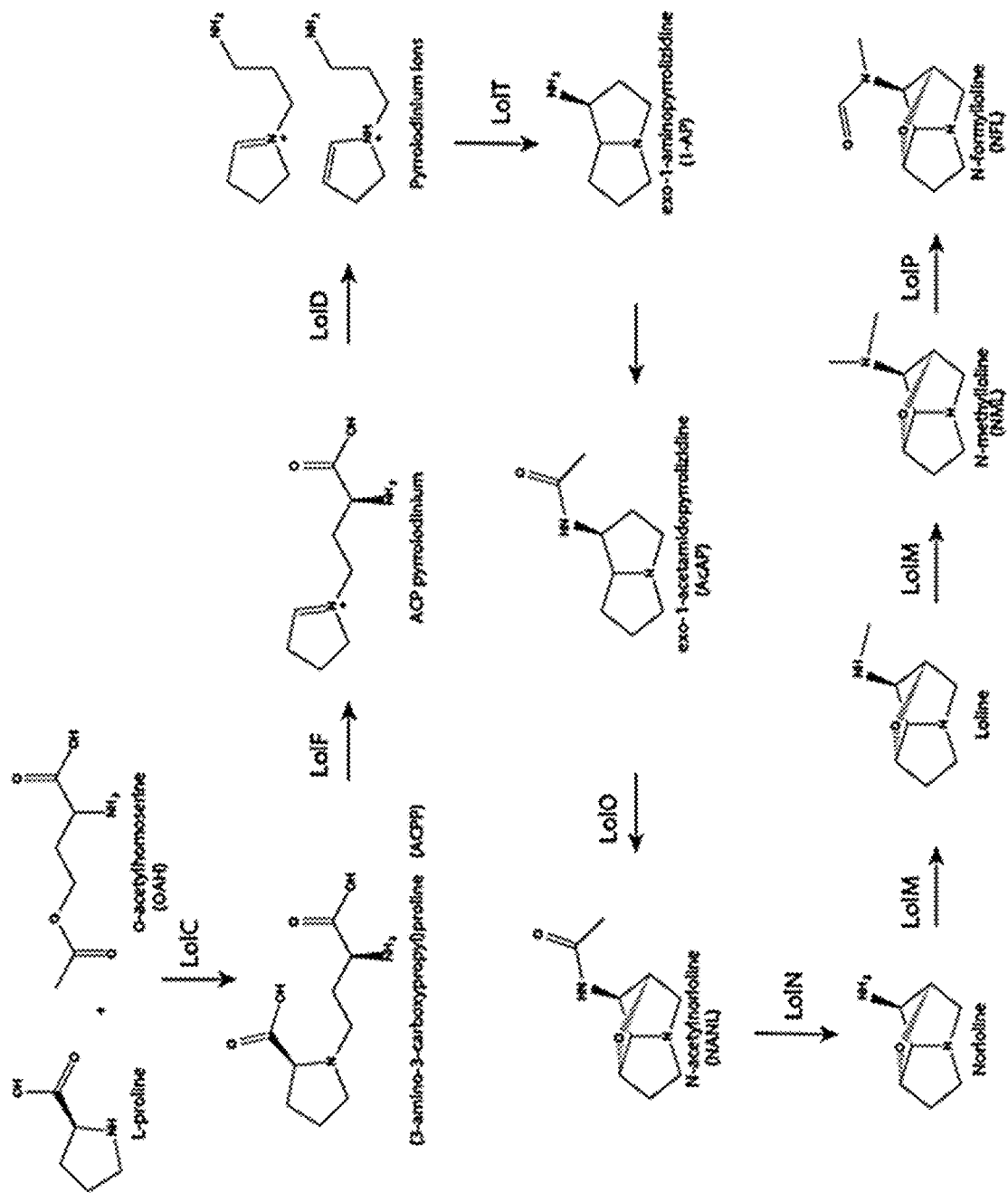
FIG. 5 shows the loline biosynthetic pathway (modified from (Pan, et al., 2014)). Condensation of L-proline and O-acetylhomoserine is the first committed step of the pathway resulting in formation of ACPP. The next chemically detectable intermediates are 1-AP and AcAP. NANL is the first fully cyclized intermediate that will then be converted to the array of lolines in the chemical arsenal against insects, lolU and lolE, genes present in the loline cluster, but with unknown function, are not shown here.

A "LOL gene" refers to any of the genes that encode an enzyme involved in catalysing a reaction in the loline biosynthetic pathway, as summarised in FIG. 5 and Table 1 and elsewhere in the specification. This includes any of lolC, lolA, lolT, lolO, lolE, lolN, lolM, lolP, lolU, lolD, or lolF, and/or any of the following polynucleotide sequences: SEQ ID NO. 31 to 60 and 68 to 74. The terms also encompass variants of these polynucleotide sequences as herein defined.

In various embodiment the term "LOL gene" encompasses a polynucleotide selected from the group consisting of:

i) a polynucleotide encoding a polypeptide comprising the sequence of any one of SEQ ID NO:1, 12, 13 and 61 or a variant thereof with at least 40% identity to any one of SEQ ID NO:1, 12, 13 and 61 with at least one of activity of a gamma-class PLP enzyme and an activity substantially equivalent to that of a lolC gene product, ii) a polynucleotide encoding a polypeptide comprising the sequence of any one of SEQ ID NO:2, 14, 15 and 62 or a variant thereof with at least 40% identity to any one of SEQ ID NO:2, 14, 15 and 62 with at least one of activity of an alpha-class PLP enzyme and activity substantially equivalent to that of the lolD gene product, iii) a polynucleotide encoding a polypeptide comprising the sequence of any one of SEQ ID NO:3, 16, 17 and 63 or a variant thereof with at least 40% identity to of any one of SEQ ID NO:3, 16, 17 and 63 with at least one of monooxygenase activity and activity substantially equivalent to that of the lolF gene product, iv) a polynucleotide encoding a polypeptide comprising the sequence of any one of SEQ ID NO:4, 18 and 19 or a variant thereof with at least 40% identity of any one of SEQ ID NO:4, 18 and 19 with at least one of aspartokinase activity and activity substantially equivalent to that of the lolA gene product, v) a polynucleotide encoding a polypeptide comprising the sequence of any one of SEQ ID NO:5, 20, 21 and 64 or a variant thereof with at least 40% identity to of any one of SEQ ID NO:5, 20, 21 and 64 with at least one of activity of an alpha-class PLP enzyme and activity substantially equivalent to that of the lolT gene product, vi) a polynucleotide encoding a polypeptide comprising the sequence of of any one of SEQ ID NO:6, 22, 23 and 65 or a variant thereof with at least 40% identity to of any one of SEQ ID NO:6, 22, 23 and 65 with at least one of activity of a non-heme iron dioxygenase and activity substantially equivalent to that of the lolE gene product, vii) a polynucleotide encoding a polypeptide comprising the sequence of any one of SEQ ID NO:7, 24, 25 and 66 or a variant thereof with at least 40% identity to any one of SEQ ID NO:7, 24, 25 and 66 with at least one of activity of a non-heme iron dioxygenase and activity substantially equivalent to that of the lolO gene product, viii) a polynucleotide encoding a polypeptide comprising the sequence of any one of SEQ ID NO:8, 26 and 27 or a variant thereof with at least 40% identity to any one of SEQ ID NO:8, 26 and 27 with activity substantially equivalent to that of the lolU gene product, ix) a polynucleotide encoding a polypeptide comprising the sequence of SEQ ID NO:9 or 28 or a variant thereof with at least 40% identity to SEQ ID NO:9 or 28 with at least one of N-Methyltransferase activity and activity substantially equivalent to that of the lolM gene product, x) a polynucleotide encoding a polypeptide comprising the sequence of any one of SEQ ID NO:10, 29 and 67 or a variant thereof with at least 40% identity to any one of SEQ ID NO:10, 29 and 67 with at least one of acetamidase activity and activity substantially equivalent to that of the lolN gene product, and xi) a polynucleotide encoding a polypeptide comprising the sequence of SEQ ID NO:11 or 30 or a variant thereof with at least 40% identity to SEQ ID NO:11 or 30 with at least one of cytochrome P450 monooxygenase activity and activity substantially equivalent to that of the lolP gene product.

In one embodiment a lolC gene comprises a polynucleotide encoding a polypeptide comprising the sequence of any one of SEQ ID NO:1, 12, 13 and 61 or a variant thereof with at least 40% identity to any one of SEQ ID NO:1, 12, 13 and 61.

Preferably the lolC gene or variant thereof has at least one of the activity of a gamma-class PLP enzyme encodes and an activity substantially equivalent to that of a lolC gene product.

In a further embodiment the lolD gene comprises a polynucleotide encoding a polypeptide comprising the sequence of any one of SEQ ID NO:2, 14, 15 and 62 or a variant thereof with at least 40% identity to any one of SEQ ID NO:2, 14, 15 and 62.

Preferably the polypeptide or variant thereof has at least one of the activity of an alpha-class PLP enzyme, and an activity substantially equivalent to that of the lolD gene product, In a further embodiment the lolF gene comprises a polynucleotide encoding a polypeptide comprising the sequence of any one of SEQ ID NO:3, 16, 17 and 63 or a variant thereof with at least 40% identity to of any one of SEQ ID NO:3, 16, 17 and 63.

Preferably the polypeptide or variant thereof has at least one of monooxygenase activity, and activity substantially equivalent to that of the lolF gene product, In a further embodiment the lolA gene comprises a polynucleotide encoding a polypeptide comprising the sequence of any one of SEQ ID NO:4, 18 and 19 or a variant thereof with at least 40% identity of any one of SEQ ID NO:4, 18 and 19.

Preferably the polypeptide or variant thereof has at least one of amino acid bridging activity and activity substantially equivalent to that of the lolA gene product.

In a further embodiment the lolT gene comprises a polynucleotide encoding a polypeptide comprising the sequence of any one of SEQ ID NO:5, 20, 21 and 64 or a variant thereof with at least 40% identity to of any one of SEQ ID NO:5, 20, 21 and 64.

Preferably the polypeptide or variant thereof has at least one of activity of an alpha-class PLP enzyme and activity substantially equivalent to that of the lolT gene product, In a further embodiment the lolE gene comprises a polynucleotide encoding a polypeptide comprising the sequence of of any one of SEQ ID NO:6, 22, 23 and 65 or a variant thereof with at least 40% identity to of any one of SEQ ID NO:6, 22, 23 and 65.

Preferably the polypeptide or variant thereof has at least one of activity of a non-heme iron dioxygenase and activity substantially equivalent to that of the lolE gene product.

In a further embodiment the lolO gene comprises a polynucleotide encoding a polypeptide comprising the sequence of any one of SEQ ID NO:7, 24, 25 and 66 or a variant thereof with at least 40% identity to any one of SEQ ID NO:7, 24, 25 and 66.

Preferably the polypeptide or variant thereof has at least one of activity of a non-heme iron dioxygenase and activity substantially equivalent to that of the 1610 gene product.

In a further embodiment the Jo/U gene comprises a polynucleotide encoding a polypeptide comprising the sequence of any one of SEQ ID NO:8, 26 and 27 or a variant thereof with at least 40% identity to any one of SEQ ID NO:8, 26 and 27.

Preferably the polypeptide or variant thereof has activity substantially equivalent to that of the lolU gene product.

In a further embodiment the lolM gene comprises a polynucleotide encoding a polypeptide comprising the sequence of SEQ ID NO:9 or 28 or a variant thereof with at least 40% identity to SEQ ID NO:9 or 28.

Preferably the polypeptide or variant thereof has at least one of N-Methyltransferase activity and activity substantially equivalent to that of the lolM gene product, In a further embodiment the lolN gene comprises a polynucleotide encoding a polypeptide comprising the sequence of any one of SEQ ID NO:10, 29 and 67 or a variant thereof with at least 40% identity to any one of SEQ ID NO:10, 29 and 67.

Preferably the polypeptide or variant thereof has at least one of acetamidase activity and activity substantially equivalent to that of the lolN gene product.

In a further embodiment the lolP gene comprises a polynucleotide polynucleotide encoding a polypeptide comprising the sequence of SEQ ID NO:11 or 30 or a variant thereof with at least 40% identity to SEQ ID NO:11 or 30.

Preferably the polypeptide or variant thereof has at least one of cytochrome P450 monooxygenase activity and activity substantially equivalent to that of the lolP gene product.

A "LOL gene product" refers to the polypeptide product of any of the genes, i.e. the encoded enzyme, involved in catalysing a reaction in the loline biosynthetic pathway, as summarised in FIG. 5 and Table 1 and elsewhere in the specification. The terms include any of lolC, lolA, lolT, lolO, lolE, lolN, lolM, lolP, lolU, lolD, or lolF polypeptides, and/or any of the following polypeptide sequences: SEQ ID NO. 1 to 30 and 61 to 67. The terms also encompass variants of these polypeptide sequences as herein defined.

The term "heterologous" as used herein with reference to a gene or a polynucleotide or polypeptide sequence transformed into or expressed by a host cell or fungus generally means a gene, or a polynucleotide or polypeptide sequence that is not encoded or expressed naturally by the wild type or native host cell or fungus.

The term "heterologous" as used herein with reference to polynucleotides, promoters and terminators, means that such heterologous sequences are not found operably linked to one another in wild type cells in nature. Thus, for example if a promoter is heterologous to the polynucleotide the promoter and polynucleotide are not found operably linked to one another in wild type cells in nature.

The term "host cell" as used herein refers to a fungal cell line cultured as a unicellular entity, which can be, or has been, used as a recipient for LOL genes, and/or expression constructs bearing one or more LOL genes, and/or which can be, or has been, transformed with or subjected to homologous recombination to integrate one or more heterologous LOL genes into the host cell genome. The term includes the progeny of the original host cell which has been transformed or subjected to homologous recombination. It will be appreciated that the progeny of a parent host cell may not be entirely identical in morphology or in genomic or total DNA complement to the original parent.

The term "plant" as used herein encompasses not only whole plants, but extends to plant parts, cuttings as well as plant products including roots, leaves, flowers, seeds, stems, callus tissue, nuts and fruit, bulbs, tubers, corms, grains, cuttings, root stock, or scions, and includes any plant material whether pre-planting, during growth, and at or post-harvest. Plants that may benefit from the application of the present invention cover a broad range of agricultural and horticultural crops, including crops produced using organic production systems.

The term "plant" includes those from any plant species. Such species include gymnosperm species, angiosperm species, and plants which belong to the superfamily Viridiplantae, in particular monocotyledonous and dicotyledonous plants. Such species include those that are used as fodder or forage crops, ornamental plants, food crops, row crops, horticultural crops, fruit crops, vegetable crops, biofuel crops, timber crops, and other trees or shrubs. Such species may be selected from the following: *Acer* spp., *Actinidia* spp., *Abelmoschus* spp., *Agave sisalana*, *Agropyron* spp., *Agrostis stolonifera*, *Allium* spp., *Amaranthus* spp., *Ammophila arenaria. Ananas comosus. Annona* spp., *Apium graveolens. Arachis* spp. *Artocarpus* spp., *Asparagus officinalis*, *Avena* spp. (*e.g. Avena sativa, Avena fatua, Avena byzantina, Avena fatua* var. *sativa, Avena hybrida*). *Averrhoa carambola, Bambusa* sp., *Benincasa hispida, Bertholletia excelsea, Beta vulgaris, Brassica* spp. (*e.g. Brassica napus, Brassica rapa* ssp. [canola, oilseed rape, turnip rape, kale]). *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus. Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (*e.g. Elaeis guineensis, Elaeis oleifera*), *Eleusine coracana, Eragrostis tef, Erianthus* sp., *Eriobotrya japonica, Eucalyptus* sp., *Eugenia unmflora, Fagopyrum* spp., *Fagus* spp., *Festuca arundinacea, Ficus carica, Fortunella* spp., *Fragaria* spp., *Ginkgo biloba, Glycine* spp. (*e.g. Glycine max, Soja hispida* or *Soja max*). *Gossypium hirsutum, Hehanthus* spp. (*e.g. Helianthus annuus*). *Hemerocallis fulva, Hibiscus* spp., *Hordeum* spp. (*e.g. Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (*e.g. Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (*e.g. Oryza sativa, Oryza latifolia*), *Panicum miliaceum, Panicum virgalum, Passiflora edulis, Pastinaca sativa, Pennisetum* sp., *Persea* spp., *Pelroselinum crispum, Phalaris arundinacea, Phaseolus* spp., *Phlewn pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica grananum, Pyrus communis, Quercus* spp., *Raphanus sativus, Rhewn rhabarbarum, Ribes* spp., *Ricinus communis, Rubus* spp., *Saccharum* spp., *SaNx* sp., *Sambucus* spp., *Secale cereale, Sesamum* spp., *Sinapis* sp., *Solanum* spp. (*e.g. Solanum tuberosum, Solanum betaceum, Solanum integrifoitum* or *Solanum lycopersicum*), *Sorghum bicolor, Spinacia* spp., *Syzygium* spp., *Tagetes* spp., *Tamarindus indica, Theobroma cacao, Trifolium* spp., *Tripsacum dactyloides, Triticosecale rimpaui, Triticum* spp. (*e.g. Triticum aestivum, Triticum durum, Triticum turgidum, Triticum hybernum, Trnticum macha, Triticum sativum, Triticum monococcum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris,* and *Ziziphus* spp., among others.

The term "loline alkaloid precursor" as used herein refers to compounds produced as intermediates in the loline biosynthetic pathway. Loline alkaloid precursors may comprise the product of reactions catalysed by the enzymatic product of expression of one or more LOL genes.

The term modified, modify, and grammatical variations thereof, with respect to modifying host cells, or fungi to comprise a polynucleotide, include editing the endogenous genome of the host cells or fungi.

Methods for modifying endogenous genomic DNA sequences are known to those skilled in the art. Such methods may involve the use of sequence-specific nucleases that generate targeted double-stranded DNA breaks in genes of interest.

Examples of such methods include: zinc finger nucleases (Curtin, et al., 2011, Sander, et al., 2011), transcription activator-like effector nucleases or "TALENs" (Cermak, et al., 2011, Mahfouz, et al., 2011, Li, et al., 2012), and LAGLIDADG homing endonucleases, also termed "meganucleases" (Tzfira, et al., 2012).

Targeted genome editing using engineered nucleases such as clustered, regularly interspaced, short palindromic repeat (CRISPR) technology, is an important new approach for generating RNA-guided nucleases, such as Cas9, with customizable specificities. Genome editing mediated by these nucleases has been used to rapidly, easily and efficiently modify endogenous genes in a wide variety of biomedically important cell types and in organisms that have traditionally been challenging to manipulate genetically. A modified version of the CRISPR-Cas9 system has been developed to recruit heterologous domains that can regulate endogenous gene expression or label specific genomic loci in living cells (Sander and Joung, 2014). The technique is applicable to fungi (Nodvig, et al., 2015).

The term "substantially equivalent" with reference to any given gene product, enzyme, protein, or polypeptide having activity substantially equivalent to that of any given LOL gene product, preferably means that the gene product, enzyme, protein, or polypeptide is capable of fulfilling the role of the LOL gene product as summarised in Table 1 below, and/or has the enzymatic activity listed in Table 1 below.

The term "control". "controlling", "biocontrol" or "biological control" are used interchangeably herein to refer to reduction in growth, growth rate, development, feeding rate, reproduction or number of pests, particularly plant pests, and/or reducing the severity of, or eliminating, symptoms of such pests, particularly symptoms in plants caused by such pests.

The term "(s)" following a noun contemplates the singular or plural form, or both.

2. Loline Alkaloid Biosynthesis

Loline alkaloids are produced symbiotically during infection of grasses by endophytes, particularly *Epichloë* endophytes (which, following a nomenclature realignment, now includes the previously separate anamorph *Neotyphodium* spp.). These endophytes are considered to be bioprotective, conferring pest, and possibly drought and disease protection to the symbionts of which they form part. Lolines are potent insecticidal compounds and contribute a substantial amount of the bioprotective benefit conferred by *Epichloë* species that produce them.

Loline alkaloids are 1-aminopyrrolizidines having an oxygen bridge between C2 and C7. The various loline alkaloid variants, namely N-acetylnorloline (NANL), norloline, loline, N-acetylloline (NAL), N-methylloline (NML), N-formylloline (NFL) are differentiated by substituents on the primary amine.

A loline alkaloid biosynthesis pathway has been proposed as shown in FIG. 5.

A loline alkaloid biosynthetic gene cluster has only been identified in fungi belonging to two clades in Pezizomycotina, namely Sordariomycetes (only *Epichloë* species and *Atkinsonella hypoxylon*) and Eurotiomycetes (only *Penicillium expansum*). The *Epichloë* LOL gene cluster comprises eleven genes, referred to as the LOL genes herein, encoding key enzymes in the loline alkaloid biosynthesis pathway. Homologs to seven of these genes have been reported in *P. expansum*. The LOL genes are summarised in Table 1 below.

TABLE 1

Summary of LOL genes.

| Gene | Predicted encoded enzymatic activity | Proposed Role | Polypeptide SEQ ID NO: | Polypeptide SEQ ID NO: | Species |
|---|---|---|---|---|---|
| lolC | gamma-class PLP | Formation of ACPP from OAH and proline | 1 | 31 | *E. festucae* |
| lolD | alpha-class PLP | Decarboxylation of pyrrolodinium ion | 2 | 32 | *E. festucae* |
| lolF | Monooxygenase | Oxidative decarboxylation of ACPP to form pyrrolodinium ion | 3 | 33 | *E. festucae* |
| lolA | Amino acid binding | Increasing the levels of OAH | 4 | 34 | *E. festucae* |
| lolT | alpha-class PLP | Cyclisation of pyrrolodinium ion(s) to form 1-AP | 5 | 35 | *E. festucae* |
| lolE | Nonheme iron dioxygenase | Not clear | 6 | 36 | *E. festucae* |
| lolO | Nonheme iron dioxygenase | Formation of the C2-C7 ether bridge in AcAP to form NANL | 7 | 37 | *E. festucae* |
| lolU | Not clear | Not clear | 8 | 38 | *E. festucae* |
| lolM | N-Methyltransferase | Methylation of norloline to form loline, and of loline to form NML | 9 | 39 | *E. festucae* |

TABLE 1-continued

Summary of LOL genes.

| Gene | Predicted encoded enzymatic activity | Proposed Role | Polypeptide SEQ ID NO: | Polypeptide SEQ ID NO: | Species |
|---|---|---|---|---|---|
| lolN | Acetamidase | Deacetylation of NANL to form norloline | 10 | 40 | E. festucae |
| lolP | Cytochrome P450 monooxygenase | Oxygenation of NML to form NFL | 11 | 41 | E. festucae |
| lolC1 | gamma-class PLP | Formation of ACPP from OAH and proline | 12 | 42 | E. festucae |
| lolC2 | gamma-class PLP | Formation of ACPP from OAH and proline | 13 | 43 | E. festucae |
| lolD1 | alpha-class PLP | Decarboxylation of pyrrolodinium ion | 14 | 44 | E. uncinata |
| lolD2 | alpha-class PLP | Decarboxylation of pyrrolodinium ion | 15 | 45 | E. uncinata |
| lolF1 | Monooxygenase | Oxidative decarboxylation of ACPP to form pyrrolodinium ion | 16 | 46 | E. uncinata |
| lolF2 | Monooxygenase | Oxidative decarboxylation of ACPP to form pyrrolodinium ion | 17 | 47 | E. uncinata |
| lolA1 | Amino acid binding | Increasing the levels of OAH | 18 | 48 | E. uncinata |
| lolA2 | Amino acid binding | Increasing the levels of OAH | 19 | 49 | E. uncinata |
| lolT1 | alpha-class PLP | Cyclisation of pyrrolodinium ion(s) to form 1-AP | 20 | 50 | E. uncinata |
| lolT2 | alpha-class PLP | Cyclisation of pyrrolodinium ion(s) to form 1-AP | 21 | 51 | E. uncinata |
| lolE1 | Nonheme iron dioxygenase | Not clear | 22 | 52 | E. uncinata |
| lolE2 | Nonheme iron dioxygenase | Not clear | 23 | 53 | E. uncinata |
| lolO1 | Nonheme iron dioxygenase | Formation of the C2-C7 ether bridge in AcAP to form NANL | 24 | 54 | E. uncinata |
| lolO2 | Nonheme iron dioxygenase | Formation of the C2-C7 ether bridge in AcAP to form NANL | 25 | 55 | E. uncinata |
| lolU1 | Not clear | Not clear | 26 | 56 | E. uncinata |
| lolU2 | Not clear | Not clear | 27 | 57 | E. uncinata |
| lolM | N-Methyl transferase | Methylation of norloline to form loline, and of loline to form NML | 28 | 58 | E. uncinata |
| lolN | Acetamidase | Deacetylation of NANL to form norloline | 29 | 59 | E. uncinata |
| lolP | Cytochrome P450 monooxygenase | Oxygenation of NML to form NFL | 30 | 60 | E. uncinata |
| lolC | gamma-class PLP | Formation of ACPP from OAH and proline | 61 | 68 | P. expansum |
| lolD | alpha-class PLP | Decarboxylation of pyrrolodinium ion | 62 | 69 | P. expansum |

TABLE 1-continued

Summary of LOL genes.

| Gene | Predicted encoded enzymatic activity | Proposed Role | Polypeptide SEQ ID NO: | Polypeptide SEQ ID NO: | Species |
|---|---|---|---|---|---|
| lolF | Monooxygenase | Oxidative decarboxylation of ACPP to form pyrrolodinium ion | 63 | 70 | P. expansum |
| lolT | alpha-class PLP | Cyclisation of pyrrolodinium ion(s) to form 1-AP | 64 | 71 | P. expansum |
| lolE | Nonheme iron dioxygenase | Not clear | 65 | 72 | P. expansum |
| lolO | Nonheme iron dioxygenase | Formation of the C2-C7 ether bridge in AcAP to form NANL | 66 | 73 | P. expansum |
| lolN | Acetamidase | Deacetylation of NANL to form norloline | 67 | 74 | P. expansum |

3. Expression Constructs and Host Cells

The host cells described herein comprise a genome encoding, expressing or having been transformed with one or more LOL genes or expression construct of the invention.

In various embodiments the expression construct of the invention comprises two or more or three or more LOL genes.

In various embodiments the one or more LOL genes are operably linked to one or more regulatory elements that control the transcription, translation or expression of the gene in a host cell transformed with the expression construct. The one or more regulatory elements may be contiguous with the one or more LOL genes or act in trans or at a distance to control the gene of interest.

Suitable regulatory elements include appropriate transcription initiation, termination, promoter and enhancer sequences, or RNA processing signals such as splicing or polyadenylation signals.

Examples of suitable promoters for use in fungal host cells include promoters which are homologous or heterologous to the host cell. Furthermore, suitable promoters for use in the expression constructs of the invention include constitutive promoters, regulatable promoters, inducible promoters or repressible promoters. The promoter may be derived from a gene of the host cell, or a promoter derived from the genes of other fungi, viruses or bacteria. Those skilled in the art will, without undue experimentation, be able to select promoters that are suitable for use in modifying and modulating expression constructs using genetic constructs comprising the LOL genes of the sequences described herein.

In embodiments where the expression construct comprises two or more LOL genes, or where the host cell comprises or has been transformed with two or more LOL genes, each gene may be under the control of the same promoter or different promoters.

In various embodiments the method comprises transforming the host cell with two or more, three or more, or four or more expression constructs of the invention.

Host cells may be transformed using suitable methods known in the art for achieving heterologous gene expression in fungi and/or yeast. Choice of transformation method will depend on the species and form of the host cell, and the number of expression constructs and or LOL genes to be transformed.

In one embodiment the method comprises transforming the host cell with an expression vector so that the one or more LOL genes is integrated into the genome of the host cell via homologous or non-homologous recombination.

In various embodiments the host cell comprises protoplasts, spheroplasts, spores or conidia.

In one embodiment the method comprises transforming the host cell using polyethylene glycol (PEG)-mediated transformation. Other suitable transformation methods include electroporation, Agrobacterium tumefaciens-mediated transformation, biolistic transformation, or non-PEG-mediated spheroplast transformation.

An exemplary method that may be used to achieve homologous recombination of one or more LOL genes into a fungal host cell genome using sequential transformations is that described by Chiang and co-workers (Chiang, et al., 2013).

Briefly, for genes that are very large and difficult to amplify by PCR, two smaller transforming fragments may be created that fuse by homologous recombination in vivo to reconstruct the full-length coding sequences under the control of a single promoter. Two or more LOL genes may be integrated into the host cell genome using sequential transformations. Each gene or transforming fragment carries a selectable marker to enable selection of transformants that are have been transformed with the gene. Marker recycling may be used so that many genes may be transferred easily into the host cell.

4. Production of Pyrrolizidine Alkaloids

In Vitro

Exemplary methods to produce and at least partially purify and/or isolate one or more of the loline alkaloids or of the invention are described herein. These include the at least partial purification and/or isolation of one or more loline alkaloids from a culture of one or more species, or from culture media or culture supernatants and the like obtained therefrom.

In one embodiment the method comprises maintaining a culture of host cells in the presence of one or more loline alkaloid precursors. For example, in various embodiments the culture is maintained in the presence of one or more of
a. an effective amount of proline or a biosynthetic precursor thereof,
b. an effective amount of O-acetyl-L-homoserine (OAH) or a biosynthetic precursor thereof,
c. an effective amount of (3-amino-3-carboxypropyl)proline (ACPP) or a biosynthetic precursor thereof,
d. an effective amount of aspartic acid or a biosynthetic precursor thereof,
e. an effective amount of exo-1-acetamido-pyrrolizidine (AcAP) or a biosynthetic precursor thereof,
f. an effective amount of exo-1-aminopyrrolizidine (1-AP) or a biosynthetic precursor thereof, or
g. any combination of two or more of (a) to (f) above.

Choice of culture conditions, including duration of culturing, temperature and/or culture media will depend upon the particular characteristics of the host cell.

The invention consists in the foregoing and also envisages constructions of which the following gives examples only and in no way limit the scope thereof.

EXAMPLES

Example 1: Heterologous Expression of lolC in Heterologous Hosts to Produce (3-amino-3-carboxypropyl)Proline (ACPP)

Background

The *Epichloë* LOL gene cluster, consisting of 11 genes, has been reported to be required for loline biosynthesis (Spiering, et al., 2005, Pan, et al., 2014). *Epichloë* lolC was predicted to encode the enzyme that catalyses the first committed step of the loline pathway—the condensation of L-proline with the 3-amino-3-carboxypropyl group from O-acetyl-L-homoserine (Faulkner, et al., 2006). The biosynthetic intermediate produced by this reaction has a dose-dependent effect in *E. uncinata*—it is toxic to cells when fed at 4 mM, but results in the enrichment of N-formylloline when fed to cultures at 2 mM. *P. expansum*, the only species outside the *Epichloë* clade known to carry the loline genes, has homologs to *Epichloë* lolC,D,F,T,E,O,N. There are no published studies characterizing *P. expansum* lolC (Pe lolC), but based on its similarity to *Epichloë* lolC, applicants expect that Pe lolC also encodes an enzyme that catalyzes the same reaction as *Epichloë* lolC (see Table 2 for amino acid percent identity between *E. festucae* and *P. expansum* loline gene products).

Figure 3:
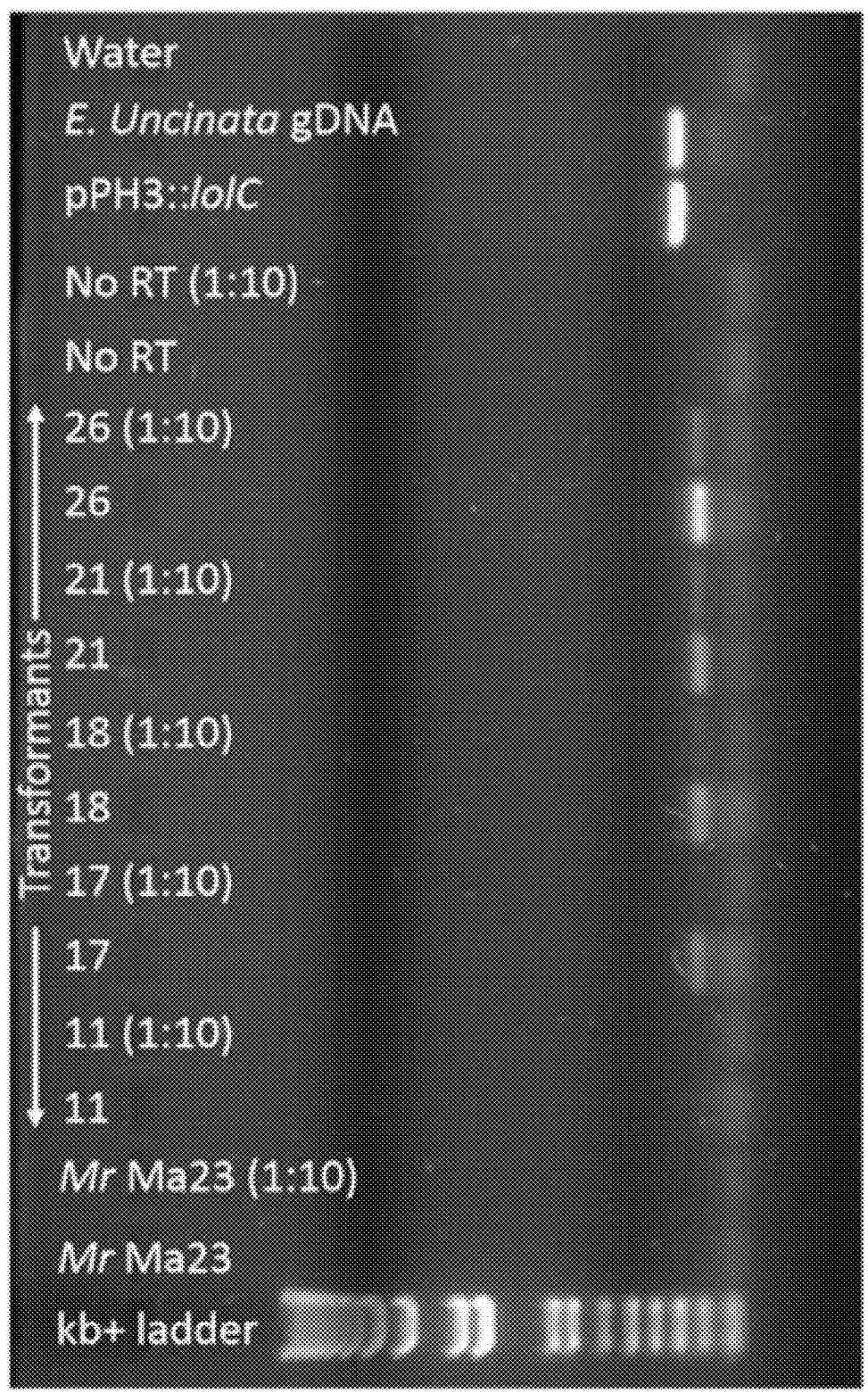
FIG. 3 shows an agarose gel photograph showing results of the PCR of cDNA of *M. robertsii* ARSEF 23 (Mr Ma23), transformant isolates and controls. PCR was done on undiluted and 1:10 diluted cDNA. Note the size difference between the band produced by gDNA (330 bp) and cDNA (285 bp).

The applicants considered that heterologous expression of lolC in fungi which do not possess the LOL gene cluster nor produce lolines, is an important first step towards transforming and expressing selected LOL genes in a non-*Epichloë* fungus, particularly in light of ACPP's reported toxicity. As initial proof of concept, *Epichloë festucae* lolC (Ef lolC) was expressed in *M. robertsii* ARSEF 23 and surprisingly the applicants were able to demonstrate that ACPP was produced. This is described in detail below. The applicants further individually expressed Ef lolC and Pe lolC with successful ACPP production in *B. bassiana*, *A. niger*, and *T. reesei. S. indica* was successfully transformed with Pe lolC, the next step will be confirming expression of lolC. A full summary of expression results of lolC and ACPP production in heterologous hosts is given in Table 5.

TABLE 2

Amino acid percent identity between proteins encoded by *E. festucae* and *P. expansum* loline genes

| Gene | Amino acid percent identity |
|---|---|
| lolC | 63.2% |
| lolD | 57.6% |
| lolF | 56.9% |
| lolT | 61.7% |
| lolE | 52.0% |
| lolO | 52.5% |
| lolN | 45.0% |

Protocol

A plasmid carrying *E. festucae* lolC gene (SEQ ID NO:31) fused to the constitutively expressed histone H3 promoter (pPH3-lolC) and a plasmid carrying phosphinothricin resistance and green fluorescence (pBAR-GFP) were co-transformed into competent protoplasts of *M. robertsii* strain ARSEF 23. Transformants carrying pBAR-GFP were selected based on their ability to grow on regeneration medium containing phosphinothricin and green fluorescence. Genomic DNA was extracted from the selected transformants, and presence of pPH3-lolC was confirmed through amplification of Ef lolC in three sets of polymerase chain reactions (PCR).

Two parallel approaches were taken in order to analyse Ef lolC expression and activity in *M. robertsii*. Firstly, RNA was extracted from four transformed *M. robertsii* isolates carrying Ef lolC, an isolate that was subjected to the transformation process but does not carry lolC, and the parental strain *M. robertsii* ARSEF 23, with the aim of observing Ef lolC transcription via RNA extraction, cDNA synthesis, and PCR Secondly, the same strains (above) were grown on M100 medium, freeze-dried, and analysed by liquid chromatography coupled with tandem mass spectrometry (LC-MS/MS) for presence of (3-amino-3-carboxypropyl)proline (ACPP), the suggested product of condensation of L-proline and O-acetyl-L-homoserine (OAH), in the transformant mycelium or medium, indicating the activity of the Ef lolC-encoded enzyme.

Results

Co-Transformation and Identification of Ef lolC Transformants

Thirty (30) transformant isolates that exhibited both phosphinothricin resistance and green fluorescence (a representative set of transformants shown in FIG. 1) were obtained from the co-transformation and selection processes.

Three sets of PCRs, which were done using three different primer combinations on genomic DNA (gDNA) of a subset of the transformants isolated above, identified and confirmed transformants carrying the pPH3-lolC (FIG. 2). Of the transformant isolates that gave a positive result indicating presence of the lolC gene in all three PCRs, isolates 17, 18, 21, and 26 were used for RNA extraction and chemical analysis. Parent strain *M. robertsii* ARSEF 23 and transformant isolate 11, which did not produce a band in all three PCRs were used as negative controls in the same experiments.

Transcription of the Ef lolC Gene

Total RNA extracted from *M. robertsii* ARSEF 23 and transformant isolates 11, 17, 18, 21, 26 were used for complementary DNA (cDNA) synthesis. In a PCR done using two primers designed to complement two consecutive exons that were separated by an intron, cDNA of transformant isolates 17, 18, 21, 26, produced a 245 bp band, while the pPH3-lolC and gDNA produced a 330 bp band. The size difference between the bands produced by cDNA and gDNA matched the size of the intron, indicating Ef lolC was transcribed to RNA and correctly spliced in transformant isolates 17, 18, 21, and 26. *M. robertsii* ARSEF 23 and isolate 11, both not carrying Ef lolC as well as controls done with water and without any reverse transcriptase (RT) enzyme during cDNA synthesis did not give any bands (FIG. 3).

Chemical Analysis of Ef lolC Transformants

Figure 4:
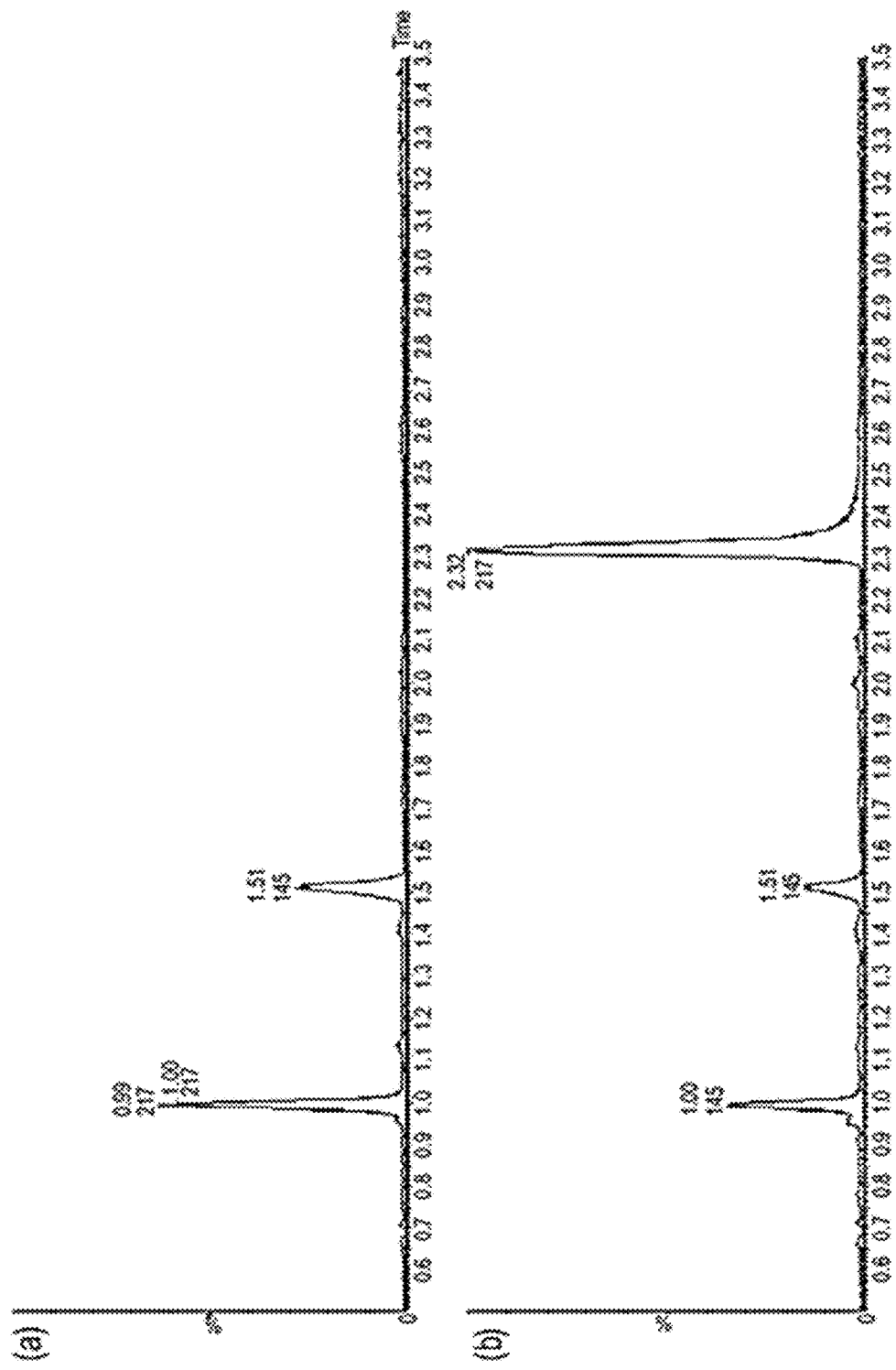
FIG. 4 (a) shows a typical extracted chromatogram for m/z 217 of *M. robertsii* ARSEF 23 and isolate 11, a transformant that lacks *E. festucae* lolC, but carries the same selectable marker as the *E. festucae* lolC transformants; (b) shows a typical extracted chromatogram for m/z 217 of four transformant isolates, all of which carry *E. festucae* lolC. Note the presence of the third peak that corresponds to ACPP in (b).

When analysed at m/z 217 (the protonated mass of ACPP), parental strain *M. robertsii* ARSEF 23 and transformant isolate 11, which did not carry pPH3-lolC, produced two peaks (FIG. 4a). Transformant isolates 17, 18, 21, and 26, carrying pPH3-lolC, gave three peaks (FIG. 4*b*). This result was consistent across all biological replicates of each isolate. The growth medium (M100) and the fungicide Sporekill™ (ICA International Chemicals Ltd., active ingredient Didecyldimethylammonium chloride), which was used to make the cultures non-viable, did not produce any peaks (see Table 3 for a list of peak areas for all samples).

Fragmentation analysis of the third peak present in the chromatograms of Ef lolC-expressing isolates matched those with a compound structurally similar to ACPP. This confirmed that the EF lolC transcript was translated to its functional enzymatic form, which catalysed the condensation of proline and OAH to produce ACPP.

TABLE 3

Peak areas for the growth medium (M100), fungicide (Sporekill), and three biological replicates each for *M. robertsii* ARSEF 23 and transformant isolates 11, 17, 18, 21, and 26. [Note the inability to quantify the amount of (3-amino-3-carboxypropyl) proline as this analysis was performed in the absence of an authentic standard]

| Sample | RT 0.98 Peak Area | RT 1.51 Peak Area | RT 2.32 [(3-amino-3-carboxypropyl)proline] Peak Area |
|---|---|---|---|
| Sporekill 10% | 0 | 0 | 0 |
| M100 | 0 | 0 | 0 |
| Ma23-1 | 1170000 | 717000 | 0 |
| Ma23-2 | 887000 | 472000 | 0 |
| Ma23-3 | 1260000 | 733000 | 0 |
| C11-1 | 1860000 | 1130000 | 0 |
| C11-2 | 2150000 | 1520000 | 0 |
| C11-3 | 1610000 | 993000 | 0 |
| C17-1 | 2060000 | 1520000 | 999000 |
| C17-2 | 1110000 | 583000 | 869000 |
| C17-3 | 1430000 | 835000 | 913000 |
| C18-1 | 1040000 | 650000 | 209000 |
| C18-2 | 1020000 | 393000 | 242000 |
| C18-3 | 1230000 | 787000 | 209000 |
| C21-1 | 1100000 | 634000 | 5160000 |
| C21-2 | 1350000 | 799000 | 4920000 |
| C21-3 | 1120000 | 660000 | 5640000 |
| C26-1 | 1050000 | 573000 | 2270000 |
| C26-2 | 1340000 | 668000 | 2430000 |
| C26-3 | 1790000 | 1150000 | 3690000 |

The *E. festucae* lolC gene was heterologously expressed in *M. robertsii*. This was evidenced by the presence of Ef lolC in transformant gDNA, the presence of the correctly-spliced transcript, and the isolation of ACPP—the suggested end product of the reaction catalysed by the enzyme encoded by Ef lolC. This experimental report marks the first-ever documentation of successful stable heterologous expression of lolC in a non-*Epichloë* fungus, confirms its role in producing ACPP and demonstrates the potential for producing subsequent steps in the loline biosynthetic pathway, which was in doubt due to the previously suggested toxicity of ACPP.

Example 2: Production of Lolines and Loline Intermediates in Heterologous Hosts

Introduction

Lolines, which consist of a variable combination of N-acetylnorloline (NANL), N-formylloline (NFL), and N-acetylloline (NAL) in nature, are produced in planta by many endophytic *Epichloë* species (e.g. *E. festucae* E2368, *E. glyceriae* E2772, *E. uncinata* E167). These alkaloids protect their grass hosts from herbivorous insects, but do not show toxicity towards mammals (Jackson, et al., 1996, Wilkinson, et al., 2000, Schardl, et al., 2013). Blankenship and co-workers (Blankenship, et al., 2001) demonstrated that *E. uncinata* was able to make lolines in culture, which gave evidence that lolines—and the genes responsible—were of fungal origin. An as yet unidentified plant-encoded acetyl transferase converts loline to NAL, a later 'decorative' step that increases the diversity of lolines (Pan, et al., 2014).

In Epichloë, eleven genes (lolC, D, F, A, T, E, O, U, M, N, P) collectively known as the LOL gene cluster, are reported to be required for loline biosynthesis (see FIG. 5 and (Pan, et al., 2014)). Of these, lolC encodes the enzyme that catalyses the first committed step of the loline pathway—the condensation of primary metabolites L-proline and O-acetyl-L-homoserine (OAH), as previously predicted (Faulkner, et al., 2006, Schardl, et al., 2007). However, this was only conclusively demonstrated for the first time in a heterologous host by the applicants in Example 1.

Expression of the eleven genes in the *Epichloë* LOL cluster was predicted to lead to production of NFL, the end-point of the biosynthetic pathway. Alternatively, eight genes are predicted to be required for production of NANL, which can be converted to an array of lolines. While not predicted to be required for NANL biosynthesis per se, the additional expression of lolA is predicted to increase loline biosynthesis via increasing the biological availability of the precursor molecule OAH.

Outside the *Epichloë* clade, the loline genes have only been reported in *P. expansum* (Ballester, et al., 2015, Marcet-Houben and Gabaldon, 2016), wherein the products of the LOL gene cluster have only been predicted. In addition, the *P. expansum* LOL gene cluster is missing some *Epichloë* LOL gene equivalents and has homologs of seven of the *Epichloë* loline genes (lolC, D, F, T, E, O, N).

Production of NANL in a heterologous host in culture vs. production in *Epichloë* species, is industrially advantageous because of (1) the ability to use a fast-growing heterologous host in a fermenter for continuous mass production of lolines (vs. very little production per day of lolines in vitro and only during the stationary phase by the slow-growing *E. uncinata*), and (2) the ability to bias production towards individual loline analogues. Lolines have also proven to be very complex to produce via synthetic chemistry (Faulkner, et al., 2006, Cakmak, et al., 2011), thus favouring production via biological means.

The heterologous hosts tested in the reported experiments are (1) *E. festucae* Fl1, an *Epichloë* strain that does not possess the loline cluster; (2) *B. bassiana* strain K4B1, an insect pathogen which is also fermentation-compatible; (3) *A. niger* strain ATCC 1015, commonly used for industrial fermentation; (4) *T. reesei* strain RUT-C30 (ATCC 56765), commonly used for industrial fermentation; (5) *M. robertsii* ARSEF 23, an insect pathogen; (6) *Neurospora crassa*, a model fungus commonly used for genetic research; (7) *S. cerevisiae*, a model fungus commonly used for genetic research and industrial fermentation; (8) *S. indica*, a plant protective endophyte with a broad Angiosperm host range; and (9) *U. isabellina*, an endophyte. Fungi listed (1)-(7) belong to phylum Ascomycota, while (8) is a member of the phylum Basidiomycota and (9) is a Mucoromycota.

Materials and Methods

Fungal Strains

Strains used in this study and method of genetic transformation are listed in Table 4. All strains are stored at the Biotelliga laboratory at the University of Auckland, Auckland. New Zealand.

TABLE 4

Fungal strains, media, and transformation methods used in the current study

| Fungal strain | Media used | Method of genetic transformation |
|---|---|---|
| *A. niger* (ATCC 1015) | Wild type and hygromycin selection: potato dextrose (PD); Phosphinothricin selection: M100 | Protoplast transformation (standard methods) |
| *B. bassiana* K4B1 | Wild type: Sabouraud dextrose (SD); Sulfonyl urea, phosphinothricin, hygromycin selection: Czapeks Dox (CD); Geneticin selection: PD | Same as for *A. niger* |
| *E. festucae* Fl1 | Epichloë M100 | |
| *M. robertsii* ARSEF 23 | Wild type and phosphinothricin selection: M100 | |
| *N. crassa* (ICMP 7781) | Wild type: Vogel's medium N (VM); Phosphinothricin selection: fructose/glucose/sorbose (FGS) medium | Spore electroporation (Navarro-Sampedro, et al., 2007) |
| *S. cerevisiae* BY4743 (ATCC 201390) | Wild type: yeast pepetone dextrose (YPD) G418, uracil auxotroph selection: yeast synthetic defined medium (SD) | (Gietz and Schiesil, 2007) |
| *S. indica* (ATCC 204458) | Wild type and hygromycin selection: *Aspergillus* complete medium (ACM); For growth immediately prior to and selection after electroporation: *Aspergillus* minimal medium | Protoplast transformation (Zuccaro, et al., 2009) and Electroporation of hyphal fragments (Yadav, et al., 2010) |
| *T. reesei* RUT-C30 (ATCC 56765) | Wild type and hygromycin selection: PD; Phosphinothricin selection: M100 | Protoplasts generated as described (Penttila, et al., 1987, Gruber, et al., 1990) transformed by standard protoplast transformation methods |
| *U. isabellina* ICMP 22148 | Wild type and hygromycin selection: PD | (Zhang, et al., 2007) |

Genetic Constructs

A detailed list of transformation constructs is given in Table 11. In brief, all transformed *Epichloë* loline genes (SEQ ID NO:31 to 33 and 35 to 41) were cloned from *E. festucae* E2368, except for pBTL10 that, in addition to *E. festucae* lolD and lolF, contains *E. uncinata* lolA) coding sequence (from 'wild type lolA1'—SEQ ID NO 48), pBTL11 that, in addition to *E. festucae* lolC, lolD and lolF, contains *E. uncinata* lolA1 coding sequence (from 'wild type lolA1'—SEQ ID NO 48), pBTL15 that, in addition to *E. festucae* lolC, contains *E. uncinata* lolA1 coding sequence (from 'wild type lolA1'—SEQ ID NO 48), and pBTL57 that contains *E. uncinata* lolA1 coding sequence (from 'wild type lolA1'—SEQ ID NO 48). Modified open reading frames [i.e. exons only, codon optimized for *Neurospora crassa* (using the Codon Optimization Tool at the Integrated DNA Technologies website https://sg.idtdna.com/CodonOpt), and with an HA tag] were also used in some cases. All transformed *Penicillium* loline genes (SEQ ID NO:68 to 71 and 73) were cloned from *P. expansum* ICMP 8595. Loline genes were transformed either coupled with a constitutive promoter or with a constitutive promoter and terminator. In a few cases, the gene encoding the selectable marker was present in the same plasmid as the loline genes. In most, however, the appropriate selectable marker was co-transformed with the loline gene constructs. All transformants were selected in media with appropriate selection. PCR screening was done to test for the presence of the loline genes on gDNA preparations done according to standard DNA extraction (miniprep gDNA extraction).

RNA Extraction and qPCR

RNA was extracted from fungal mycelia using the TRIzol® reagent (Life Technologies) according to the manufacturer's protocol. RNA was either DNased with DNase I recombinant (Roche) and used for cDNA synthesis with iScript™ (Biorad) or was DNased and cDNA synthesised using the iScript™ gDNA Clear cDNA Synthesis kit (Biorad). qPCR was done as per standard Biotelliga laboratory protocol using SsoAdvanced™ Universal SYBR Green Supermix (Biorad).

Chemical Analysis

Production of relevant compounds (ACPP, 1-AP, AcAP, and lolines) by transformed fungi were detected with liquid chromatography coupled with tandem mass spectrometry (LC-MS/MS). The values of detected compounds are represented in micromolar (µM) and were calculated using the following formula:

Concentration in µM=(Concentration in µg/ml÷molecular weight)×1000

The molecular weights of the compounds are: 216 (ACPP), 126 (1-AP), 168 (AcAP), 182 (NANL), 154 (loline), and 182 (NFL).

Results

Expression of lolC Results in Production of ACPP in Heterologous Hosts

Of the non-*Epichloë* fungi tested, *A. niger*, *B. bassiana*, *M. robertsii*, and *T. reesei* produced ACPP constitutively in culture upon expression of Ef lolC (Table 5). *A. niger*, *B. bassiana*, and *T. reesei* also produced ACPP constitutively in culture upon expression of Pe lolC (Table 5). Pe lolC was not attempted to be transformed into *M. robertsii*. The ACPP of biological origin was identical to chemically synthesised ACPP. It was observed in typical extracted chromatograms for the protonated mass of ACPP (m/z 217) in transformants with lolC, compared to wild type and a transformant not carrying lolC, but with the same selectable marker (FIG. 4). *N. crassa* and *S. cerevisiae* did not produce ACPP although transcription of lolC was detected.

TABLE 5

Summary of observations of expression of lolC and ACPP production in heterologous hosts

| Fungus | Summary of transformed gene of interest | Plasmid number | Transcription of lolC | ACPP detected |
|---|---|---|---|---|
| *A. niger* ATCC 1015 | lolC (from *E. festucae* E2368) | pBTL6 | Yes | 149-322 µM |
| *A. niger* ATCC 1015 | lolC (from *P. expansum* ICMP 8595) | pBTL74 | Yes | 212-913 µM |
| *B. bassiana* K4B1 | lolC (from *E. festucae* E2368) | pBTL6 | Yes | 10-1390 µM |
| *B. bassiana* K4B1 | lolC (from *P. expansum* ICMP 8595) | pBTL74 | Yes | 476-1844 µM |
| *M. robertsii* ARSEF 23 | lolC (from *E. festucae* E2368) | pBTL6 | Yes | 7-180 µM |
| *N. crassa* ICMP 7781 | lolC (from *E. festucae* E2368) | pBTL6 | Yes | No ACPP detected |
| *N. crassa* ICMP 7781 | lolC (from *E. festucae* E2368, exons only, codon optimized for *N. crassa*, C-terminal HA tag) | Transformed as PCR product | Yes | No ACPP detected |
| *S. cerevisiae* BY4743 | lolC (from *E. festucae* E2368, exons only, codon optimized for *N. crassa*, C-terminal HA tag removed) | pBTL14 | No | No ACPP detected |
| *S. cerevisiae* BY4743 | lolC (from *E. festucae* E2368, exons only, codon optimized for *S. cerevisiae*, C-terminal HA tag) | pBTL13 | Yes | No ACPP detected |

TABLE 5-continued

Summary of observations of expression of lolC and ACPP production in heterologous hosts

| Fungus | Summary of transformed gene of interest | Plasmid number | Transcription of lolC | ACPP detected |
|---|---|---|---|---|
| S. cerevisiae BY4743 | lolC (from E. festucae E2368, exons only, codon optimized for S. cerevisiae, C-terminal HA tag removed) | Modified pBTL13 | No | No ACPP detected |
| T. reesei RUT-C30 | lolC (from E. festucae E2368) | pBTL6 | Yes | 2-17 µM |
| T. reesei RUT-C30 | lolC (from P. expansum ICMP 8595) | pBTL74 | Yes | 4-878 µM |

Expression of *Epichloë* Loline Pathway Genes Results in Loline Production in Heterologous Hosts Based on their ability to produce ACPP upon expression of lolC, heterologous hosts *A. niger*, *B. bassiana*, and *M. robertsii*, along with *E. festucae* F11, were selected as candidate heterologous hosts for expression of lolCDFAIT-EOU—or subsets of genes thereof. The lol genes transformed were obtained from *E. festucae* E2368, *E. uncinata* AR 1006 and/or *P. expansum* ICMP 8595. The industrial *A. niger* strain ATCC 1015, was transformed with *Epichloë* lolD. F,T,A,I,O. Cultures were supplemented with 1 mM ACPP, and upon feeding, successfully produced 0.385 µM NANL (Table 6).

Figure 6:
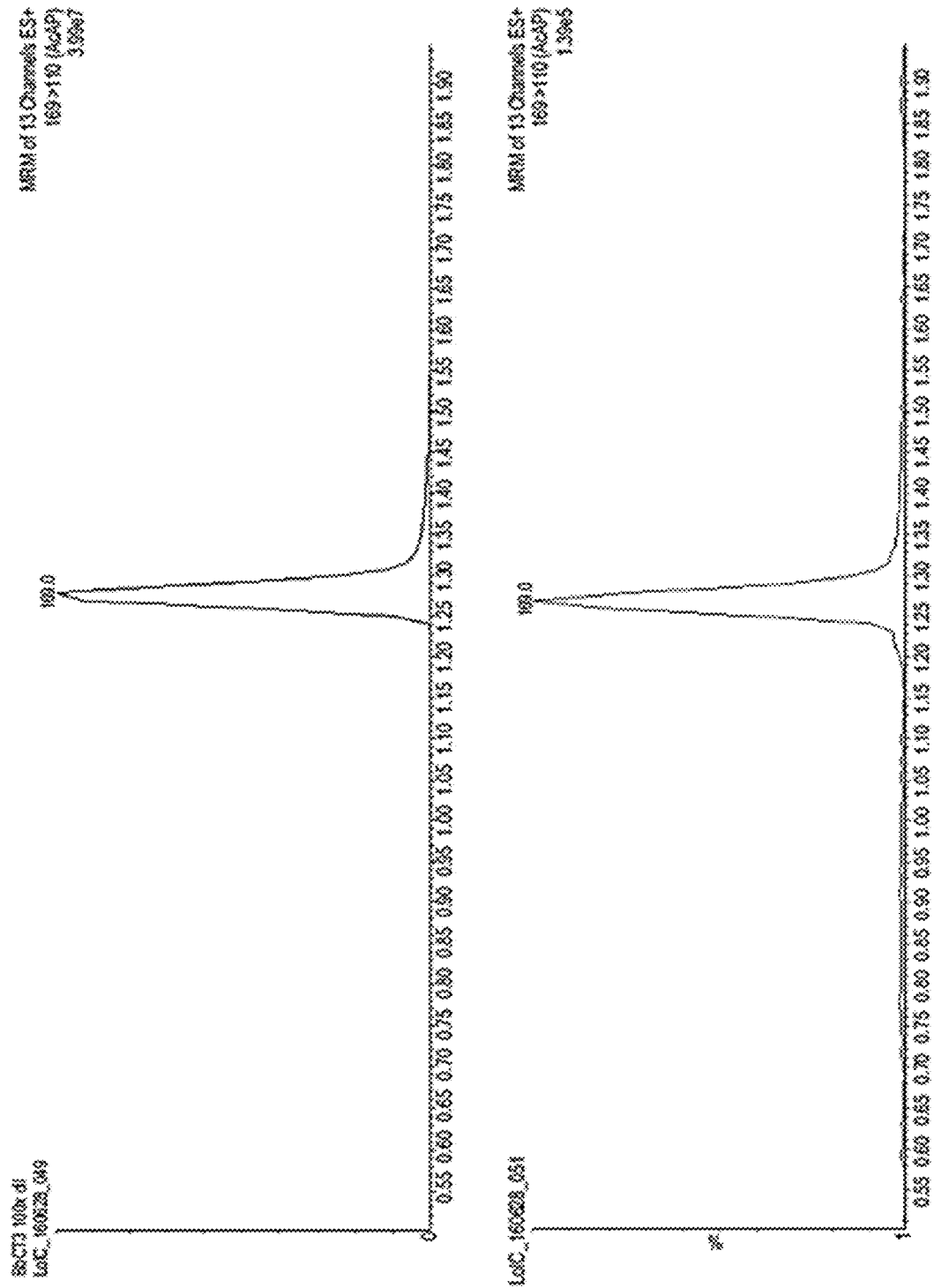
FIG. 6 shows a comparison of chromatograms of chemically-synthesized AcAP standard to the AcAP produced by *B. bassiana* 'Bb CT3' transformant carrying lolCDFA1TEU. Top: chromatogram of AcAP produced by Bb CT3 transformant; bottom: chromatogram of chemically-synthesized AcAP standard. Both chromatograms exhibit the same retention time and transition ( such host cells. The invention is also directed to recombinant methods for producing one or more loline alkaloids or precursors thereof by culturing a host cell described herein, and methods for producing, or conferring the ability to produce, one or more loline alkaloids to a host cell or organism. The lolines and precursors there of produced by the host cell, and methods of the invention are useful for controlling pests.
Figure 7:
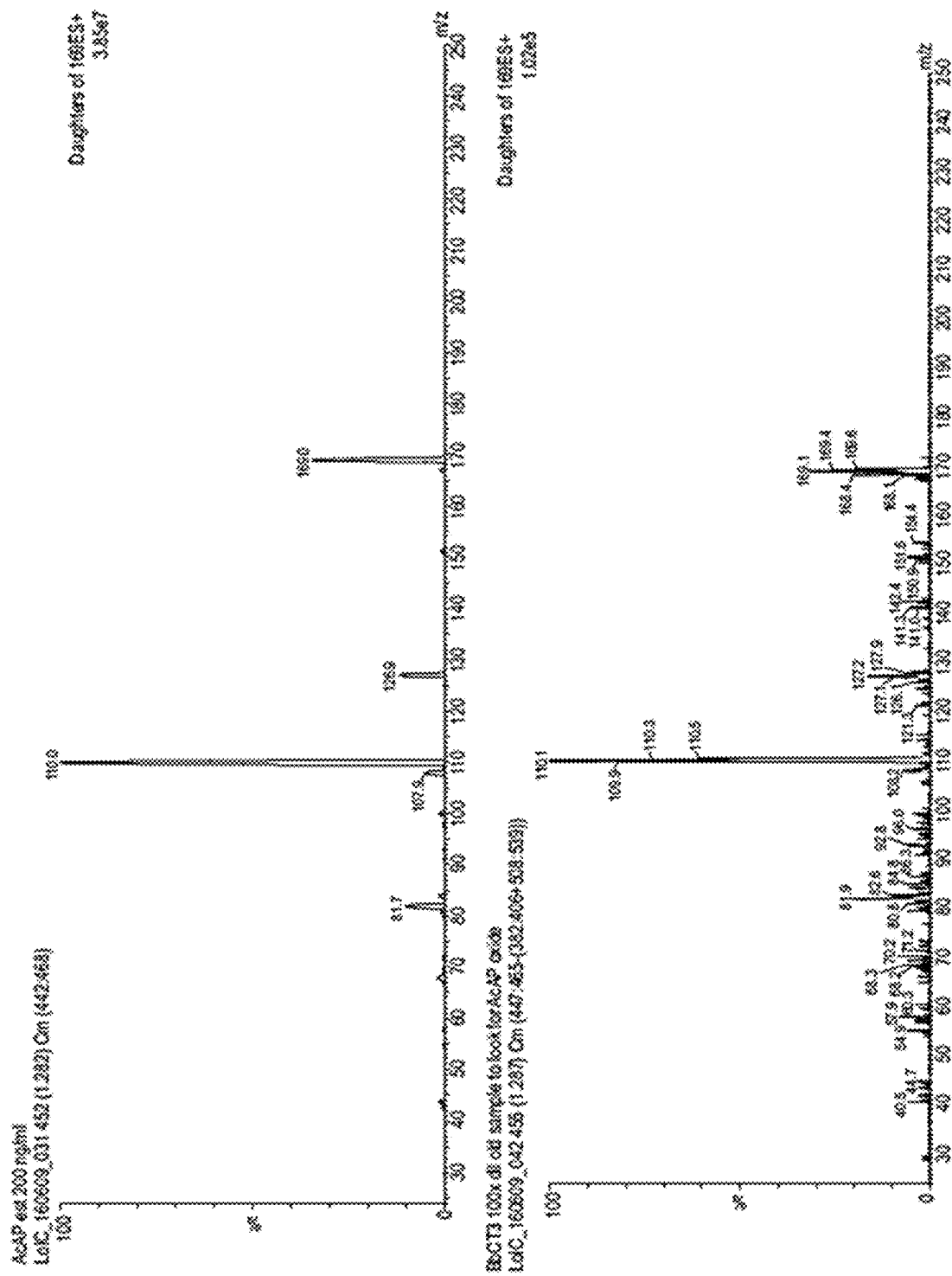
Figure 8:
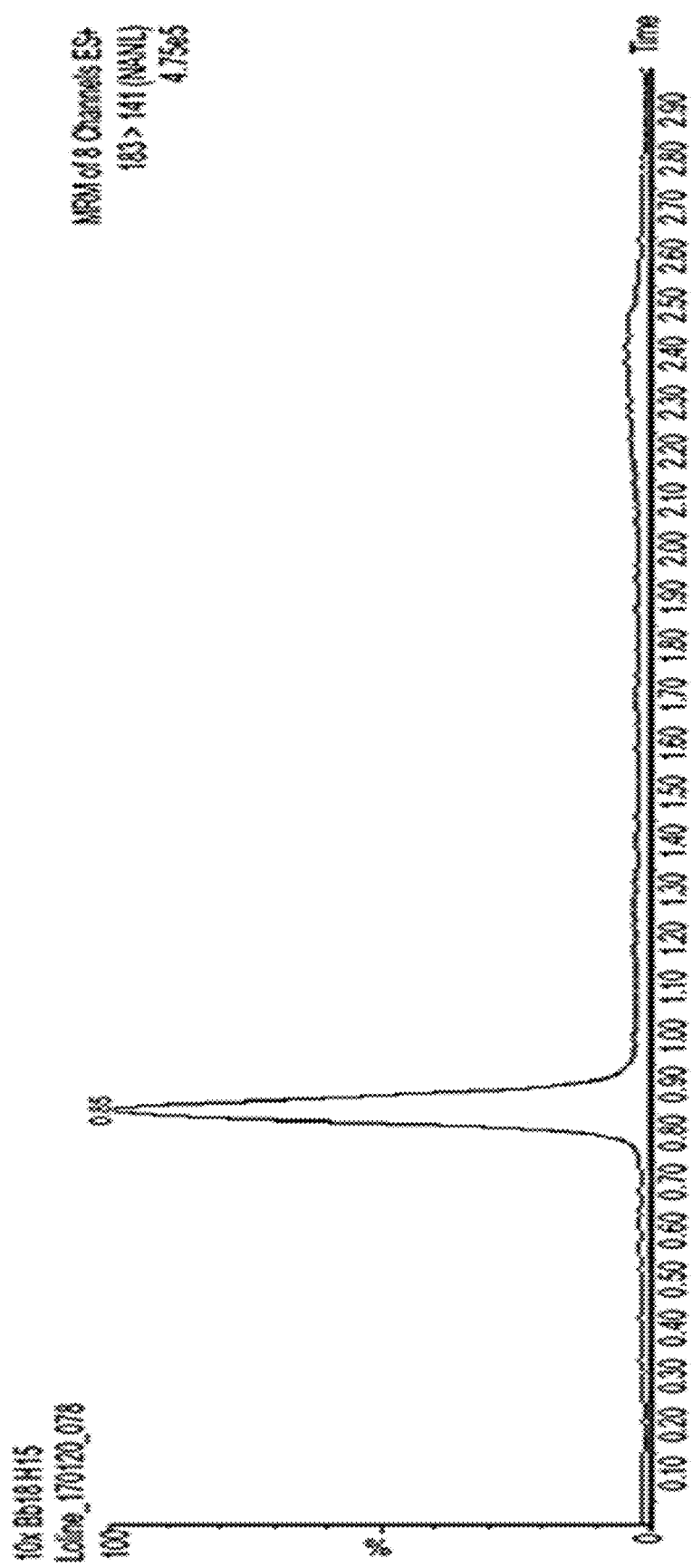
Figure 9:
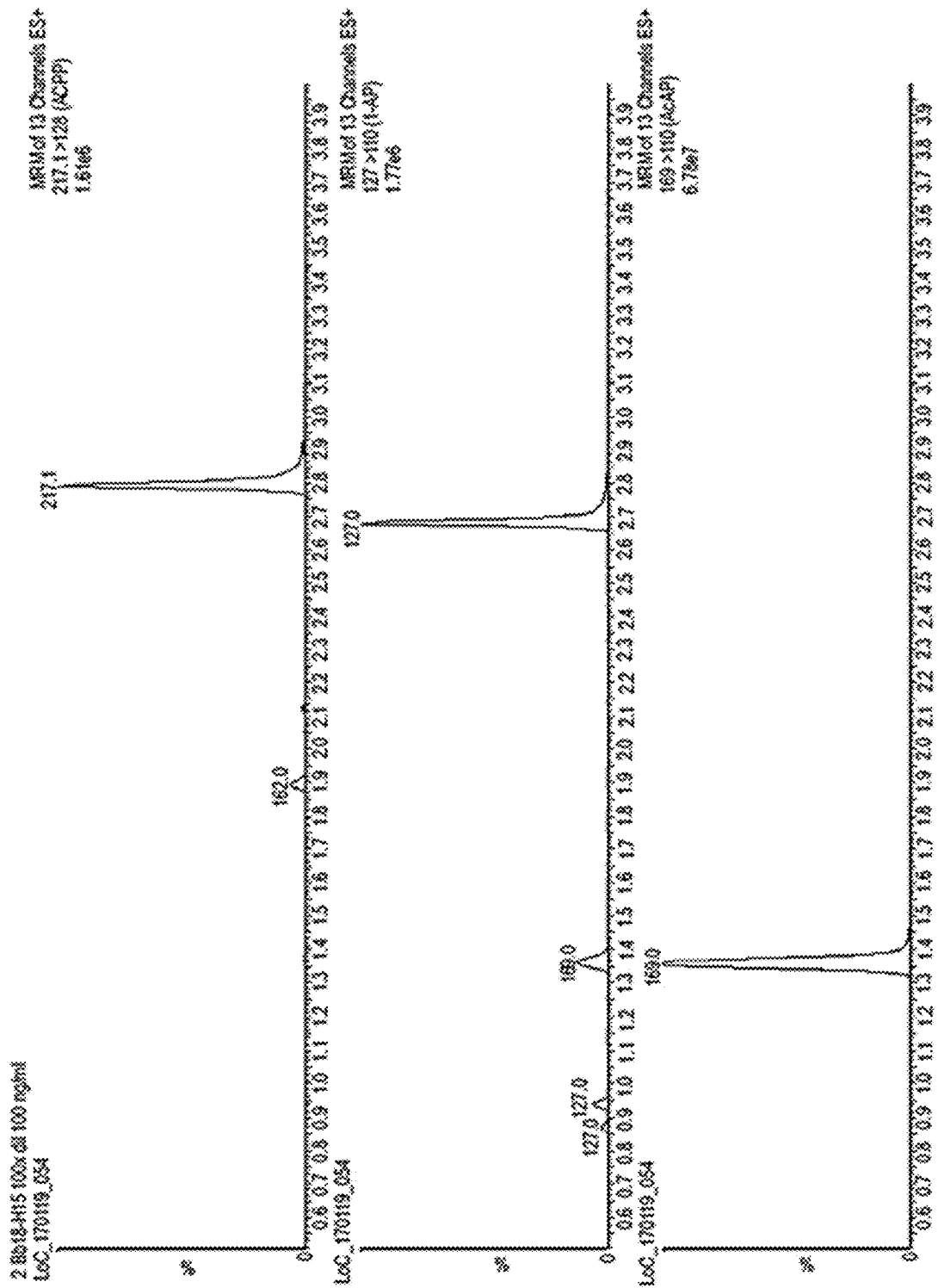
Figure 10:
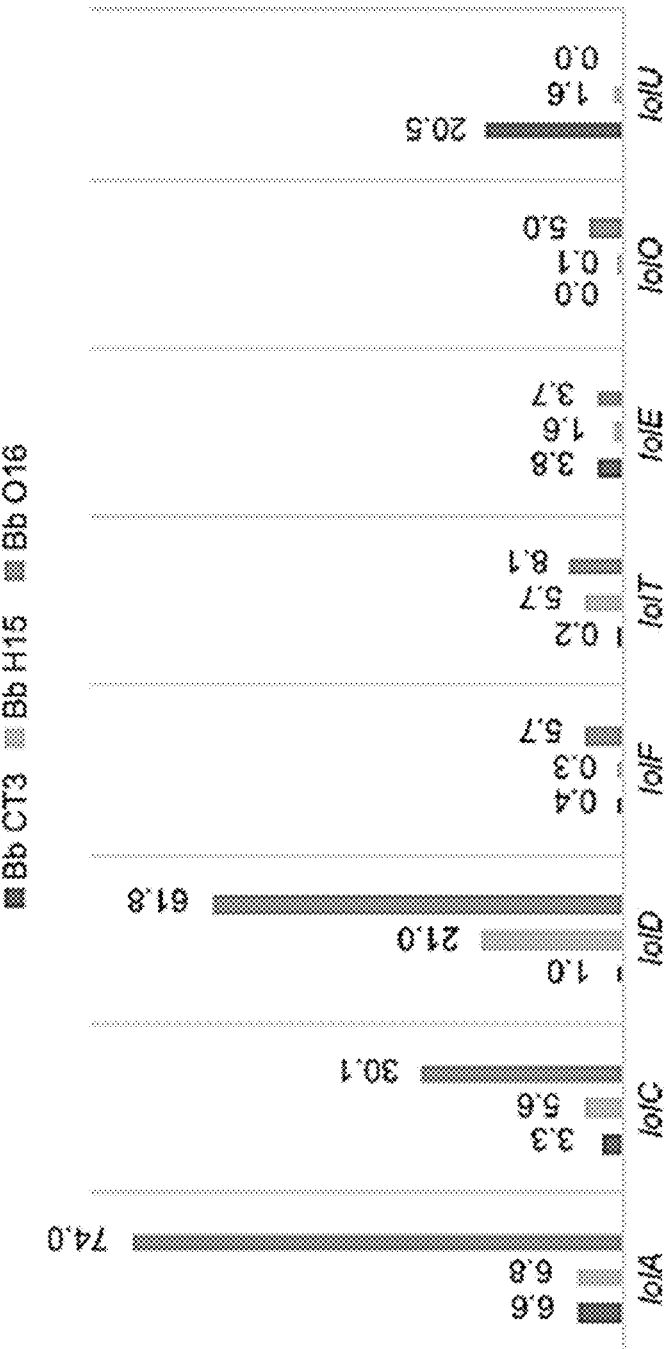

Transformation of *Epichloë* lolCDFA1TEU to *B. bassiana* resulted in production of 0.179 µM AcAP when fed with 2 mM ACPP (see FIGS. 6 and 7 for comparison of AcAP produced by the *Epichloë* lolCDFA1TEU-carrying transformant Bb CT3 to chemically synthesised AcAP). This may be indicative of the selection of a transformant with relatively weak gene expression, which may have been caused by exclusion of transformants with 'good' gene expression due to toxicity of pathway intermediates to the host. Transformation of *B. bassiana* with *Epichloë* lolCDFA1TEOU under selected promoters and terminators (see Table 11 for details of constructs) resulted in production of 0.385 µM NANL (see FIG. 8 for chromatogram), as well as the full complement of detectable intermediates post-ACPP (see FIG. 9 for chromatograms). Expression of *Epichloë* lolCDFA1TE-OUMNP in *B. bassiana* resulted in NFL and loline (see Table 6 for detailed summary of results). Gene expression levels of transformant isolate Bb4-18-H15 ('Bb H15') showed possible bottlenecks in the pathway due to relatively 'low' expression of lolF and lolO (FIG. 10). lolF and/or lolO, each under *E. festucae* F11 histone H3 promoter, shown to result in relatively high expression levels in our previous experiments, and followed by the glaA terminator, were transformed into Bb H15. Transformants carrying the additional copy of lolO (named isolate Bb O16) produced more NANL than parent Bb H15. When fed with 30 mM proline, 4 mM OAH, 2 mM alpha-ketoglutaric acid and 0.25 mM iron [in ammoniumiron(II)sulfate hexahydrate (Pan, et al., 2018)], this isolate, BbO16 produced the hightest amount of NANL observed in any heterologous host system to-date (5.49 µM NANL at 4 days post inoculation). Analysis of gene expression of the two isolates showed increased expression in all loline genes in Bb O16 compared to Bb H15 (FIG. 10).

TABLE 6

Summary observations of expression of Epichloë loline pathway genes and lolines and/or intermediates production in hosts tested positive for ACPP with lolC expression

| Fungus | Summary of transformed genes of interest | Plasmid number | Transcription of lol genes | Lolines and/or intermediates detected |
|---|---|---|---|---|
| A. niger ATCC 1015 | Ef lolDFTO, Eu lolA1 and Pe lolC | pBTL38, pBTI 32, pBTL40, pBTL57, pBTL33 | Transcripts of Ef lolDFTO detected. Pe lolC gene didn't integrate. | 0.385 µM NANL (in cultures fed with 1 mM ACPP) |
| B. bassiana K4B1 | Ef lolCDFTEOU and Eu lolA1 | pBTL11, pBTL12 | Yes, except for lolO (in pBTL12), which had a SNP and thereby truncated and non-functional. | 0.179 µM AcAP (in cultures fed with 2 mM ACPP, but not in cultures grown with precursors proline and OAH). See FIGS. 6 and 7 for chromatograms comparing synthetic vs. biologically-produced AcAP. |
| B. bassiana K4B1 | Ef lolCDFTEOU and Eu lol A1 | pBTL15, pBTL16, pBTL17 | Yes | 0.385 µM NANL |

TABLE 6-continued

Summary observations of expression of Epichloë loline pathway genes and lolines and/or intermediates production in hosts tested positive for ACPP with lolC expression

| Fungus | Summary of transformed genes of interest | Plasmid number | Transcription of lol genes | Lolines and/or intermediates detected |
|---|---|---|---|---|
| B. bassiana K4B1 | Ef lolCDFTEOUMNP and Eu lolA1 | pBTL15, pBTL16, pBTL17, pBTL18 | Yes | 0.055 μM NFL, 0.065 μM loline |
| E. festucae Fl1 | Ef lolDFTEOU and Eu lolA1 | PBTL15, pBTL16, pBTL17 | Yes | 0.22 μM NANL (in cultures fed with 1.6 mM ACPP) |

Expression of P. expansum Lol Genes Result in Loline Production in Heterologous Hosts Heterologous hosts A. niger and B. bassiana, which were capable of producing ACPP by expression of Pe lolC (Table 5), were transformed with Epichloë to lolDFTA1, or P. expansum to lolDFTO, henceforth Pe to lolDFTO, or subsets of these genes thereof. All genes in transformants were confirmed to be expressed using qRT-PCR. Both A. niger and B. bassiana successfully produced loline pathway intermediates ACPP, I-AP, and AcAP in the transformant strains expressing the Pe lolCDFTO genes (see Table 7 for details). However, in both A. niger and B. bassiana, transformants did not produce any detectable levels of NANL despite producing relatively high amounts of the precursor intermediate AcAP. This was unexpected as these transformants were expressing Pe lolO≥1-fold relative to actin, compared to previous transformants which produced detectable levels of NANL with even ≤1-fold expression of Ef lolO (relative to actin). This may indicate that, at least in heterologous systems. Pe lolO is less efficient than Ef lolO in converting AcAP to NANL. Therefore, Ef lolO was transformed to B. bassiana transformants already expressing Pe lolCDFTO gene array. Biological triplicates of 17 transformants that resulted from transformation of Ef lolO to the Pe CDFTO background were screened for Ef lolO and Pe lolO expression levels. From these, 12 transformants with the highest Ef lolO/Pe lolO expression were selected for testing gene expression of the remaining loline genes. (see Table 8 for expression of Pe lolC, D, F, T, O and Ef lolO in biological triplicates of the 12 transformants). Variable gene expression further supported selection against toxic intermediate production in this system and highlighted the requirement for careful selection of transformants with appropriate gene expression ratios. A transformant (no. 17 in Table 8), which did not express Pe lolC, but expressed all five subsequent genes, was fed with 2 mM ACPP and produced 3.63 μM NANL.

TABLE 7

Summary observations of expression of P. expansum lol genes and lolines and/or intermediates production in hosts tested positive for ACPP with Pe lolC expression

| Fungus | Summary of transformed genes of interest | Plasmid number | Transcription of lol genes | Lolines and/or intermediates detected |
|---|---|---|---|---|
| A. niger ATCC 1015 | Pe lolCDFTO | pBTL74, pBTL78, pBTL77, pBTL76, pBTL75 | Yes | 610 μM ACPP, 450 μM 1-AP, 7.3 μM AcAP (in the transformant with the most loline pathway output); NANL not detected |
| A. niger ATCC 1015 | Pe lolC, Ef lolDFT and Eu lolA1 | pBTL74, pBTL38, pBTL32, pBTL40, pBTL57 | Yes | 385 μM ACPP, 45 μM 1-AP, 18 μM AcAP (in the transformant with the most loline pathway output) |
| B. bassiana K4B1 | Pe lolCDFTO | pBTL74, pBTL78, pBTL77, pBTL76, pBTL75 | Yes | 1892 μM ACPP, 35 μM 1-AP, 68 μM AcAP (in the transformant with the most loline pathway output); NANL not detected. |
| B. bassiana K4B1 | Pe lolCDFTO and Ef lolO | pBTL74, pBTL78, pBTL77, pBTL76, pBTL75, pBTL33 | Yes | 3.63 μM NANL (in a transformant expressing Pe lolDFTO and Ef lolO fed with 2 mM ACPP). |

TABLE 8

Gene expression in biological triplicate cultures of *B. bassiana* transformants positive for Ef lolO in Pe lolC, D, F, T, O parent background

| | | Fold change (relative to act) | | | | | | |
|---|---|---|---|---|---|---|---|---|
| Isolate number | Triplicate ID | Pe lolC | Pe lolD | Pe lolF | Pe lolT | Pe lolO | Ef lolO | Chemical analysis |
| 5 | 5a | 0.07 | 13.91 | 0.23 | 0.05 | 3.58 | 6.61 | Not processed for chemical analysis since all gene expressed but low expression of lolF, T. |
| | 5b | 2.40 | 11.70 | 0.36 | 0.24 | 2.73 | 3.88 | |
| | 5c | 3.59 | 19.18 | 3.58 | 0.35 | 2.51 | 2.84 | |
| 7 | 7a | 15.24 | 30.73 | 0.00 | 0.00 | 3.77 | 3.17 | Not processed for chemical analysis since Pe lolF, T not expressed. |
| | 7b | 12.94 | 34.60 | 0.00 | 0.00 | 3.77 | 3.60 | |
| | 7c | 17.15 | 25.39 | 0.00 | 0.00 | 3.39 | 4.85 | |
| 8 | 8a | 12.52 | 34.72 | 52.31 | 4.10 | 3.36 | 1.49 | 2142 µM ACPP, 73 µM 1-AP and 4 µM AcAP. NANL not detected. |
| | 8b | 8.33 | 2.84 | 31.88 | 5.33 | 4.13 | 2.53 | |
| | 8c | 9.03 | 13.58 | 41.65 | 3.16 | 4.57 | 3.10 | |
| 9 | 9a | 16.06 | 12.03 | 0.00 | 0.00 | 3.72 | 4.56 | Not processed for chemical analysis since Pe lolF, T not expressed. |
| | 9b | 23.27 | 9.19 | 0.00 | 0.00 | 6.41 | 7.00 | |
| | 9c | 11.48 | 37.46 | 0.02 | 0.00 | 4.80 | 4.01 | |
| 14 | 14a | 24.59 | 0.00 | 5.40 | 0.00 | 1.45 | 15.88 | Not processed for chemical analysis since Pe lolD, T not expressed. |
| | 14b | 6.77 | 0.00 | 5.69 | 0.00 | 1.15 | 5.85 | |
| | 14c | 4.96 | 0.00 | 5.06 | 0.00 | 0.99 | 4.59 | |
| 15 | 15a | 22.36 | 8.70 | 0.00 | 4.47 | 4.85 | 8.58 | Not processed for chemical analysis since Pe lolF not expressed. |
| | 15b | 12.44 | 7.98 | 0.00 | 2.65 | 3.32 | 6.98 | |
| | 15c | 19.75 | 19.14 | 0.00 | 2.44 | 4.99 | 7.73 | |
| 17 | 17a | 0.00 | 21.16 | 10.04 | 0.93 | 4.58 | 5.11 | Only Pe lolC not expressed, hence fed 2 mM ACPP. 147 µM 1-AP, 24 µM AcAP and 3.63 µM NANL. |
| | 17b | 0.00 | 29.66 | 8.85 | 0.75 | 4.10 | 4.90 | |
| | 17c | 0.00 | 56.08 | 30.17 | 0.82 | 9.27 | 4.73 | |
| 19 | 19a | 11.88 | 12.05 | 0.00 | 0.00 | 2.82 | 3.18 | Not processed for chemical analysis since Pe lolF, T not expressed. |
| | 19b | 26.58 | 15.92 | 0.00 | 0.00 | 3.97 | 3.63 | |
| | 19c | 21.68 | 38.78 | 0.00 | 0.00 | 4.35 | 2.71 | |
| 20 | 20a | 0.00 | 0.00 | 0.00 | 0.00 | 5.36 | 13.89 | Not processed for chemical analysis since Pe lolC, D, F, T not expressed. |
| | 20b | 0.00 | 0.00 | 0.00 | 0.00 | 5.20 | 9.33 | |
| | 20c | 0.00 | 0.00 | 0.00 | 0.00 | 4.96 | 12.60 | |
| 22 | 22a | 32.89 | 59.77 | 24.56 | 5.50 | 3.89 | 5.47 | 2463 µM ACPP and 11 µM 1-AP. AcAP and NANL not detected. |
| | 22b | 46.22 | 103.09 | 44.81 | 3.54 | 6.78 | 3.93 | |
| | 22c | 21.07 | 37.53 | 11.43 | 4.05 | 3.84 | 4.00 | |
| 24 | 24a | 0.00 | 0.00 | 0.00 | 0.00 | 11.75 | 11.41 | Not processed for chemical analysis since Pe lolC, D, F, T not expressed. |
| | 24b | 0.00 | 0.00 | 0.00 | 0.00 | 4.72 | 4.82 | |
| | 24c | 0.00 | 0.00 | 0.00 | 0.00 | 10.70 | 6.46 | |

TABLE 8-continued

Gene expression in biological triplicate cultures of *B. bassiana* transformants positive for Ef lolO in Pe lolC, D, F, T, O parent background

| Isolate number | Triplicate ID | Fold change (relative to act) | | | | | | Chemical analysis |
|---|---|---|---|---|---|---|---|---|
| | | Pe lolC | Pe lolD | Pe lolF | Pe lolT | Pe lolO | Ef lolO | |
| 25 | 25a | 24.01 | 57.00 | 31.40 | 0.00 | 3.66 | 1.83 | Not processed for chemical analysis since Pe lolT not expressed. |
| | 25b | 48.38 | 129.60 | 97.61 | 0.00 | 6.61 | 3.06 | |
| | 25c | 31.34 | 183.34 | 87.54 | 0.00 | 7.87 | 2.84 | |

A native N-acetyltransferase of the heterologous host converts 1-AP to AcAP

*Epichloë* lolCDFTEOUA1 were transformed to heterologous hosts in accordance with the general scientific consensus that the former seven genes from *Epichloë* are necessary and sufficient to produce NANL, and that lolA, while not necessary for NANL production, would increase precursor OAH levels resulting in a good flux of intermediates through the pathway. However, existing experimental evidence does not fully clarify the function and necessity of lolD, lolF, lolU, and lolE for NANL production (see Table 9 for summary and references to experimental evidence of loline gene functions).

lolU was considered by the applicants to be a possible candidate for the acetylation of 1-AP to AcAP, based on the identification of an HMM signature of CoA-dependent acyltransferases superfamily in InterPro (https://www.ebi.ac.uk/interpro/) and the top hit to acetyltransferase in Swiss-MODEL structural analysis (https://swissmodel.expasy.org/). When fed with 2 mM 1-AP, AcAP was detected in two independent *B. bassiana* transformants which were expressing *E. festucae* E2368 lolU, as well as in two independent transformants without lolU. No AcAP was observed in the growth medium with 2 mM 1-AP control. No statistical difference in 1-AP acetylation was observed between lolU-containing and non-containing *B. bassiana*

TABLE 9

Putative functions of loline pathway genes and their role in the loline pathway. Note only the references which give experimental proof of gene function are listed.

| Gene name | Predicted function (as listed on Schardl et al., 2013) | Putative role of the encoded enzyme in the loline pathway | Reference for experimental evidence |
|---|---|---|---|
| lolA | Amino acid binding | Increasing the levels of OAH | Current study |
| lolC | gamma-class PLP enzyme | Formation of ACPP from proline and OAH | Current study |
| lolD | alpha-class PLP enzyme | Decarboxylation of pyrrolodinium ion | Not available |
| lolF | Monooxygenase | Oxidative decarboxylation of ACPP to form pyrrolodinium ion | Not available |
| lolT | alpha-class PLP enzyme | Cyclisation of pyrrolodinium ion(s) to form 1-AP | (Zhang, et al., 2009, Pan, et al., 2014) |
| lolE | Nonheme iron dioxygenase | Not clear | Not available |
| lolO | Nonheme iron dioxygenase | Formation of the C2-C7 ether bridge to form NANL | (Pan, et al., 2014, Pan, et al., 2018) |
| lolU | Unknown | Unknown | Not available |
| lolN | Acetamidase | Deacetylation of NANL to form norloline | (Pan, et al., 2014) |
| lolM | N-Methyltransferase | Methylation of norloline to form loline, and of loline to form NML | (Pan, et al., 2014) |
| lolP | Cytochrome P450 monooxygenase | Oxygenation of NML to form NFL | (Spiering, et al., 2008) |

The roles of lolF and lolD are well supported by biochemical theory that the pyrrolodinium ions, which are the putative products of LolD- and LolF-catalysed reactions, are likely to be highly unstable compounds not able to be synthesised for authentic standards or detected by targeted LC-MS/MS (D. Rennison, personal communication, 2016). Therefore, the applicants focused on clarifying the function of lolE and lolU.

K4B1. To further explore this preliminary data that showed that an N-acetyltransferase gene native to the host is capable of the acetylation of 1-AP to AcAP, a 1-AP feeding assay was done using a range of fungi. No ACPP or hydroxy-AcAP was detected in any culture. However, wild type strains of all fungi tested except for *E. festucae* F11, *S. cerevisiae* and *S. indica*, were capable of acetylating 1-AP to AcAP (see Table 10 for details). All other *Epichloë* strains tested (*E. uncinata* AR1006 and *E. festucae* E2368), and an F11 strain carrying Ef lolDFTEOU were capable of the acetylation however, which may indicate that the F11 strain tested may have converted 1-AP to AcAP, albeit less efficiently—and thus at levels less than the detection threshold. While the ability of wild type fungi to convert 1-AP to AcAP without lolU is not conclusive evidence that lolU plays a role in acetylation of 1-AP to AcAP in the native system, it is proof that a native acetyltransferase, perhaps universally present across Kingdom Fungi, has the ability to convert 1-AP to AcAP.

TABLE 10

Production of 1-AP to AcAP by different fungi

| Species | Strain | 1-AP fed (μM) | AcAP detected (μM) |
|---|---|---|---|
| A. niger | ATCC 1015 | 1000 | 10.99 |
| A. niger | ATCC 1015 | 1000 | 7.15 |
| B. bassiana | K4B1 | 1000 | 9.97 |
| B. bassiana | K4B1 | 1000 | 8.63 |
| B. bassiana | K4B1 lolU3 | 1000 | 8.52 |
| B. bassiana | K4B1 lolU3 | 1000 | 15.45 |
| B. bassiana | K4B1 lolU20 | 500 | 9.03 |
| B. bassiana | K4B1 lolU20 | 500 | 6.28 |
| E. festucae | F11 | 1000 | <0.25 |
| E. festucae | F11 | 1000 | <0.25 |
| E. festucae | E2368 | 500 | 2.38 |
| E. festucae | E2368 | 500 | 0.48 |
| E. festucae | F11 lol9 | 500 | 0.95 |
| E. festucae | F11 lol9 | 500 | 1.41 |
| E. uncinata | AR1006 | 500 | 0.88 |
| E. uncinata | AR1006 | 500 | 0.88 |
| E. nigrum | SF7849 | 1000 | 11.57 |
| E. nigrum | SF7850 | 1000 | 6.79 |
| P. expansum | ICMP 8595 | 1000 | 8.11 |
| P. expansum | ICMP 8595 | 1000 | 5.41 |
| R. solani | ICMP 17586 | 500 | 7.92 |
| R. solani | ICMP 17586 | 500 | 7.16 |
| Rhizopus sp. | | 1000 | 8.1 |
| Rhizopus sp. | | 1000 | 14.58 |
| S. zeae | EBTL 218 | 500 | 22.94 |
| S. zeae | EBTL 219 | 500 | 19.22 |
| T. reesei | ATCC 56765 | 1000 | 32.44 |
| T. reesei | ATCC 56765 | 1000 | 28.86 |
| S. indica | ATCC 204458 | 1000 | <3 |
| S. indica | ATCC 204458 | 1000 | <3 |
| U. isabellina | ICMP 22148 | 1000 | 70 |
| U. isabellina | ICMP 22148 | 1000 | 82 |
| K. marxianus | Y-1008 | 1000 | 310 |
| K. marxianus | Y-1008 | 1000 | 224 |
| S. cerevisiae | BY4743 | 1000 | <3 |
| S. cerevisiae | BY4743 | 1000 | <3 |

*Epichloë* lolE, the only other nonheme iron dioxygenase besides lolO present in the Clavicipitaceae loline cluster, is suggested to be 'not absolutely required' in the ether bridge formation due to unpublished observations with a lolE knockout mutant (alluded to in (Pan, et al., 2014)). However, recently it was reported that LolE has no role in vitro in the two oxygenation steps required to form NANL from AcAP (Pan, et al., 2018). But, there is no published data to provide conclusive evidence to whether LolE plays a role in vivo in one of the two oxygenation steps that are required to form NANL from AcAP. To this end, *B. bassiana* transformants expressing either lolE, lolO, or lolE and lolO together ('lolEO') were obtained, fed with 0.8 mM 1-AP, and the mycelial fraction was analysed for compounds of interest. All transformants as well as wild type *B. bassiana* fed with 1-AP produced AcAP. However, the intermediate generated by hydroxylation of AcAP (hydroxy-AcAP) and NANL were only detected in lolO and lolEO transformant cultures. No AcAP, hydroxy-AcAP, or NANL was detected in the growth medium with 0.8 mM 1-AP control. There was no correlation of lolE expression with hydroxy-AcAP levels in lolEO cultures ($R^2$=0.0009).

Discussion

The study of the current Example sought to achieve three main goals: (1) produce ACPP in heterologous fungal hosts by expression of the lolC gene; (2) produce NANL in heterologous hosts selected due to their ability to form ACPP; and (3) understand the requirement for lolE and Jo/U in the Clavicipitaceae loline production pathway.

When attempting to produce ACPP by expression of *Epichloë* lolC, the applicants observed that the native *E. festucae* gene with the introns and exons expressed under a constitutive promoter consistently resulted in a detectable lolC transcript in all filamentous fungi tested. Transcription of the gene led to ACPP production in culture in *B. bassiana*, *M. robertsii*, and the industrial strains *A. niger* and *T. reesei* (*F. festucae* F11 was not tested with the *E. festucae* lolC cassette). Although transcripts were detected in *N. crassa*, no ACPP was detected. The modified lolC—i.e., Ef lolC exons only, codon-optimized for *N. crassa*—resulted in variable levels of transcription in the tested hosts and was unsuccessful in producing ACPP in all cases. The highest amount of ACPP observed in a heterologous host expressing only Ef lolC was 1390 μM, produced by a *B. bassiana* transformant. Expression of Pe lolC was attempted only in *A. niger*, *B. bassiana*, and *T. reesei*, and resulted in successful transcription of Pe lolC and ACPP production in all three cases. The highest amount of ACPP observed in a heterologous host expressing Pe Jo/C only was 1844 μM, produced by a *B. bassiana* transformant. The maximum amount of ACPP observed in any transformant to-date is 2463 μM, which was produced by a *B. bassiana* transformant carrying Pe lolCDFTO and Ef lolO. It is noteworthy that endogenous ACPP amounts ≥3 mM has not been observed in any heterologous host tested so far. This may be due to the dose-dependent cytotoxic effect of ACPP, which has been reported for *E. uncinata* in previous literature (Faulkner, et al., 2006).

The applicants successfully produced NANL-loline-NFL, and NANL by itself, as well as the full array of chemically detectable pathway intermediates in *B. bassiana* via expression of *Epichloë* lolCDFAITEOUMNP and *Epichloë* lolCD-FAITEOU, respectively. To the best of the applicant's knowledge, this is the first report of heterologous production of the full loline pathway in a non-native host. NANL was also produced in transformants expressing *Epichloë* lolDFTA1O in the industrial *A. niger* strain ATCC 1015, those expressing Ef lolDFTEOU in *E. festucae* strain F11, and those expressing the Pe lolDFTO-Ef lolO combination in *B. bassiana* strain K4B1. The latter three cultures were all fed 1 or 2 mM ACPP as they all lacked lolC. All detectable loline pathway intermediates up to NANL, were produced by *A. niger* and *B. bassiana* transformants that were expressing Pe lolCDFTO as well, although detectable levels of NANL was absent. The *Epichloë* loline genes transformed to the heterologous hosts originated from *E. uncinata* AR1006 (Eu lolA1) and/or *E. festucae* E2368 (Ef lolCDFTE-OUMNP), which has currently been observed to produce lolines in planta only. All *Penicillium* lol genes are from *P. expansum*, the only *Penicillium* species in which the lol genes have been reported to-date. To the best of the applicant's knowledge, the current study is also the first report of successful heterologous expression of any Pe lol gene.

Analysis of loline gene expression data showed possible bottlenecks in expression of genes such as lolF and lolO. Re-transformation of lolO under the *E. festucae* F11 histone H3 promoter that was previously seen to produce relatively 'high' gene expression, increased the NANL level from 0.385 μM in Bb H15 to 1.209 μM in Bb O16. A further increase in production in the BbO16 strain was achieved by feeding with iron (in the form of ammoniumiron(II)sulfate hexahydrate) and 2-oxoglutarate, which have been shown to bias the oxygenation reaction catalyzed by lolO-encoded enzyme towards NANL (Pan, et al., 2018).

The applicants saw that both wild type *B. bassiana* without any loline genes and *B. bassiana* lolU transformants accumulated AcAP when fed with 1-AP. This is consistent with the previous observation that there was no obvious change in the loline alkaloid profile of lolU RNAi transformants (Pan, 2014). Therefore, the applicants conclude that lolU, although a putative acetyl transferase, is not exclusively responsible for the acetylation of 1-AP to AcAP, and that a native gene of the heterologous host is capable of this conversion. The applicants also observed no lolU expression in transformant Bb O16, although it produced NANL. Collectively, these observations make the necessity of lolU in the loline pathway questionable.

Production of NANL in *A. niger* ATCC 1015 strain is of significance as it is a strain well-suited—and commonly used—in fermentation industry. *B. bassiana*, the heterologous host which has produced the highest levels of lolines in the systems tested so far, is reported as a generalist systemic endophyte. Suitability when using as a spray treatment, lifespan in soil vs. foliage, effect on plant growth, and ability to form a loline-producing but non-sporulating mutant all remain basic questions to be answered.

Based on our observations, a two-step screen, which consists of checking the ability of a selected fungus to (1) produce ACPP through expression of lolC and (2) convert 1-AP to AcAP without any transgenes, is proposed when selecting a heterologous host for expression of lolines. If a fungus is capable of both, and is fermentation compatible and/or is an established endophyte, it may be an optimal heterologous host for loline production. The best experimental approach should be then determined based on the ACPP- and 1-AP-feeding experiment results and availability of selectable markers for the selected fungus. If a fungus with a high potential as an endophyte or fermentation compatibility is capable of producing ACPP, but is unable to convert 1-AP to AcAP, it may be useful to check if it could accumulate 'high' levels of 1-AP. If so, it may be used in a sequential fermentation, where the 1-AP formed is converted to the next products of the pathway by a co-cultivated host. Alternatively, if a gene that can convert 1-AP to AcAP is identified, it can be expressed in the fungus along with the other loline genes, thus giving it the ability to make the desired end product. On the other hand, if a fungus is capable of the 1-AP to AcAP conversion, but cannot produce ACPP, it may be useful to determine if ACPP-toxicity has led to the mortality of ACPP-producers and if so, an approach which transforms other desired loline genes prior to transformation of lolC, and transformation of lolC last could be considered. A case-by-case review of risks vs. benefits for each scenario is recommended.

Following the experiments of this example, the applicants postulate that, contrary to previous expectation for requirement of seven genes, expression of just five genes—lolC, lolD, lolF, lolT, lolO—in a heterologous host should result in the production of NANL—the first fully cyclized loline intermediate of the pathway.

TABLE 11

Detail of loline gene constructs used in the current application

| Name | Alternative name | Transgene promoter(s) | Promoter organism | loline gene | (Predicted) Gene function | Gene origin | Gene modifications |
|---|---|---|---|---|---|---|---|
| pBTL2 | pBAR-GFP | Translation elongation factor 1α | *Aureobasidium pullulans* | None | Not applicable | Not applicable | Not applicable |
| pBTL4 | pUC57-lolCDF | Glyceraldehyde 3-phosphate | *M. robertsii* ARSEF 23 | lolC | γ-class PLP cystathionine synthase | *E. festucae* E2368 | Codon-optimised for *N. crassa*, CDS, C terminal HA tag |
| | | Glyceraldehyde 3-phosphate | *M. robertsii* ARSEF 23 | lolD | PLP-containing ornithine decarboxylase | *E. festucae* E2368 | Codon-optimised for *N. crassa*, CDS, C terminal HA tag |
| | | Glyceraldehyde 3-phosphate | *M. robertsii* ARSEF 23 | lolF | FAD-containing monooxygenase | *E. festucae* E2368 | Codon-optimised for *N. crassa*, CDS, C terminal HA tag |
| pBTL5 | pBargfp-lolCDF | Glyceraldehyde 3-phosphate | *M. robertsii* ARSEF 23 | lolC | γ-class PLP cystathionine synthase | *E. festucae* E2368 | Codon-optimised for *N. crassa*, CDS, C terminal HA tag |
| | | Glyceraldehyde 3-phosphate | *M. robertsii* ARSEF 23 | lolD | PLP-containing ornithine decarboxylase | *E. festucae* E2368 | Codon-optimised for *N. crassa*, CDS, C terminal HA tag |
| | | Glyceraldehyde 3-phosphate | *M. robertsii* ARSEF 23 | lolF | FAD-containing monooxygenase | *E. festucae* E2368 | Codon-optimised for *N. crassa*, CDS, C terminal HA tag |
| pBTL6 | pH3-lolC | Histone H3 | *E. festucae* Fl1 | lolC | γ-class PLP cystathionine synthase | *E. festucae* E2368 | none |
| pBTL8 | pChuka4:lolC | TDH3 (same as glyceraldehyde 3-phosphate) | *S. cerevisiae* BY4743 | lolC | γ-class PLP cystathionine synthase | *E. festucae* E2368 | Codon-optimised for *N. crassa*, CDS |
| pBTL9 | pUC57-T2A::TEO | Translation elongation factor 1α | *E. festucae* E2368 | lolT | PLP-containing pyrolizidinase | *E. festucae* E2368 | T2A peptides between lolT and lolE, and between lolE and lolO. Codon-optimized for *N. crassa*, CDS |
| | | Translation elongation factor 1α | *E. festucae* E2368 | lolE | oxidoreductase | *E. festucae* E2368 | T2A peptides between lolT and lolE, and between lolE and lolO. Codon-optimized for *N. crassa*, CDS |

TABLE 11-continued Detail of loline gene constructs used in the current application

| Name | Alternative name | Transgene promoter(s) | Promoter organism | loline gene | (Predicted) Gene function | Gene origin | Gene modifications |
|---|---|---|---|---|---|---|---|
| | | Translation elongation factor 1α | E. festucae E2368 | lolO | non-heme iron oxygenase | E. festucae E2368 | T2A peptides between lolT and lolE, and between lolE and lolO. Codon-optimized for N. crassa, CDS |
| pBTLTOPO1 | TOPO synthetic lolT gblock | Translation elongation factor 1α | | lolT | PLP-containing pyrrolizidinase | E. festucae E2368 | Codon-optimised for N. crassa, CDS |
| pBTLTOPO2 | TOPO synthetic lolE gblock | Translation elongation factor 1α | | lolE | oxidase | E. festucae E2368 | Codon-optimised for N. crassa, CDS |
| pBTLTOPO3 | TOPO synthetic lolO gblock | Translation elongation factor 1α | | lolO | non-heme iron oxygenase | E. festucae E2368 | Codon-optimised for N. crassa, CDS |
| pBTL10 | WT-DFA | Glyceraldehyde 3-phosphate | M. robertsii ARSEF 23 | lolD | PLP-containing ornithine decarboxylase | E. festucae E2368 | none |
| | | Glyceraldehyde 3-phosphate | E. festucae Fl1 | lolF | FAD-containing monooxygenase | E. festucae E2368 | none |
| | | Histone H3 | E. festucae Fl1 | lolA1 | Amino acid binding | E. uncinata AR1006 | CDS |
| pBTL11 | WT-CDFA | Translation elongation factor 1α | M. robertsii ARSEF 23 | lolC | γ-class PLP cystathionine synthase | E. festucae E2368 | none |
| | | Glyceraldehyde 3-phosphate | M. robertsii ARSEF 23 | lolD | PLP-containing ornithine decarboxylase | E. festucae E2368 | none |
| | | Glyceraldehyde 3-phosphate | E. festucae Fl1 | lolF | FAD-containing monooxygenase | E. festucae E2368 | none |
| | | Histone H3 | E. festucae Fl1 | lolA1 | Amino acid binding | E. uncinata AR1006 | CDS |
| pBTL12 | WT-TEOU | Hexokinase-1 | M. robertsii ARSEF 23 | lolT | PLP-containing pyrrolizidinase | E. festucae E2368 | none |
| | | Histone H3 | M. robertsii ARSEF 23 | lolE | oxidase | E. festucae E2368 | none |
| | | Glyceraldehyde 3-phosphate | A. nidulans | lolO | non-heme iron oxygenase | E. festucae E2368 | Contains SNP |
| | | Translation elongation factor 1α | M. robertsii ARSEF 23 | lolU | 15-O-acetyltransferase | E. festucae E2368 | none |
| pBTL13 | pChuk4:lolC (Sc, with HA tag) | TDH3 (same as glyceraldehyde 3-phosphate) | S. cerevisiae BY4743 | lolC | γ-class PLP cystathionine synthase | E. festucae E2368 | Codon-optimised for s. cerevisiae, CDS, C terminal HA tag |
| pBTL14 | pChuk4:lolC (Sc, without HA tag) | TDH3 (same as glyceraldehyde 3-phosphate) | S. cerevisiae BY4743 | lolC | γ-class PLP cystathionine synthase | E. festucae E2368 | Codon-optimised for N. crassa, CDS |
| pBTL15 | pCA | Translation elongation factor 1α | M. robertsii ARSEF 23 | lolA1 | Amino acid binding | E. uncinata AR1006 | CDS |
| | | Histone H3 | E. festucae Fl1 | lolC | γ-class PLP cystathionine synthase | E. festucae E2368 | none |
| pBTL16 | pDFT | Histone H3 | E. festucae Fl1 | lolD | PLP-containing ornithine decarboxylase | E. festucae E2368 | none |
| | | Histone H3 | B. bassiana K4B1 | lolF | FAD-containing monooxygenase | E. festucae E2368 | none |
| | | Translation elongation factor 1α | M. robertsii ARSEF 23 | lolT | PLP-containing pyrrolizidinase | E. festucae E2368 | none |
| pBTL17 | pEOU | Histone H3 | E. festucae Fl1 | lolE | oxidase | E. festucae E2368 | none |
| | | Histone H3 | B. bassiana K4B1 | lolO | non-heme iron oxygenase | E. festucae E2368 | none |
| | | Translation elongation factor 1α | M. robertsii ARSEF 23 | lolU | 15-O-acetyltransferase | E. festucae E2368 | none |
| pBTL18 | pMNP | Histone H3 | E. festucae Fl1 | lolM | N-methyltransferase | E. festucae E2368 | none |
| | | Histone H3 | B. bassiana K4B1 | lolN | acetamidase | E. festucae E2368 | none |
| | | Translation elongation factor 1α | M. robertsii ARSEF 23 | lolP | cytochrome P450 | E. festucae E2368 | None |
| pBTL32 | plolFnew | Histone H3 | E. festucae Fl1 | lolF | FAD-containing monooxygenase | E. festucae E2368 | None |

TABLE 11-continued

Detail of loline gene constructs used in the current application

| Name | Alternative name | Transgene promoter(s) | Promoter organism | loline gene | (Predicted) Gene function | Gene origin | Gene modifications |
|---|---|---|---|---|---|---|---|
| pBTL33 | plolOnew | Histone H3 | E. festucae Fl1 | lolO | non-heme iron oxygenase | E. festucae E2368 | None |
| pBTL38 | plolD | Histone H3 | E. festucae Fl1 | lolD | PLP-containing ornithine decarboxylase | E. festucae E2368 | None |
| pBTL40 | plolT | Translation elongation factor 1α | M. robertsii ARSEF 23 | lolT | PLP-containing pyrrolizidinase | E. festucae E2368 | none |
| pBTL55 | lolU overexpressor | Class I Hydrophobin | B. bassiana K4B1 | lolU | 15-O-acetyltransferase | E. festucae E2368 | None |
| pBTL56 | lolO overexpressor | Class I Hydrophobin | B. bassiana K4B1 | lolO | non-heme iron oxygenase | E. festucae E2368 | none |
| pBTL57 | plolA | Translation elongation factor 1α | M. robertsii ARSEF 23 | lolA1 | Amino acid binding | E. uncinata AR1006 | CDS |
| pBTL58 | plolC | Histone H3 | E. festucae Fl1 | lolC | γ-class PEP cystathionine synthase | E. festucae E2368 | none |
| pBTL59 | plolE | Histone H3 | E. festucae Fl1 | lolE | oxidase | E. festucae E2368 | none |
| pBTL60 | plolO | Histone H3 | B. bassiana K4B1 | lolO | non-heme iron oxygenase | E. festucae E2368 | none |
| pBTL61 | plolU | Translation elongation factor 1α | M. robertsii ARSEF 23 | lolU | 15-O-acetyltransferase | E. festucae E2368 | none |
| pBTL62 | plolM | Histone H3 | E. festucae Fl1 | lolM | N-methyltransferase | E. festucae E2368 | none |
| pBTL63 | plolN | Histone H3 | B. bassiana K4B1 | lolN | acetamidase | E. festucae E2368 | none |
| pBTL64 | plolP | Translation elongation factor 1α | M. robertsii ARSEF 23 | lolP | cytochrome P450 | E. festucae E2368 | none |
| pBTL71 | pFl1H3/lolT/glaA | Histone H3 | E. festucae Fl1 | lolT | PLP-containing pyrrolizidinase | E. festucae E2368 | none |
| pBTL74 | pPe-lolC | Histone H3 | E. festucae Fl1 | lolC | γ-class PLP cystathionine synthase | P. expansum ICMP 8595 | none |
| pBTL75 | pPe-lolO | Histone H3 | E. festucae Fl1 | lolO | non-heme iron oxygenase | P. expansum ICMP 8595 | none |
| pBTL76 | pPe-lolT | Histone H3 | E. festucae Fl1 | lolT | PLP-containing pyrrolizidinase | P. expansum ICMP 8595 | none |
| pBTL77 | pPe-lolF | Histone H3 | E. festucae Fl1 | lolF | FAD-containing monooxygenase | P. expansum ICMP 8595 | none |
| pBTL78 | pPe-lolD | Histone H3 | E. festucae Fl1 | lolD | PLP-containing ornithine decarboxylase | P. expansum ICMP 8595 | none |
| pBTL80 | $P_{PiGPD}$-hph-ter$_{glaA}$ | Translation elongation factor | S. indica | lolC | γ-class PLP cystathionine synthase | P. expansum ICMP 8595 | none |
| pBTL81 | WT-TEOU | Hexokinase-1 | M. robertsii ARSEF 23 | lolT | PLP-containing pyrrolizidinase | E. festucae E2368 | none |
|  |  | Histone H3 | M. robertsii ARSEF 23 | lolE | oxidase | E. festucae E2368 | none |
|  |  | Glyceraldehyde 3-phosphate | A. nidulans | lolO | non-heme iron oxygenase | E. festucae E2368 | none |
|  |  | Translation elongation factor 1α | M. robertsii ARSEF 23 | lolU | 15-O-acetyltransferase | E. festucae E2368 | none |

Example 3: Screening Multiple Taxa for their Ability to Endogenously Generate AcAP from 1-AP Introduction/Summary The protein encoded by lolU was considered a possible candidate for the acetylation of 1-AP to AcAP, based on its structural similarity to N-acetyltransferases. However, when fed with 2 mM 1-AP, AcAP was detected in two independent B. bassiana transformants which were expressing E. festucae E2368 lolU, as well as in two independent transformants without lolU No AcAP was observed in the growth medium with 2 mM 1-AP control. This indicated that an N-acetyltransferase gene native to the host was capable of the acetylation of 1-AP to AcAP. As this gene is yet unidentified, the ability to convert 1-AP to AcAP is currently a required characteristic for a given fungus to successfully produce NANL. Therefore, a screen of multiple fungal taxa for the ability to convert 1-AP to AcAP was proposed. This screen has been done with a set of fungi from phylum Ascomycota, to which the native loline producer Epichloë species belong, and a fungus from unplaced subphylum Mucoromycota (formerly Zygomycota). All strains tested, except Epichloë festucae strain Fl1 were able to acetylate 1-AP to form AcAP.

Materials and Methods

Fungal Strains

All fungal strains (Table 12) were sub-cultured onto potato dextrose agar (PDA) from original or glycerol stocks where possible. All subsequent sub-cultures were also performed with PDA.

TABLE 12

Fungal strains used in this study

| No. | Species name | Strain | Class | Source |
|---|---|---|---|---|
| 1 | Aspergillus niger | ATCC 1015 | Eurotiomycetes | U.S.A |
| 2 | Beauveria bassiana | K4B1 | Sordariomycetes | New Zealand |
| 3 | Beauveria bassiana | K4B1::lolU3 | Sordariomycetes | New Zealand |
| 4 | Beauveria bassiana | K4B1::lolU20 | Sordariomycetes | New Zealand |
| 5 | Epichloë festucae | Fl1 | Sordariomycetes | U.S.A |
| 6 | Epicoccum sp. | SF7849 | Dothidiomycetes | New Zealand |
| 7 | Metarhizium robertsii | ARSEF 23 | Sordariomycetes | U.S.A |
| 8 | Penicillium expansum | ICMP 8595 | Eurotiomycetes | Spain |
| 9 | Rhizoctonia solani | ICMP 17586 | Agaricomycetes | New Zealand |
| 10 | Rhizopus sp. | | Mucoromycotina | New Zealand |
| 11 | Sarocladium spp. | BTL-E218 | Sordariomycetes | New Zealand |
| 12 | Trichoderma reesei | ATCC 56765 | Sordariomycetes | U.S.A |

Establishing Optimal Media for all Fungal Strains

A preliminary growth study for six wild type strains of fungi was performed using two complex media, PD broth (PDB) and sabouraud dextrose broth (SDB). The strains used were *A. niger, B. bassiana, E. festucae, M. robertsii, P. expansum*, and *T. reesei*.

A small square of fungi (approximately 0.5 cm$^2$) was added to 1 ml of MilliQ water in a sterile bead beating tube. The mycelial suspension was macerated in a tissue homogenizer for 30 seconds at 4,000 RPM. 40 µl of this mycelium was then added to four 50 ml Falcon tubes containing 2 ml of SDB or PDB in duplicate.

After one day the cultures were observed and growth was recorded. Those with significant biomass were fed with 22 µl of 60% w/v ethanol. Three days post-inoculation, the cultures were again observed and growth noted. Overall growth was measured using a subjective scale.

Fungal Cultures and Inoculation

All fungi, excluding numbers 5 and 7, were inoculated in batches, based on qualitative observations of their growth. There are three groups, with fast, medium, and slow growing species. Each fungus was correspondingly inoculated so that the feeding of 1-AP could all be performed at the same time for all species. A small square of fungi approximately 1 cm$^2$) was added to 1 ml of MilliQ water in a sterile bead beating tube. This tube was then bead beaten in a tissue homogenizer for 30 seconds at 4,000 RPM. 40 µl of this mycelium was then added to five 50 ml Falcon tubes containing 2 ml of SDB; duplicate treatment and triplicate treatment cultures. The lids were loosely fitted on the tubes and secured with sellotape. These tubes were then incubated in an upright rack at 25° C. with shaking at 125 RPM in the dark. Four media-only controls were also incubated in these conditions.

Feeding of 1-AP

1-AP solution sufficient for the required number of treatments to give a final concentration of 2 mM was run through a vacuum pump for three minutes to concentrate it, leaving a solution containing roughly 60% w/v ethanol. This 1-AP solution was then fed in equal amounts to the treatment cultures, and an equivalent volume of 60% w/v ethanol added to the control tubes. All tubes were incubated in the same conditions for 48-72 h before harvesting.

Harvesting of Chemical Samples

One ml of mycelium and broth was macerated by bead-beating in a Precellys homogenizer, then filtered through a 0.2 µm syringe filter. Filtrates were then analysed for loline intermediates via LC-MS/MS.

Biomass Measurements

For each control tube, the dry biomass was determined; the filter papers were allowed to incubate at room temperature for several days before weighing.

Results

Biomass Measurement

Individual weights of a set of labelled filter papers were recorded. Mycelium was sterilized holding ≥20 min in 10% Prevail®, and was added to the corresponding filter paper and was incubated at 60° C., overnight. As some of these papers had brown charred sections were lighter than expected, they were left on the bench for three more days and were weighed again. The average dry biomass weight for all species ranged between 22 and 52 mg. The highest biomass was produced by *A. niger* ATCC 1015, and the lowest by *E. festucae* Fl1 and *Rhizopus* spp.

Chemistry Analysis

Initially, eight different strains were analysed to test for their endogenous ability to convert 1-AP to AcAP. Of these eight, seven were found to be able to perform this conversion, with the exception being *E. festucae* Fl1. Roughly 0.5-3 percent of 1-AP was converted to AcAP. The highest average amount of AcAP measured was 267 µM by for *K. marxianus*; and the lowest was 9.1 µM by *A. niger* ATCC 1015 (Table 10).

Chemistry samples for *B. bassiana* K4B1 lolU #20, *R. solani* ICMP 17586, and *Sarocladium* spp. BTL-*E*218 were harvested, but not analysed.

Discussion

Figure 11:
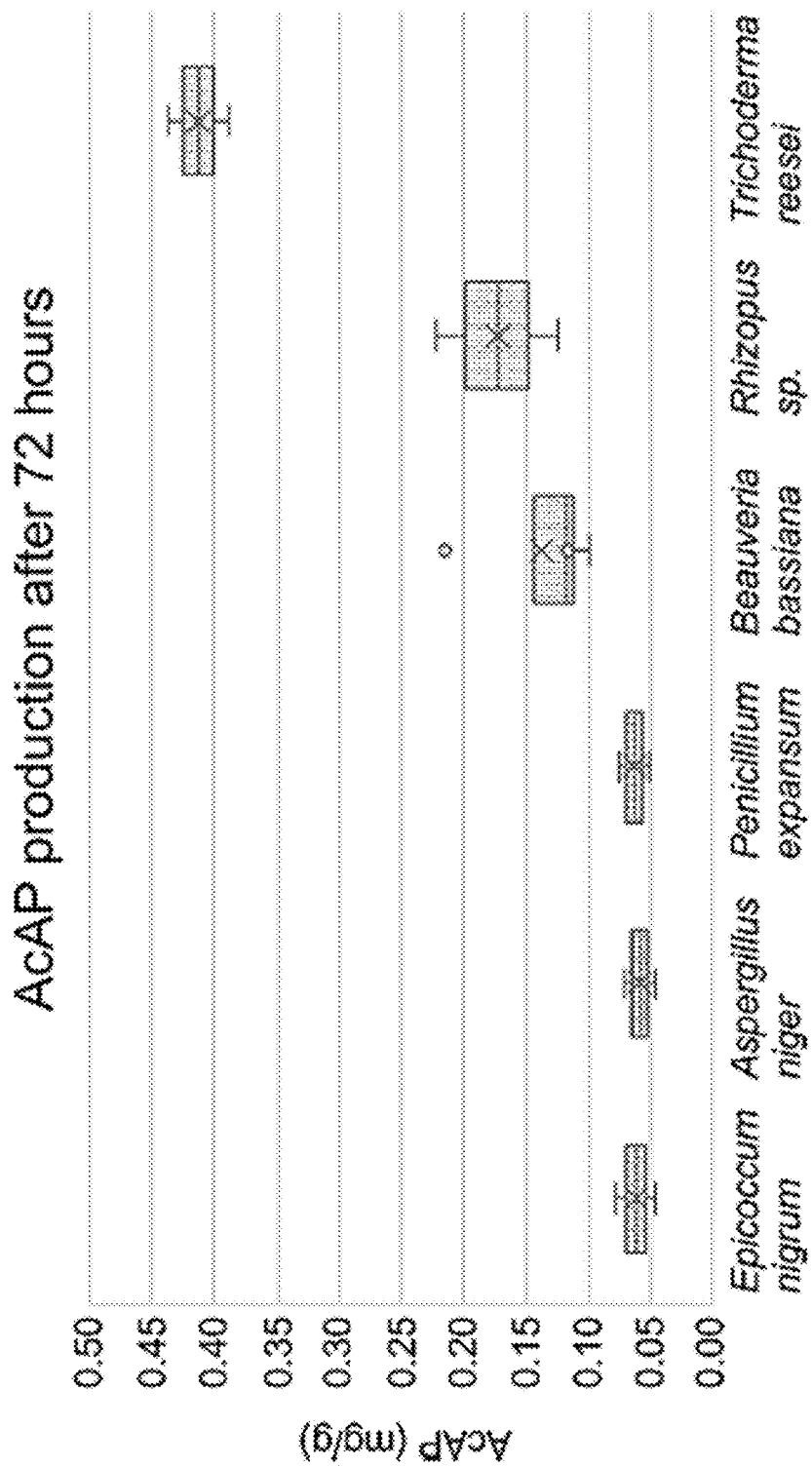
Figure 12:
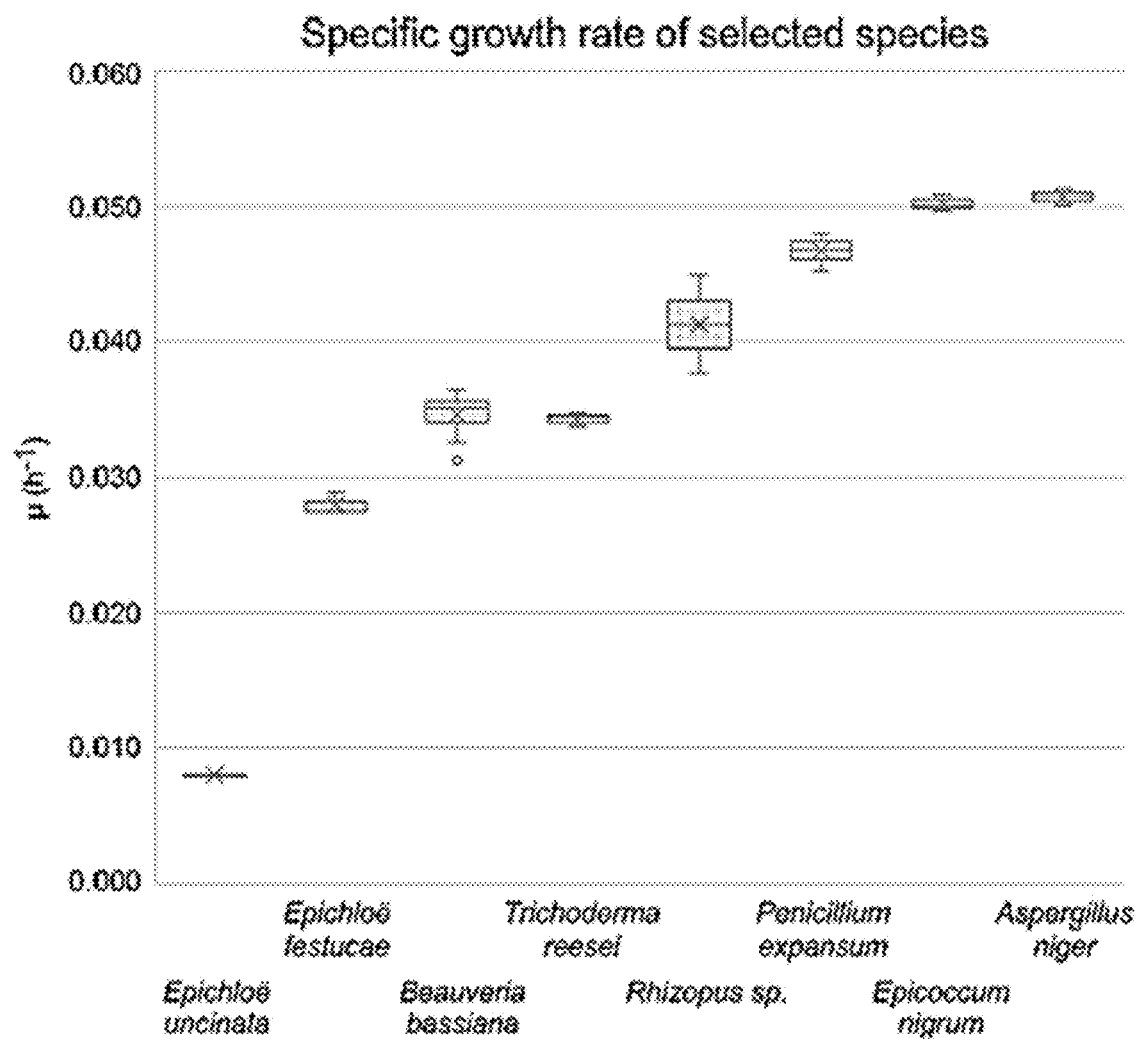

In the current screen conducted, all fungal species tested, except *E. festucae* Fl1 strain, were capable of acetylating 1-AP to AcAP. The amount of AcAP produced by different strains was low but still highly variable among species, with the production of AcAP by *T. reesei* in this study the highest detected from any 1-AP feeding study or produced by heterologous hosts in any instance (FIG. 11). This preliminary analysis supports the utility of a screen for 1-AP acetylation in identifying a suitable heterologous host for loline production.

REFERENCES

Ballester, A. R., Marcet-Houben, M., Levin, E., Sela, N., Selma-Lazaro, C., Carmona, L., et al. (2015) Genome, Transcriptome, and Functional Analyses of *Penicillium expansum* Provide New Insights Into Secondary Metabolism and Pathogenicity, Mol Plant Microbe Interact 28: 232-248.

Blankenship, J. D., Spiering, M. J., Wilkinson, H. H., Fannin, F. F., Bush, L. P., and Schardl, C. L. (2001) Production of loline alkaloids by the grass endophyte. *Neotyphodium uncinatum*, in defined media, Phytochemistry 58: 395-401.

Cakmak, M., Mayer. P., and Trauner, D. (2011) An efficient synthesis of loline alkaloids, Nat Chem 3: 543-545.

Cermak, T., Doyle, E. L., Christian, M., Wang, L., Zhang, Y., Schmidt, C., et al. (2011) Efficient design and assembly of custom TALEN and other TAL effector-based constructs for DNA targeting. Nucleic Acids Res 39: e82.

Chiang, Y. M., Oakley, C. E., Ahuja. M., Entwistle, R., Schultz, A., Chang, S. L., et al. (2013) An efficient system for heterologous expression of secondary metabolite genes in *Aspergillus nidulans, J Am Chem Soc* 135: 7720-7731.

Curtin, S. J., Zhang, F., Sander, J. D., Haun, W. J., Starker, C., Baltes, N. J., et al. (2011) Targeted mutagenesis of duplicated genes in soybean with zinc-finger nucleases, *Plant Physiol* 156: 466-473.

Faulkner, J R., Hussaini, S. R., Blankenship, J. D., Pal, S., Branan, B. M., Grossman, R. B., and Schardl, C. L. (2006) On the sequence of bond formation in loline alkaloid biosynthesis, *Chembiochem* 7: 1078-1088.

Gietz, R. D., and Schiestl, R. H. (2007) High-efficiency yeast transformation using the LiAc/SS carrier DNA/PEG method, *Nat Protoc* 2: 31-34.

Gruber, F., Visser, J., Kubicek, C. P., and de Graaff, L. H. (1990) The development of a heterologous transformation system for the cellulolytic fungus *Trichoderma reesei* based on a pyrG-negative mutant strain, *Curr Genet* 18: 71-76.

Huang, X. (1994) On global sequence alignment, *Comput Appl Biosci* 10: 227-235.

Jackson, J. A., Varney, D. R, Petroski, R. J., Powell, R. G., Bush, L. P., Siegel, M R., et al. (1996) Physiological responses of rats fed loline and ergot alkaloids from endophyte-infected tall fescue, *Drug Chem Toxicol* 19: 85-96.

Jeanmougin, F., Thompson, J. D., Gouy, M., Higgins. D. G., and Gibson, T. J. (1998) Multiple sequence alignment with Clustal X, *Trends Biochem Sci* 23: 403405.

Li, T., Liu, B., Spalding, M. H., Weeks, D. P., and Yang, B. (2012) High-efficiency TALEN-based gene editing produces disease-resistant rice, *Nat Biotechnol* 30: 390-392.

Mahfouz, M. M., Li, L., Shamimuzzaman, M., Wibowo, A., Fang, X., and Zhu, J. K. (2011) De novo-engineered transcription activator-like effector (TALE) hybrid nuclease with novel DNA binding specificity creates double-strand breaks. *Proc Natl Acad Sci USA* 108: 2623-2628.

Marcet-Houben. M., and Gabaldon, T. (2016) Horizontal acquisition of toxic alkaloid synthesis in a clade of plant associated fungi, *Fungal Genet Biol* 86: 71-80.

Navarro-Sampedro, L., Olmedo, M., and Corrochano, L M. (2007) How to transform *Neurospora crassa* by electroporation. http://www.fgsc.net/neurosporaprotocols/How%20to%20transform%20Nc%20by%20electroporation.pdf.

Needleman, S. B., and Wunsch, C. D. (1970) A general method applicable to the search for similarities in the amino acid sequence of two proteins, *J Mol Biol* 48: 443-453.

Nodvig, C. S., Nielsen, J. B., Kogle, M. E., and Mortensen, U. H. (2015) A CRISPR-Cas9 System for Genetic Engineering of Filamentous Fungi, *PLoS One* 10: e0133085.

Pan, J. (2014) Ether bridge formation and chemical diversification in loline alkaloid biosynthesis. PhD thesis. Lexington, Kentucky, USA: University of Kentucky Pan, J., Bhardwaj, M., Faulkner, J. R., Nagabhyru. P., Charlton, N. D., Higashi, R M., et al. (2014) Ether bridge formation in loline alkaloid biosynthesis, *Phytochemistry* 98: 60-68.

Pan, J., Bhardwaj, M., Nagabhyru, P., Grossman, R. B., and Schardl, C. L. (2014) Enzymes from fungal and plant origin required for chemical diversification of insecticidal loline alkaloids in grass-*Epichloe* symbiota, *PLoS One* 9: e115590.

Pan, J., Bhardwaj, M., Zhang, B., Chang, W. C., Schardl, C. L., Krebs, C., et al. (2018) Installation of the Ether Bridge of Lolines by the Iron- and 2-Oxoglutarate-Dependent Oxygenase, LolO: Regio- and Stereochemistry of Sequential Hydroxylation and Oxacyclization Reactions. *Biochemistry* 57: 2074-2083.

Penttila, M., Nevalainen, H., Ratto, M., Salminen, E., and Knowles, J. (1987) A versatile transformation system for the cellulolytic filamentous fungus *Trichoderma reesei*, *Gene* 61: 155-164.

Rice, P., Longden, I., and Bleasby, A. (2000) EMBOSS: the European Molecular Biology Open Software Suite, *Trends Genet* 16: 276-277.

Sander, J. D., Dahlborg, E. J., Goodwin, M. J., Cade, L., Zhang, F., Cifuentes, D., et al. (2011) Selection-free zinc-finger-nuclease engineering by context-dependent assembly (CoDA), *Nat Methods* 8: 67-69.

Sander, J. D., and Joung, J. K. (2014) CRISPR-Cas systems for editing, regulating and targeting genomes, *Nat Biotechnol* 32: 347-355.

Schardl, C. L., Grossman, R. B., Nagabhyru, P., Faulkner, J. R., and Mallik, U. P. (2007) Loline alkaloids: Currencies of mutualism, *Phytochemistry* 68: 980-996.

Schardl, C. L., Young, C. A., Hesse, U., Amyotte, S. G., Andreeva, K., Calie, P. J., et al. (2013) Plant-symbiotic fungi as chemical engineers: multi-genome analysis of the clavicipitaceae reveals dynamics of alkaloid loci, *PLoS Genet* 9: e1003323.

Spiering, M. J., Faulkner, J. R., Zhang, D. X., Machado, C., Grossman, R. B., and Schardl, C. L. (2008) Role of the LolP cytochrome P450 monooxygenase in loline alkaloid biosynthesis, *Fungal Genet Biol* 45: 1307-1314.

Spiering, M. J., Moon, C. D., Wilkinson, H. H., and Schardl, C. L. (2005) Gene clusters for insecticidal loline alkaloids in the grass-endophytic fungus *Neotyphodium uncinatum*, *Genetics* 169: 1403-1414.

Tzfira, T., Weinthal, D., Marton, I., Zeevi, V., Zuker, A., and Vainstein, A. (2012) Genome modifications in plant cells by custom-made restriction enzymes, *Plant Biotechnol J* 10: 373-389.

Wilkinson, H. H., Siegel, M. R., Blankenship, J. D., Mallory, A. C., Bush, L P., and Schardl, C. L. (2000) Contribution of fungal loline alkaloids to protection from aphids in a grass-endophyte mutualism, *Mol Plant Microbe Interact* 13: 1027-1033.

Yadav, V., Kumar, M., Deep, D. K., Kumar, H., Sharma. R., Tripathi, T., et al. (2010) A phosphate transporter from the root endophytic fungus *Piriformospora indica* plays a role in phosphate transport to the host plant, *J Biol Chem* 285: 26532-26544.

Zhang, D. X., Stromberg, A. J., Spiering, M. J., and Schardl, C. L. (2009) Coregulated expression of loline alkaloid-biosynthesis genes in *Neotyphodium uncinatum* cultures, *Fungal Genet Biol* 46: 517-530.

Zhang, X., Li, M., Wei, D., Wang, X., Chen, X., and Xing, L. (2007) Disruption of the fatty acid Delta6-desaturase gene in the oil-producing fungus *Mortierella isabellina* by homologous recombination, *Curr Microbiol* 55: 128-134.

Zuccaro, A., Basiewicz, M., Zurawska. M., Biedenkopf, D., and Kogel, K. H. (2009) Karyotype analysis, genome organization, and stable genetic transformation of the root colonizing fungus *Piriformospora indica. Fungal Genet Biol* 46: 543-550.

INDUSTRIAL APPLICATION

The expression constructs, host cells, and methods of the invention have utility for many agricultural, horticultural, medical and veterinary applications, such as providing horticulturalists with a useful means of controlling plant pests, and providing therapies for the treatment or prevention of insect infection or infestation in humans or non-human animals.

The invention claimed is:

1. A host cell able to produce more of at least one loline alkaloid or precursor thereof, than does a control cell, as a result of the host cell being transformed or modified to comprise at least the following polynucleotides:

i) a polynucleotide encoding a polypeptide comprising the sequence of any one of SEQ ID NO:1, 12, 13 and 61 or a variant thereof with at least 70% identity to any one of SEQ ID NO:1, 12, 13 and 61 with activity of a gamma-class pyridoxal phosphate (PLP) enzyme, ii) a polynucleotide encoding a polypeptide comprising the sequence of any one of SEQ ID NO:2, 14, 15 and 62 or a variant thereof with at least 70% identity to any one of SEQ ID NO:2, 14, 15 and 62 with activity of an alpha-class PLP enzyme, iii) a polynucleotide encoding a polypeptide comprising the sequence of any one of SEQ ID NO:3, 16, 17 and 63 or a variant thereof with at least 70% identity to of any one of SEQ ID NO:3, 16, 17 and 63 with monooxygenase activity, and iv) a polynucleotide encoding a polypeptide comprising the sequence of any one of SEQ ID NO:5, 20, 21 and 64 or a variant thereof with at least 70% identity to of any one of SEQ ID NO:5, 20, 21 and 64 with activity of an alpha-class PLP enzyme; and wherein the host cell is tolerant of endogenous (3-amino-3-carboxypropyl)proline (ACPP) production;

wherein the genome of the untransformed (wild type) host cell does not prior to transformation with the polynucleotides of i)-iv) comprise one or more LOL genes selected from lolC, lolD, lolF and lolT; and wherein the host cell is a fungal host cell.

2. The host cell of claim 1 wherein the host cell is able to produce more of at least one loline alkaloid, than does a control cell, as a result of the host cell being transformed or modified to comprise the polynucleotides.

3. The host cell of claim 1 wherein the host cell has been pre-selected for tolerance to cellular ACPP.

4. The host cell of claim 1 wherein the host cell prior to modification or transformation, is able to convert exo-1-aminopyrrolizidine (1-AP) to exo-1-acetamido-pyrrolizidine (AcAP).

5. The host cell of claim 4 wherein the host cell prior to modification or transformation, has been pre-selected for the ability to convert 1-AP to AcAP.

6. The host cell of claim 1 wherein the host cell is transformed or modified to additionally comprise a polynucleotide encoding a polypeptide comprising the sequence of any one of SEQ ID NO:7, 24, 25 and 66 or a variant thereof with at least 40% identity to any one of SEQ ID NO:7, 24, 25 and 66 with activity of a non-heme iron dioxygenase.

7. The host cell of claim 1 wherein the host cell is not transformed or modified to comprise a polynucleotide encoding a polypeptide comprising the sequence of any one of SEQ ID NO:6, 22, 23 and 65 or a variant thereof with at least 40% identity to of any one of SEQ ID NO:6, 22, 23 and 65 with activity of a non-heme iron dioxygenase.

8. The host cell of claim 1 wherein the host cell is not transformed or modified to comprise a polynucleotide encoding a polypeptide comprising the sequence of any one of SEQ ID NO:8, 26 and 27 or a variant thereof with at least 40% identity to any one of SEQ ID NO: 8, 26 and 27.

9. A method for producing at least one loline alkaloid or a precursor thereof, the method comprising culturing the host cells of claim 1 under conditions conducive to the production of the at least one loline alkaloid or precursor thereof, by the host cells.

* * * * *